US010759822B2

(12) United States Patent
Li et al.

(10) Patent No.: US 10,759,822 B2
(45) Date of Patent: Sep. 1, 2020

(54) BRAIN-TARGETING PRODRUG FOR AMPA RECEPTOR SYNERGIST, AND PHARMACEUTICAL APPLICATIONS THEREOF

(71) Applicant: Institute of Pharmacology and Toxicology Academy of Military Medical Sciences P.L.A. China, Beijing (CN)

(72) Inventors: Song Li, Beijing (CN); Xinbo Zhou, Beijing (CN); Dian Xiao, Beijing (CN); Wu Zhong, Beijing (CN); Junhai Xiao, Beijing (CN); Zhibing Zheng, Beijing (CN); Xingzhou Li, Beijing (CN); Yunde Xie, Beijing (CN); Xiaokui Wang, Beijing (CN)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 121 days.

(21) Appl. No.: 16/093,754

(22) PCT Filed: Apr. 11, 2017

(86) PCT No.: PCT/CN2017/080083
§ 371 (c)(1),
(2) Date: Oct. 15, 2018

(87) PCT Pub. No.: WO2017/177896
PCT Pub. Date: Oct. 19, 2017

(65) Prior Publication Data
US 2019/0077821 A1 Mar. 14, 2019

(30) Foreign Application Priority Data

Apr. 13, 2016 (CN) .......................... 2016 1 0223637

(51) Int. Cl.
| | |
|---|---|
| C07H 13/04 | (2006.01) |
| C07D 413/12 | (2006.01) |
| C07D 271/12 | (2006.01) |
| A61P 11/00 | (2006.01) |
| A61P 25/28 | (2006.01) |
| C07H 1/00 | (2006.01) |
| A61K 31/7056 | (2006.01) |
| A61K 31/4245 | (2006.01) |

(52) U.S. Cl.
CPC ......... *C07H 13/04* (2013.01); *A61K 31/4245* (2013.01); *A61K 31/7056* (2013.01); *A61P 11/00* (2018.01); *A61P 25/28* (2018.01); *C07D 271/12* (2013.01); *C07D 413/12* (2013.01); *C07H 1/00* (2013.01)

(58) Field of Classification Search
None
See application file for complete search history.

(56) References Cited

U.S. PATENT DOCUMENTS

| | | |
|---|---|---|
| 5,736,543 A | 4/1998 | Rogers et al. |
| 5,747,492 A | 5/1998 | Lynch et al. |
| 6,030,968 A | 2/2000 | Gall et al. |
| 2002/0055508 A1 | 5/2002 | Rogers et al. |
| 2002/0099050 A1 | 7/2002 | Lynch et al. |

FOREIGN PATENT DOCUMENTS

| | | |
|---|---|---|
| CN | 1785972 A | 6/2006 |
| CN | 101742911 A | 6/2010 |
| WO | WO 2008/143963 A1 | 11/2008 |

OTHER PUBLICATIONS

International Search Report (ISR) for PCT/CN2017/080083; I.A. fd: dated Apr. 11, 2017; dated Jul. 12, 2017, State Intellectual Property Office of the P.R. China, Beijing, China.
International Preliminary Report on Patentability (IPRP) (Chapter I of the Patent Cooperation Treaty) (PCT Rule 44bis) for PCT/CN2017/080083; I.A. fd: dated Apr. 11, 2017; dated Oct. 16, 2018, 2018, by The International Bureau of WIPO, Geneva, Switzerland.
Arai, A. et al., "A centrally active drug that modulates AMPA receptor gated currents," Brain Res. Feb. 28, 1994;638(1-2):343-6.
Arai, A. et al., "Effects of a memory-enhancing drug on DL-alpha-amino-3-hydroxy-5-methyl-4-isoxazolepropionic acid receptor currents and synaptic transmission in hippocampus," J Pharmacol Exp Ther. Aug. 1996;278(2):627-38.

(Continued)

*Primary Examiner* — Kamal A Saeed
(74) *Attorney, Agent, or Firm* — Sterne, Kessler, Goldstein & Fox P.L.L.C.

(57) ABSTRACT

Disclosed in the present invention is a compound of Formula (I), a geometric or optical isomer, a pharmaceutically acceptable salt, a solvate or a polymorph thereof. Also disclosed in the present invention is a composition comprising the compound of Formula (I), the geometric or optical isomer, the pharmaceutically acceptable salt, the solvate or the polymorph thereof. Also disclosed in the present invention is a use of the compound of Formula (I), the geometric or optical isomer, the pharmaceutically acceptable salt, the solvate or the polymorph thereof in the treatment of a disease or disorder such as a hypoglutamatergic condition, a neurodegenerative disease or respiratory depression, particularly in the treatment of a disease or disorder associated with AMPA receptor.

(I)

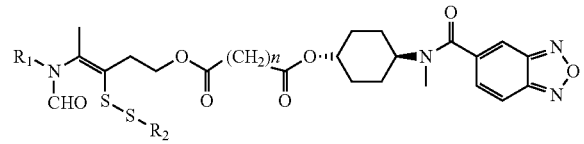

20 Claims, 1 Drawing Sheet

(56) References Cited

OTHER PUBLICATIONS

Arai, A. et al., "Factors regulating the magnitude of long-term potentiation induced by theta pattern stimulation," Brain Res. Dec. 11, 1992;598(1-2):173-84.

Chang, Q. et al., "The disease progression of Mecp2 mutant mice is affected by the level of BDNF expression," Neuron. Feb. 2, 2006;49(3):341-8.

del Cerro, S. et al., "Benzodiazepines block long-term potentiation in slices of hippocampus and piriform cortex," Neuroscience. Jul. 1992;49(1):1-6.

Fan, W. et al., "Design, synthesis and biological evaluation of brain-specific glucosyl thiamine disulfide prodrugs of naproxen," Eur J Med Chem. Sep. 2011;46(9):3651-61. doi: 10.1016/j.ejmech.2011.05.029. Epub May 20, 2011, Editions Scientifiques Elsevier, Paris, France.

Granger, R. et al., "A drug that facilitates glutamatergic transmission reduces exploratory activity and improves performance in a learning-dependent task," Synapse. Dec. 1993;15(4):326-9.

Hampson, R.E. et al., "Facilitative effects of the ampakine CX516 on short-term memory in rats: correlations with hippocampal neuronal activity," J Neurosci. Apr. 1, 1998;18(7):2748-63.

Ingvar, M. et al., "Enhancement by an ampakine of memory encoding in humans," Exp Neurol. Aug. 1997;146(2):553-9.

Ishikura, T et al., "Drug delivery to the brain. DOPA prodrugs based on a ring-closure reaction to quaternary thiazolium compounds," International Journal of Pharmaceutics 116(1), Mar. 14, 1995, pp. 51-63, available online Nov. 16, 1999, https://doi.org/10.1016/0378-5173(94)00271-6, Elsevier/North-Holland Biomedical Press, Amsterdam, Netherlands.

Kent, L. et al., "Association of the paternally transmitted common Valine allele of the Val66Met polymorphism of the brain-derived neurotrophic factor (BDNF) gene with susceptibility to ADHD," Mol Psychiatry. Oct. 2005;10(10):939-43.

Lauterborn, J.C. et al., "Positive modulation of AMPA receptors increases neurotrophin expression by hippocampal and cortical neurons," J Neurosci. Jan. 1, 2000;20(1):8-21.

Lauterborn, J.C. et al., "Chronic elevation of brain-derived neurotrophic factor by ampakines," J Pharmacol Exp Ther. Oct. 2003;307(1):297-305. Epub Jul. 31, 2003.

Lynch, G. et al., "Evidence that a positive modulator of AMPA-type glutamate receptors improves delayed recall in aged humans," Exp Neurol. May 1997;145(1):89-92.

Lynch, G. et al., "Psychological effects of a drug that facilitates brain AMPA receptors," Int Clin Psychopharmacol. Mar. 1996;11(1):13-9.

Mackowiak, M. et al., "An AMPA receptor potentiator modulates hippocampal expression of BDNF: an in vivo study," Neuropharmacology. Jul. 2002;43(1):1-10.

Monaghan, D.T. et al., "Distribution of [$^3$H]AMPA binding sites in rat brain as determined by quantitative autoradiography," Brain Res. Dec. 17, 1984;324(1): 160-4.

O'Neill, M.J. et al., "Neurotrophic actions of the novel AMPA receptor potentiator, LY404187, in rodent models of Parkinson's disease," Eur J Pharmacol. Feb. 20, 2004;486(2):163-74.

Paarmann, I. et al., "Expression of 15 glutamate receptor subunits and various splice variants in tissue slices and single neurons of brainstem nuclei and potential functional implications," J Neurochem. Apr. 2000;74(4):1335-45.

Pastalkova, E. et al., "Storage of spatial information by the maintenance mechanism of LTP," Science. Aug. 25, 2006;313(5790):1141-4.

Porrino, L.J., et al., "Facilitation of task performance and removal of the effects of sleep deprivation by an ampakine (CX717) in nonhuman primates," PLoS Biol. Sep. 2005;3(9):e299. Epub Aug. 23, 2005, 14 pages.

Ren, J. et al., "Ampakines alleviate respiratory depression in rats," Am J Respir Crit Care Med. Dec. 15, 2006;174(12):1384-91. Epub Sep. 14, 2006.

Rex, C.S. et al., "Restoration of long-term potentiation in middle-aged hippocampus after induction of brain-derived neurotrophic factor," J Neurophysiol. Aug. 2006;96(2):677-85. Epub May 17, 2006.

Riikonen, R., "Neurotrophic factors in the pathogenesis of Rett syndrome," J Child Neurol. Oct. 2003;18(10):693-7.

Shors, T.J. et al., "Enhanced glutamatergic neurotransmission facilitates classical conditioning in the freely moving rat," Neurosci Lett. Feb. 17, 1995;186(2-3):153-6.

Stäubli, U. et al., "Centrally active modulators of glutamate receptors facilitate the induction of long-term potentiation in vivo," Proc Natl Acad Sci U S A. Nov. 8, 1994;91(23):11158-62.

Stäubli, U. et al., "Facilitation of glutamate receptors enhances memory," Proc Natl Acad Sci U S A. Jan. 18, 1994;91(2):777-81.

Xiao, D et al., Design, Synthesis and Biological Evaluation of Brain-Targeted Thiamine Disulfide Prodrugs of Ampakine Compound LCX001, Molecules. Apr. 14, 2016;21(4):488, 14 pages. doi: 10.3390/molecules21040488, MDPI: Basel, Switzerland.

Whitlock, J.R. et al., "Learning induces long-term potentiation in the hippocampus," Science. Aug. 25, 2006;313(5790):1093-7.

Zhao, Y et al., "Design, synthesis and biological evaluation of brain targeting 1-ascorbic acid prodrugs of ibuprofen with "lock-in" function," Eur J Med Chem. Jul. 23, 2014;82:314-23. doi: 10.1016/j.ejmech.2014.05.072. Epub Jun. 2, 2014, Editions Scientifiques Elsevier, Paris, France.

BRAIN-TARGETING PRODRUG FOR AMPA RECEPTOR SYNERGIST, AND PHARMACEUTICAL APPLICATIONS THEREOF

TECHNICAL FIELD

The present invention relates to a compound, a pharmaceutical composition and a method for the prevention and treatment of cerebral insufficiency, wherein the prevention and treatment of cerebral insufficiency include enhancing receptor functioning in synapses in brain networks responsible for a variety of behaviors. The brain networks are involved in basic functions (e.g., breathing) and more complex functions (e.g., memory and cognition). Imbalance in neuronal activities between different brain regions may lead to many disorders, including psychiatric and neurological disorders, respiratory depression, and a disorder related to deficiency in the neurotrophin. The psychiatric and neurological disorders include memory impairment, Parkinson's disease, schizophrenia, attention deficit and affective or dysthymic disorder. In a particular aspect, the present invention relates to a compound for use in the treatment of the disease described above and a method for such treatment by using the compound.

BACKGROUND ART

Two types of postsynaptic ionotropic glutamate receptors are stimulated by glutamate released at synapses at many sites of mammalian forebrain. These two types of receptors are usually referred to as DL-α-amino-3-hydroxy-5-methyl-4-isoxazolyl propionic acid (AMPA) receptors and N-methyl-D-aspartic acid (NMDA) receptors. AMPA receptors mediate a voltage independent fast excitatory postsynaptic current (the fast EPSC), whereas NMDA receptors generate a voltage-dependent, slow excitatory current. Studies carried out in slices of hippocampus or cortex indicate that the AMPA receptor mediated fast EPSC is generally the dominant component at most glutamatergic synapses, and the activity of AMPA receptors is usually a prerequisite for the activity of NMDA receptors.

AMPA receptors are expressed throughout the central nervous system. As reported by Monaghan et al., these receptors are found in high concentrations in the superficial layers of neocortex, in each of the major synaptic zones of hippocampus, and in the striatal complex (Monaghan et al., Brain Research, 324: 160-164 (1984)). Studies in animals and humans indicate that these structures organize complex perceptual-motor processes and provide the basis for higher-level behaviors. Thus, AMPA receptors mediate transmission in those brain networks responsible for a lot of cognitive activities. In addition, AMPA receptors are expressed in a brain region that regulates inspiratory driving responsible for controlling respiration (Paarmann et al., Journal of Neurochemistry, 74: 1335-1345 (2000)).

Therefore, drugs that modulate and thereby enhancing the function of AMPA receptors could have significant benefits for intellectual performance as well as reversal of respiratory depression induced by medication such as opioids and opiates, or other ways. Such drugs may also be beneficial for memory encoding. Experimental studies, such as those reported by Arai and Lynch, Brain Research 598:173-184 (1992), indicate that increasing the size of AMPA receptor-mediated synaptic response(s) enhances the induction of long-term potentiation (LTP). LTP is a stable increase in the strength of synaptic connection generated follows repetitive physiological activities occurring in the brain in the process of learning.

Compounds that enhance the function of the AMPA subtype of glutamate receptors facilitate the induction of LTP and the acquisition of learned tasks as measured by a number of paradigms. See, for example, Granger et al., Synapse 15:326-329 (1993); Staubli et al., PNAS 91:777-781 (1994); Arai et al., Brain Res. 638:343-346 (1994); Staubli et al., PNAS 91:11158-11162 (1994); Shors et al., Neurosci. Let. 186:153-156 (1995); Larson et al., J. Neurosci. 15:8023-8030 (1995); Granger et al., Synapse 22:332-337 (1996); Arai et al., JPET 278:627-638 (1996); Lynch et al., Internat. Clin. Psychopharm. 11:13-19 (1996); Lynch et al., Exp. Neurology 145:89-92 (1997); Ingvar et al., Exp. Neurology 146:553-559 (1997); Hampson, et al., J. Neurosci. 18:2748-2763 (1998); Porrino et al., PLoS Biol 3(9): 1-14 (2006) and Lynch and Rogers, U.S. Pat. No. 5,747,492. There is a considerable body of evidence showing that LTP is the substrate of memory. For example, compounds that block LTP interfere with memory formation in animals, and certain drugs that disrupt learning in humans antagonize the stabilization of LTP, as reported by del Cerro and Lynch, Neuroscience 49: 1-6 (1992). Learning a simple task induces LTP in hippocampus that occludes LTP generated by high frequency stimulation (Whitlock et al., Science 313:1093-1097 (2006)) and a mechanism that maintains LTP sustains spatial memory (Pastalkova, et al., Science 313:1141-1144 (2006)). Of significant importance to the field of learning is the finding that in vivo treatments with a positive AMPA-type glutamate receptor modulator restores stabilization of basal dendritic LTP in middle-aged animals (Rex, et al., J. Neurophysiol. 96:677-685 (2006)).

Drugs that enhance the functioning of the AMPA receptor can effectively reverse opioid- and barbiturate-induced respiratory depression without reversing the analgesic response (Ren et al, American Journal of Respiratory and Critical Care Medicine, 174: 1384-1391 (2006). Therefore these drugs may be useful in preventing or reversing opioid-induced respiratory depression and in alleviating other forms of respiratory depression including sedative use and sleep apnea. Excitatory synaptic transmission provides a major pathway by which neurotrophins are increased within specific brain regions. As such, potentiation of AMPA receptor function by modulators has been found to increase levels of neurotrophins, particularly brain derived neurotrophic factor, or BDNF. See, for example, Lauterborn, et al., J. Neurosci. 20:8-21 (2000); Gall, et al., U.S. Pat. No. 6,030,968; Lauterborn, et al., JPET 307:297-305 (2003); and Mackowiak, et al., Neuropharmacology 43:1-10 (2002). Other studies have linked BDNF levels to a number of neurological diseases, such as Parkinson's disease, Attention Deficit Hyperactivity Disorder (ADHD), autism, Fragile-X Syndrome, and Rett Syndrome (RTT). See, for example, O'Neill, et al., Eur. J. Pharmacol. 486:163-174 (2004); Kent, et al., Mol. Psychiatry. 10:939-943 (2005); Riikonen, et al., J. Child Neurol. 18:693-697 (2003) and Chang, et al., Neuron 49:341-348 (2006). Thus, AMPA receptor synergists may be useful for the treatment of these diseases, as well as other neurological diseases resulted from an imbalance of glutamatergic or a deficit in the neurotrophin.

A class of AMPA receptor synergist can be substituted benzamides, including, for example, 6-(piperidin-1-yl-carbonyl)quinoxaline (CX516; Ampalex®). CX516 is active in animal tests for the detection of active drugs for the treatment of memory disorder, schizophrenia, and depression. In three separate clinical trials, CX516 showed evidence for the efficacy in improving various forms of human memory (Lynch et al., Internat. Clin. Psychopharm. 11:13-19 (1996); Lynch et al., Exp. Neurology 145:89-92 (1997); Ingvar et al., Exp. Neurology 146:553-559 (1997)).

Another class of AMPA receptor synergist, benzoxazines, has been discovered to have extremely high activity in vitro and in vivo models for assessing the probability of exerting cognition enhancement (Rogers and Lynch; U.S. Pat. No. 5,736,543). The substituted benzoxazines are rigid benzamide analogues with different receptor modulating properties from the flexible benzamide, CX516.

Certain substituted 2,1,3-benzoxadiazole compounds have been found significantly and surprisingly more potent in animal models of attention deficit hyperactivity disorder (ADHD), schizophrenia and cognition than previously disclosed compounds in US 2002/0055508 and US 2002/0099050. The new N,N-disubstituted amides (I) display significant activity for enhancing AMPA mediated glutamateric synaptic responses, and many of the compounds have entered into clinical research.

The compound N-(anti-4-hydroxycyclohexyl)-N-methyl-benzo[c][1,2,5]oxadiazol-5-yl-carboxamide (Compound a) is a substituted 2,1,3-benzoxadiazole. It has extremely high activity (WO2008143963). After intraperitoneal injection, it leads to a 21% increase in the amplitude of the field EPSP in the rat dentate gyrus. The compound is far more active than CX516, which gave a 9% increase in amplitude of the field EPSP after intraperitoneal injection. The compound exhibited 100% inhibition of hyperactivity induced by intraperitoneal injection of 2 mg/kg d-amphetamine.

compound a

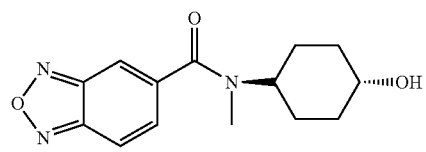

Although this class of compounds has a good activity, the clinical doses thereof are high and close to the maximum tolerated dose. For example, the clinical dose of CX717 is up to 1500 mg/d, and the clinical dose of CX1739 is also 900 mg/d. High doses can cause serious side effects. The reason is mainly due to the wide distribution of the drug in vivo. When a drug is mainly distributed in the peripheral organs, toxicity and side effects are easily produced, and at the same time, the ratio of the drug distributed in the brain tissue is decreased, reducing the efficacy of the drug.

CONTENTS OF THE PRESENT INVENTION

The present invention includes compounds of formula (I) and those as described in Specific Models for Carrying out the Present Invention. It has been found that, an administration of the compounds can increase the distribution of the AMPA receptor synergist N-(anti-4-hydroxycyclohexyl)-N-methylbenzo[c][1,2,5]oxadiazol-5-yl-carboxamide in the brain, improve the efficacy of the drug, and in the meantime reduce the distribution of the drug in peripheral organs, thereby reducing the toxicity and side effects of the drug. In addition, in the experiment against respiratory depression induced by opiates, the compounds significantly increase the survival rate of mice. The compounds are significantly and surprisingly more potent than the prototype compound (i.e., Compound a), and achieve the same anti-lethal effect as the prototype compound (i.e., Compound a) at a significantly lower molar dose. In a corresponding method of use of the compounds, including a treatment method, the compounds are at a significantly lower concentration compared to a composition disclosed in the prior art.

The present invention relates to a compound of Formula (I), a geometric or optical isomer, a pharmaceutically acceptable salt, a solvate or a polymorph thereof:

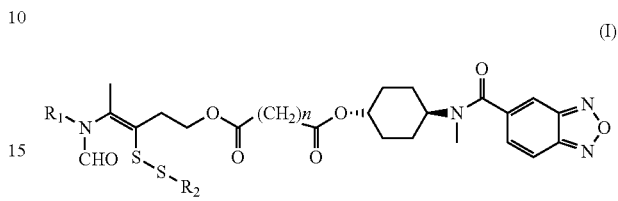

wherein, $R_1$ represents $C_1$-$C_5$ linear or branched alkyl,

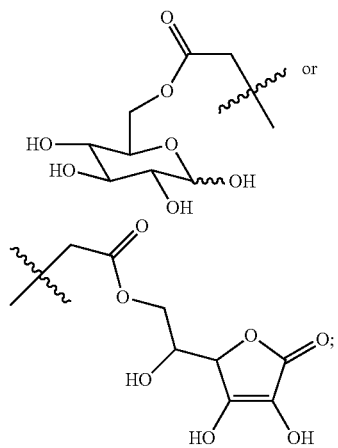

$R_2$ represents $C_1$-$C_{10}$ linear or branched alkyl, phenyl-$C_1$-$C_4$ alkyl;

n represents an integer selected from 1-5.

Disclosed in an embodiment of the present invention is a compound of Formula (I), a geometric or optical isomer, a pharmaceutically acceptable salt, a solvate or a polymorph thereof, wherein, $R_1$ represents $C_1$-$C_5$ linear or branched alkyl,

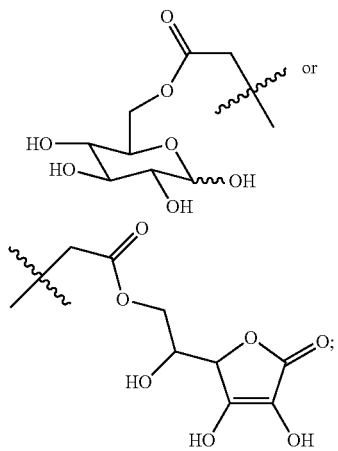

$R_2$ represents $C_1$-$C_{10}$ linear or branched alkyl, benzyl, phenylethyl, phenylpropyl; n represents an integer selected from 1-5.

Disclosed in another embodiment of the present invention is a compound of Formula (I), a geometric or optical isomer, a pharmaceutically acceptable salt, a solvate or a polymorph thereof, or any of the above embodiments thereof, wherein, $R_1$ represents $C_1$-$C_5$ linear or branched alkyl,

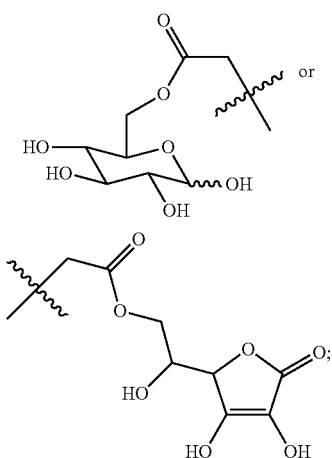

$R_2$ represents $C_1$-$C_{10}$ linear or branched alkyl;

n represents an integer selected from 1-5.

Disclosed in another embodiment of the present invention is a compound of Formula (I), a geometric or optical isomer, a pharmaceutically acceptable salt, a solvate or a polymorph thereof, or any of the above embodiments thereof, wherein, $R_1$ represents $C_1$-$C_4$ linear or branched alkyl,

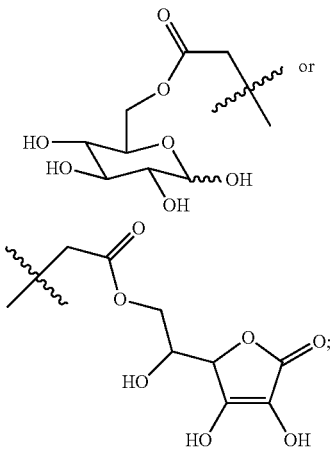

$R_2$ represents $C_1$-$C_8$ linear or branched alkyl;

n represents an integer selected from 1-4.

Disclosed in another embodiment of the present invention is a compound of Formula (I), a geometric or optical isomer, a pharmaceutically acceptable salt, a solvate or a polymorph thereof, or any of the above embodiments thereof, wherein, $R_1$ represents $C_1$-$C_4$ linear or branched alkyl,

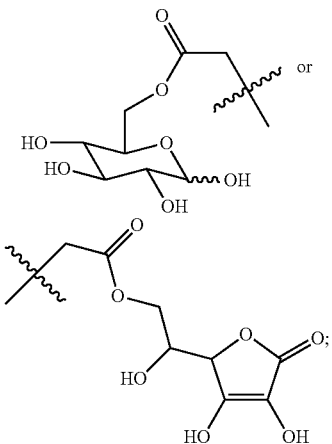

$R_2$ represents $C_1$-$C_6$ linear or branched alkyl;

n represents an integer selected from 1-3.

Disclosed in another embodiment of the present invention is a compound of Formula (I), a geometric or optical isomer, a pharmaceutically acceptable salt, a solvate or a polymorph thereof, or any of the above embodiments thereof, wherein, $R_1$ represents $C_1$-$C_4$ linear or branched alkyl,

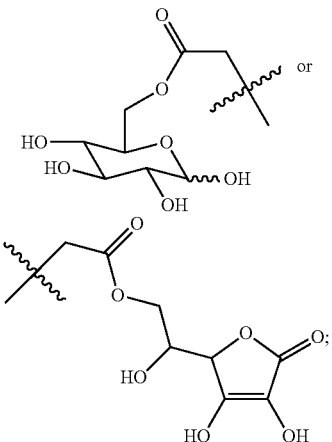

$R_2$ represents $C_1$-$C_6$ linear or branched alkyl;

n represents an integer selected from 2-4.

Disclosed in another embodiment of the present invention is a compound of Formula (I), a geometric or optical isomer, a pharmaceutically acceptable salt, a solvate or a polymorph thereof, or any of the above embodiments thereof, wherein, $R_1$ represents $CH_3$—, $CH_3CH_2$—, $CH_3CH_2CH_2$—,

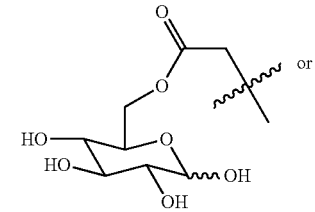

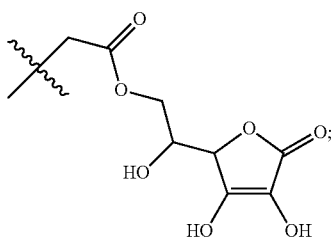

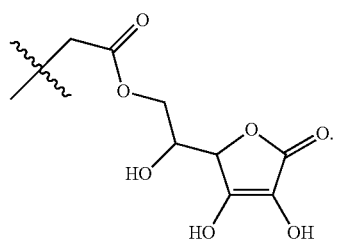

R₂ represents —CH₂CH₃, —CH₂CH₂CH₃, —CH(CH₃)₂, —CH₂CH₂CH₂CH₃, —CH₂CH(CH₃)₂, —CH₂CH₂CH₂CH₂CH₃, —CH₂CH₂CH(CH₃)₂, —CH₂CH₂CH₂CH₂CH₂CH₃ or Disclosed in another embodiment of the present invention is a compound of Formula (II), a geometric or optical isomer, a pharmaceutically acceptable salt, a solvate or a polymorph thereof, or any of the above embodiments thereof, wherein:

R₁ represents CH₃— or

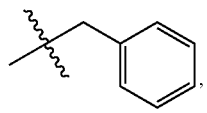

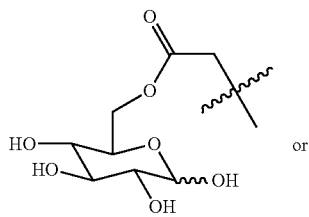

preferably, —CH₂CH₃, —CH₂CH₂CH₃, —CH(CH₃)₂, —CH₂CH₂CH₂CH₃, —CH₂CH(CH₃)₂, —CH₂CH₂CH₂CH₂CH₃, —CH₂CH₂CH(CH₃)₂ or —CH₂CH₂CH₂CH₂CH₂CH₃;

n represents 2 or 3.

Disclosed in another embodiment of the present invention is a compound of Formula (I), a geometric or optical isomer, a pharmaceutically acceptable salt, a solvate or a polymorph thereof, or any of the above embodiments thereof, wherein the compound has a structure as shown in Formula (II), preferably, CH₃—.

Disclosed in another embodiment of the present invention is a compound of Formula (I), a geometric or optical isomer, a pharmaceutically acceptable salt, a solvate or a polymorph thereof, or any of the above embodiments thereof, (II)

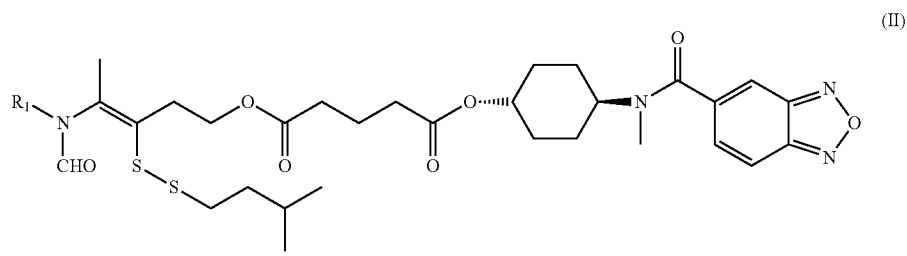

wherein, R₁ represents CH₃—, CH₃CH₂—, CH₃CH₂CH₂—, (CH₃)₂CH₂—, wherein, R₁ represents C₁-C₃ branched or non-branched alkyl,

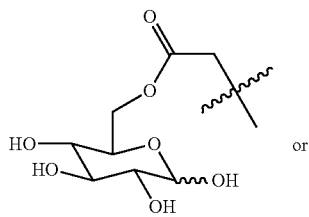 or

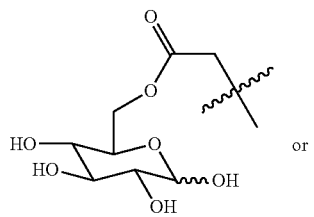 or

-continued

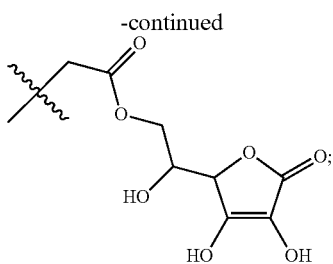

R$_2$ represents C$_1$-C$_6$ branched or non-branched alkyl;
n represents 2 or 3.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents CH$_3$—, CH$_3$CH$_2$—, CH$_3$CH$_2$CH$_2$—,

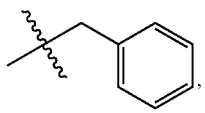 [SMILES: *Cc1ccccc1]

R$_2$ represents —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$CH$_2$CH$_2$CH$_2$CH$_3$, —CH$_2$CH$_2$CH(CH$_3$)$_2$ or preferably, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH$_2$CH$_2$CH$_2$CH$_2$CH$_3$, —CH$_2$CH$_2$CH(CH$_3$)$_2$;

n represents 2 or 3.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents C$_1$-C$_5$ linear or branched alkyl.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents C$_1$-C$_4$ linear or branched alkyl.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents C$_1$-C$_3$ linear or branched alkyl.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents methyl, ethyl, n-propyl, iso-propyl, n-butyl, sec-butyl, iso-butyl, tert-butyl, n-pentyl, 3-methyl-butyl, 2-methyl-butyl, 1-methyl-butyl, 2,2-dimethyl-propyl, 1,1-dimethyl-propyl, 1,2-dimethyl-propyl, 1-ethyl-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents methyl, ethyl, n-propyl, iso-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents methyl, ethyl, n-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents methyl.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents ethyl.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents n-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents iso-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents n-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents sec-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents iso-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents tert-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, R$_1$ represents n-pentyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_1$ represents 3-methyl-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_1$ represents 2-methyl-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_1$ represents 1-methyl-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_1$ represents 2,2-dimethyl-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_1$ represents 1,1-dimethyl-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_1$ represents 1,2-dimethyl-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_1$ represents 1-ethyl-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_1$ represents

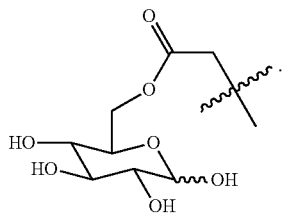 [SMILES: *CC(=O)OCC1OC(O)C(O)C(O)C1O]

Disclosed in another embodiment of the present invention is a compound of Formula (I), a geometric or optical isomer, a pharmaceutically acceptable salt, a solvate or a polymorph thereof, or any of the above embodiments thereof, wherein, $R_1$ represents

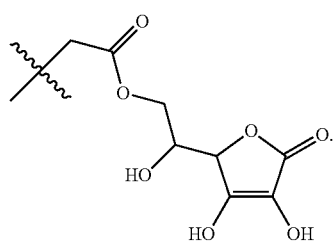 [SMILES: *CC(=O)OCC(O)C1OC(=O)C(O)=C1O]

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents $C_1$-$C_{10}$ linear or branched alkyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents $C_1$-$C_8$ linear or branched alkyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents $C_1$-$C_6$ linear or branched alkyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents methyl, ethyl, n-propyl, iso-propyl, n-butyl, sec-butyl, iso-butyl, tert-butyl, n-pentyl, 3-methyl-butyl, 2-methyl-butyl, 1-methyl-butyl, 2,2-dimethyl-propyl, 1,1-dimethyl-propyl, 1,2-dimethyl-propyl, 1-ethyl-propyl, n-hexyl, 1-methyl-n-pentyl, 2-methyl-pentyl, 3-methyl-pentyl, 4-methyl-pentyl, 1,1-dimethyl-butyl, 2,2-dimethyl-butyl, 3,3-dimethyl-butyl, 1,2-dimethyl-butyl, 1,3-dimethyl-butyl, 2,3-dimethyl-butyl, 1-ethyl-butyl, 2-ethyl-butyl, 1,2,2-trimethyl-propyl or 1,1,2-trimethyl-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents ethyl, n-propyl, iso-propyl, n-butyl, iso-butyl, n-pentyl, iso-pentyl, n-hexyl or benzyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents ethyl, n-propyl, iso-propyl, n-butyl, iso-butyl, n-pentyl, iso-pentyl or n-hexyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents methyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents ethyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents n-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents iso-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents n-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents sec-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents iso-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents tert-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents n-pentyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 3-methyl-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 2-methyl-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 1-methyl-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 2,2-dimethyl-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 1,1-dimethyl-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 1,2-dimethyl-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 1-ethyl-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents n-hexyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 1-methyl-n-pentyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 2-methyl-pentyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 3-methyl-pentyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 4-methyl-pentyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 1,1-dimethyl-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 2,2-dimethyl-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 3,3-dimethyl-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 1,2-dimethyl-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 1,3-dimethyl-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 2,3-dimethyl-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 1-ethyl-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 2-ethyl-butyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 1,2,2-trimethyl-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents 1,1,2-trimethyl-propyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents phenyl-$C_1$-$C_4$ alkyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents phenyl-$C_1$-$C_3$ alkyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents benzyl, phenylethyl, phenylpropyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents benzyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents phenylethyl.

Disclosed in another embodiment of the present invention is a compound of Formula (I), a geometric or optical isomer, a pharmaceutically acceptable salt, a solvate or a polymorph thereof, or any of the above embodiments thereof, wherein, $R_2$ represents phenylpropyl.

Disclosed in another embodiment of the present invention is a compound of Formula (I), a geometric or optical isomer, a pharmaceutically acceptable salt, a solvate or a polymorph thereof, or any of the above embodiments thereof, wherein, n represents an integer selected from 1-5, for example, 1, 2, 3, 4 or 5.

Disclosed in another embodiment of the present invention is a compound of Formula (I), a geometric or optical isomer, a pharmaceutically acceptable salt, a solvate or a polymorph thereof, or any of the above embodiments thereof, wherein, n represents an integer selected from 1-4, for example, 1, 2, 3 or 4.

Disclosed in another embodiment of the present invention is a compound of Formula (I), a geometric or optical isomer, a pharmaceutically acceptable salt, a solvate or a polymorph thereof, or any of the above embodiments thereof, wherein, n represents 2 or 3.

Disclosed in another embodiment of the present invention is a compound of Formula (I), a geometric or optical isomer, a pharmaceutically acceptable salt, a solvate or a polymorph thereof, or any of the above embodiments thereof, wherein, n represents 1.

Disclosed in another embodiment of the present invention is a compound of Formula (I), a geometric or optical isomer, a pharmaceutically acceptable salt, a solvate or a polymorph thereof, or any of the above embodiments thereof, wherein, n represents 2.

Disclosed in another embodiment of the present invention is a compound of Formula (I), a geometric or optical isomer, a pharmaceutically acceptable salt, a solvate or a polymorph thereof, or any of the above embodiments thereof, wherein, n represents 3.

Disclosed in another embodiment of the present invention is a compound of Formula (I), a geometric or optical isomer, a pharmaceutically acceptable salt, a solvate or a polymorph thereof, or any of the above embodiments thereof, wherein, n represents 4.

Disclosed in another embodiment of the present invention is a compound of Formula (I), a geometric or optical isomer, a pharmaceutically acceptable salt, a solvate or a polymorph thereof, or any of the above embodiments thereof, wherein, n represents 5.

Disclosed in another embodiment of the present invention is a compound of Formula (I), a geometric or optical isomer, a pharmaceutically acceptable salt, a solvate or a polymorph thereof, or any of the above embodiments thereof, wherein, the compound is selected from

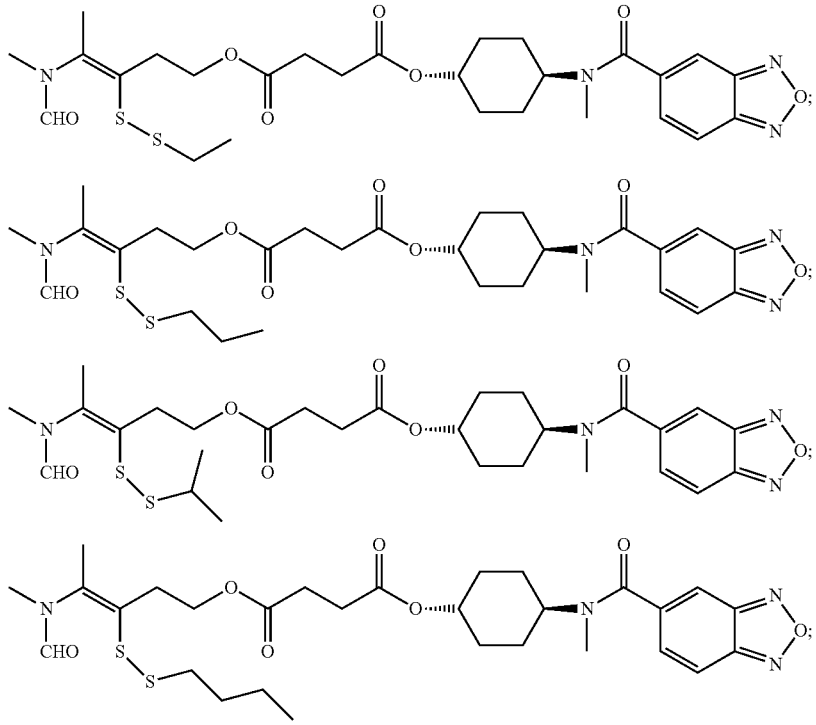

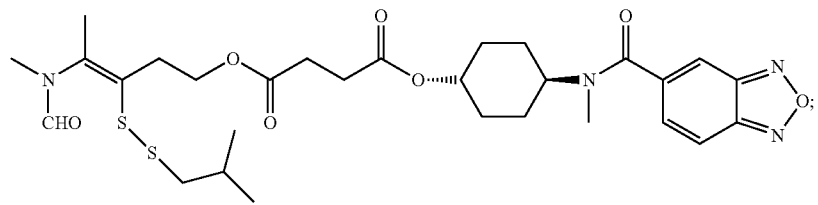
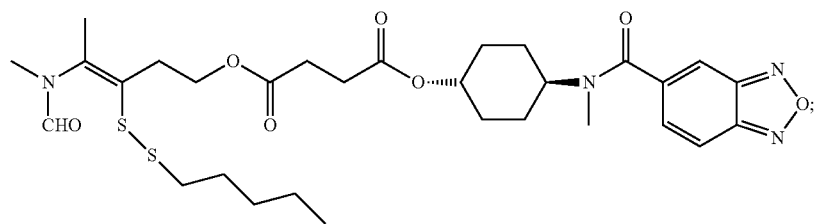
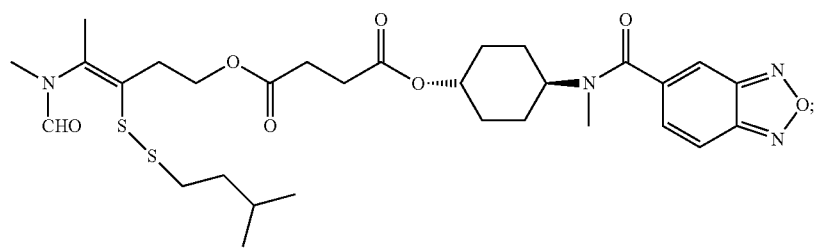
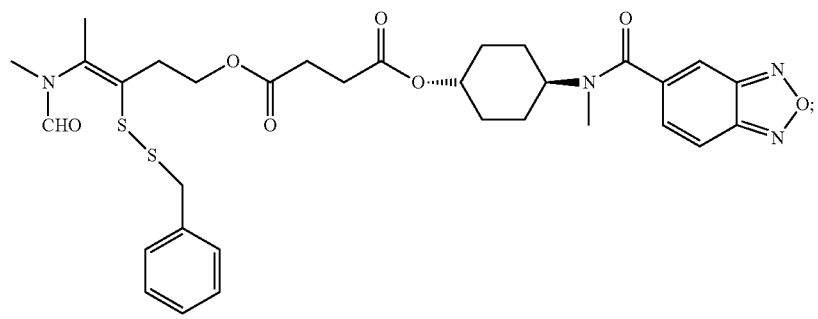
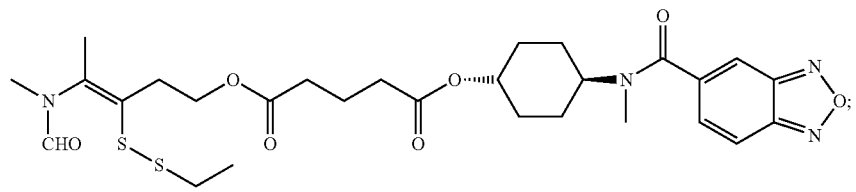
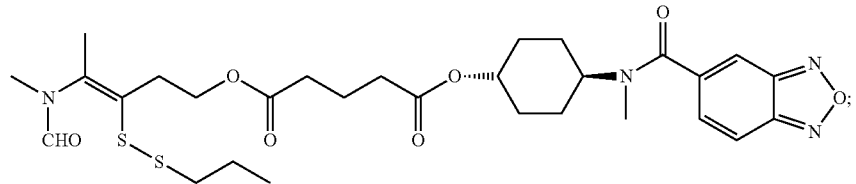
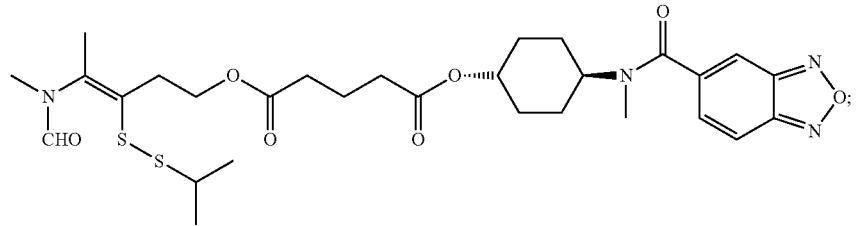

-continued
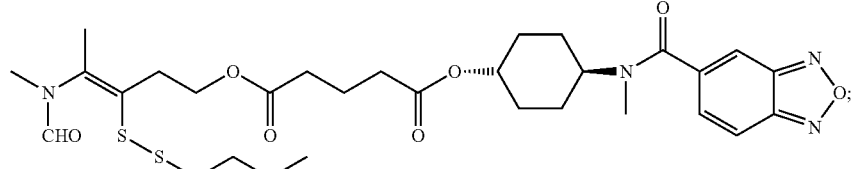
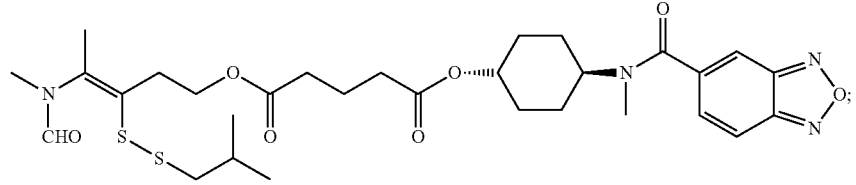
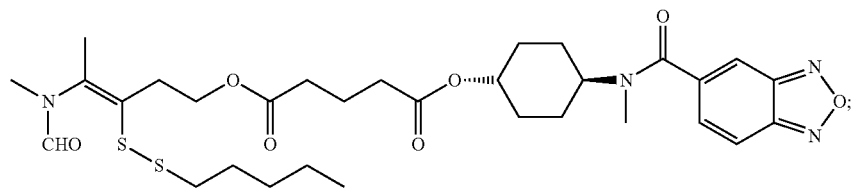
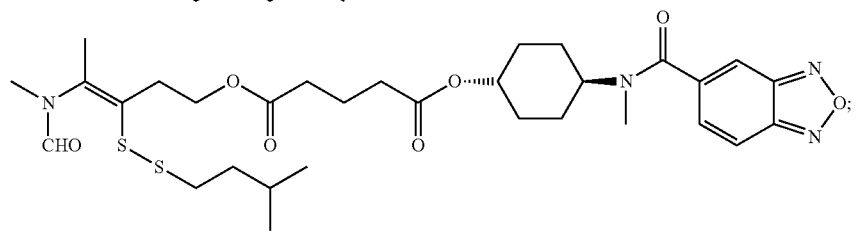
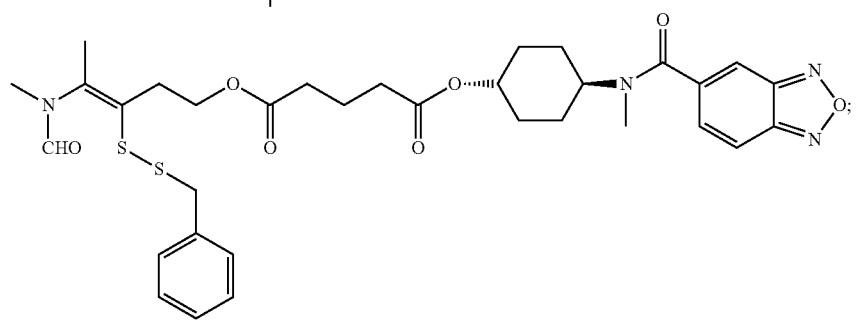
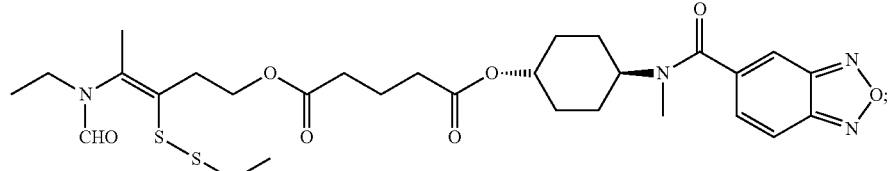
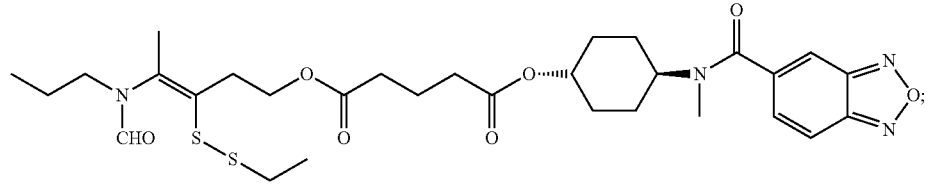
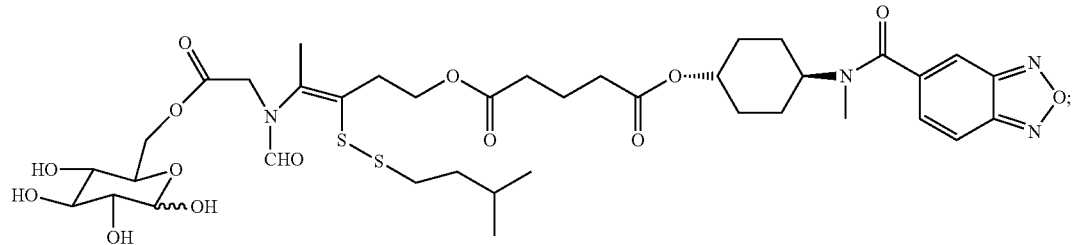

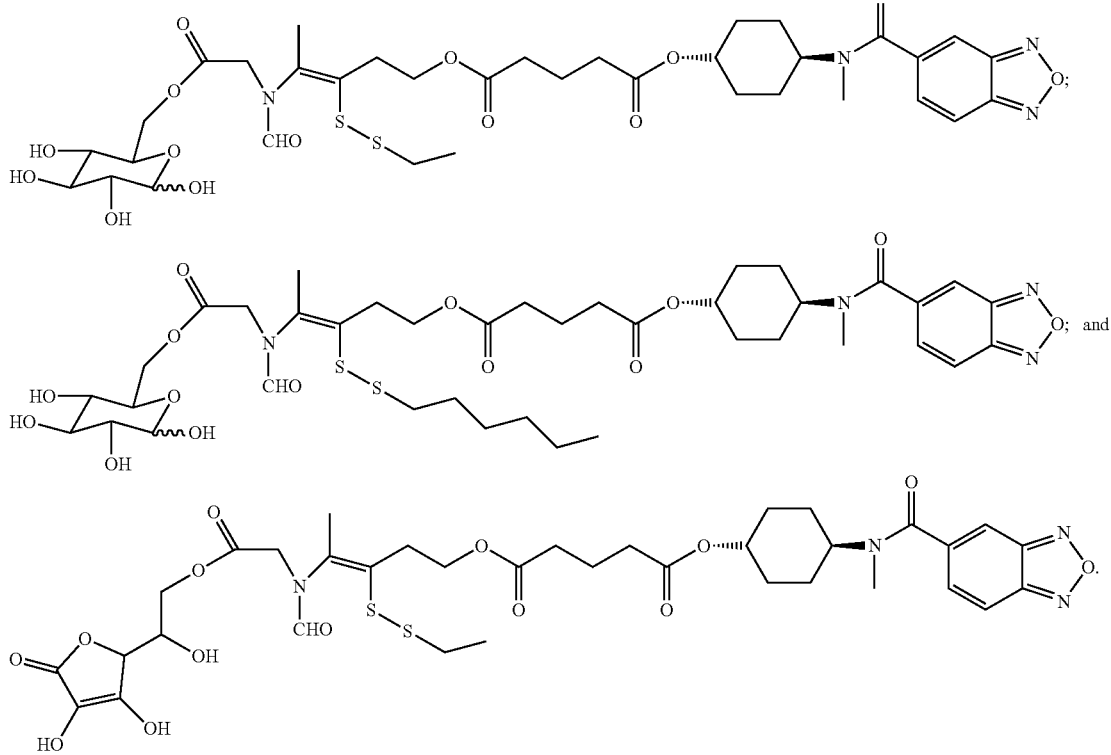

The present invention also relates to a pharmaceutical composition, comprising an effective amount of the compound of Formula (I), the geometric or optical isomer, the pharmaceutically acceptable salt, the solvate or the polymorph thereof in any one of the aforesaid embodiments, and one or more pharmaceutically acceptable carriers, additives or excipients, preferably, the compound accounts for about 0.5-75 wt % of the composition, and the carriers, additives or excipients account for about 25-95.5 wt % of the composition.

The present invention further relates to a method for treating a disease or disorder or for alleviating the severity of the disease or disorder, comprising administering to a patient in need of such treatment a therapeutically effective amount of at least one of the compound of Formula (I), the geometric or optical isomer, the pharmaceutically acceptable salt, the solvate or the polymorph thereof.

The present invention further relates to use of the compound of Formula (I), the geometric or optical isomer, the pharmaceutically acceptable salt, the solvate or the polymorph thereof in any one of the aforesaid embodiments of the present invention, in the manufacture of a medicament for the treatment of a disease or disorder or for the alleviation of the severity of the disease or disorder.

The present invention further relates to the compound of Formula (I), the geometric or optical isomer, the pharmaceutically acceptable salt, the solvate or the polymorph thereof in any one of the aforesaid embodiments of the present invention, for use in the treatment a disease or disorder or in the alleviation of the severity of the disease or disorder.

In an embodiment of the present invention, the disease or disorder of the present invention is selected from the group consisting of a hypoglutamatergic condition, impaired memory or other cognitive functions caused by a deficiency in the number or strength of excitatory synapses, or a deficiency in the number of DL-α-amino-3-hydroxy-5-methyl-4-isoxazolyl propionic acid (AMPA) receptors, schizophrenia or schizophreniform behavior caused by a cortical/striatal imbalance due to a deficiency in the number or strength of excitatory synapses, or a deficiency in the number of DL-α-amino-3-hydroxy-5-methyl-4-isoxazolyl propionic acid (AMPA) receptors, attention deficit hyperactivity disorder, Rett syndrome, fragile-X syndrome, respiratory depression, breathing-related sleep disorders or sleep apnea, Alzheimer's disease, schizophrenia or Parkinson's disease.

The present invention further relates to a method for treating respiratory depression in a patient in need of such treatment, the method comprising administering to the patient an effective amount of the compound of Formula (I), the geometric or optical isomer, the pharmaceutically acceptable salt, the solvate or the polymorph thereof in any one of the aforesaid embodiments of the present application, in combination with an opiate or an opioid analgesic, or the method comprising administering to the patient an effective amount of the compound of Formula (I), the geometric or optical isomer, the pharmaceutically acceptable salt, the solvate or the polymorph thereof in any one of the aforesaid embodiments of the present application, in combination with an anesthetic. The anesthetic is, for example, propofol or a barbiturate salt.

The present invention further relates to a method for treating Alzheimer's disease in a patient in need of such treatment, the method comprising administering to the patient an effective amount of the compound of Formula (I), the geometric or optical isomer, the pharmaceutically acceptable salt, the solvate or the polymorph thereof in any one of the aforesaid embodiments of the present invention, in combination with an acetylcholinesterase inhibitor.

The present invention further relates to use of the compound of Formula (I), the geometric or optical isomer, the pharmaceutically acceptable salt, the solvate or the polymorph thereof in any one of the aforesaid embodiments, in combination with one or more drugs selected from the group consisting of opiates, opioid analgesics and anesthetics, in the manufacture of a medicament for the treatment of respiratory depression.

The present invention further relates to the compound of Formula (I), the geometric or optical isomer, the pharmaceutically acceptable salt, the solvate or the polymorph thereof in any one of the aforesaid embodiments, in combination with one or more drugs selected from the group consisting of opiates, opioid analgesics and anesthetics, for use in the treatment of respiratory depression.

The present invention further relates to use of the compound of Formula (I), optical isomer, the pharmaceutically acceptable salt, the solvate or the polymorph thereof in any one of the aforesaid embodiments, in combination with an acetylcholinesterase inhibitor, in the manufacture of a medicament for the treatment of Alzheimer's disease.

The present invention further relates to the compound of Formula (I), the geometric or optical isomer, the pharmaceutically acceptable salt, the solvate or the polymorph thereof according to any one of the aforesaid embodiments, in combination with an acetylcholinesterase inhibitor, for use in the treatment of Alzheimer's disease.

The present invention further relates to a method for the treatment of a mammalian subject suffering from a hypoglutamatergic condition, or impairment of memory or other cognitive functions caused by a deficiency in the number or strength of excitatory synapses, or a deficiency in the number of AMPA receptors, comprising administering the subject an effective amount of the compound of Formula (I), the geometric or optical isomer, the pharmaceutically acceptable salt, the solvate or the polymorph thereof in any one of the aforesaid embodiments of the present invention, in a pharmaceutically acceptable carrier.

The present invention further relates to a method for the treatment of a mammalian subject suffering from a hypoglutamatergic condition, or schizophrenia or schizophreniform behavior resulted from the imbalance of cortical/striatal due to a deficiency in the number or strength of excitatory synapses, or a deficiency in the number of AMPA receptors, wherein the method comprises administering the subject an effective amount of the compound of Formula (I), the geometric or optical isomer, the pharmaceutically acceptable salt, the solvate or the polymorph thereof in any one of the aforesaid embodiments of the present invention, in a pharmaceutically acceptable carrier.

In an embodiment of the present invention, the hypoglutamatergic condition is schizophrenia.

In an embodiment of the present invention, the hypoglutamatergic condition is Parkinson's disease.

The present invention further relates to a method for treating attention deficit hyperactivity disorder in a patient in need of such treatment, the method comprises administering to the patient an effective amount of the compound of Formula (I), the geometric or optical isomer, the pharmaceutically acceptable salt, the solvate or the polymorph thereof in any one of the aforesaid embodiments of the present application.

The present invention further relates to a method of treating Rett syndrome in a patient in need of such treatment, comprising administering to the patient an effective amount of the compound of Formula (I), the geometric or optical isomer, the pharmaceutically acceptable salt, the solvate or the polymorph thereof in any one of the aforesaid embodiments of the present application.

The present invention further relates to a method of treating fragile-X syndrome in a patient in need of such treatment, comprising administering to the patient an effective amount of the compound of Formula (I), the geometric or optical isomer, the pharmaceutically acceptable salt, the solvate or the polymorph thereof in any one of the aforesaid embodiments of the present application.

The present invention further relates to a method for treating respiratory depression in a patient in need of such treatment, comprising administering to the patient an effective amount of the compound of Formula (I), the geometric or optical isomer, the pharmaceutically acceptable salt, the solvate or the polymorph thereof in any one of the aforesaid embodiments of the present application.

The present invention further relates to a method for treating a mammalian subject suffering from a hypoglutamatergic condition, or deficiencies in the number or strength of excitatory synapses or in the number of AMPA receptors. In such a subject, memory or other cognitive functions may be impaired, or a cortical/striatal imbalance may occur, leading to loss of memory, dementia, depression, attention disorders, sexual dysfunction, movement disorders, schizophrenia or schizophreniform behavior. The treatable memory disorder and learning disorder in the present invention include disorders result from, for example, aging, trauma, stroke and neurodegenerative disorders. Examples of neurodegenerative disorders include, but are not limited to, those associated with drug-induced states, neurotoxic agents, Alzheimer's disease, and aging. These conditions are readily recognized and diagnosed by those of ordinary skill in the art and treated by administering to the patient an effective amount of one or more compounds of the present invention.

In another aspect, the present invention relates to a method for alleviating or inhibiting respiratory depression in a subject having such a condition, comprising administering to the subject a certain amount of a compound of the present invention, wherein the amount is sufficient to alleviate or inhibit respiratory depression. In a further aspect of the present invention, related is a method for alleviating or inhibiting respiratory depression, comprising administering to the subject a certain amount of a compound of the present invention in combination with an opiate; examples of such opiates include but are not limited to, alfentanil and fentanyl.

In a further aspect, the present invention relates to a method for alleviating or inhibiting a breathing-related sleep disorder or sleep apnea in a subject having sleep apnea, comprising administering to the subject a certain amount of a compound of the present invention, wherein the amount is sufficient to alleviate or inhibit the breathing related sleep disorder.

The present invention further relates to a method of treating respiratory depression in a patient in need of such treatment, comprising administering to the patient an effective amount of the compound of Formula (I), the geometric or optical isomer, the pharmaceutically acceptable salt, the solvate or the polymorph thereof in any one of the aforesaid embodiments of the present application, in combination with an opiate or an opioid analgesic.

The present invention further relates to a method for treating respiratory depression in a patient in need of such treatment, comprising administering to the patient an effective amount of the compound of Formula (I), the geometric or optical isomer, the pharmaceutically acceptable salt, the solvate or the polymorph thereof in any one of the aforesaid embodiments of the present application, in combination with an anesthetic, wherein the anesthetic is, for example, propofol or a barbiturate salt.

The present invention further relates to a method for treating breathing-related sleep disorders or sleep apnea in a patient in need of such treatment, comprising administering to the patient an effective amount of the compound of Formula (I), the geometric or optical isomer, the pharmaceutically acceptable salt, the solvate or the polymorph thereof in any one of the aforesaid embodiments of the present application.

The present invention further relates to a method for treating Alzheimer's disease in a patient in need of such treatment, the method comprising administering to the patient an effective amount of the compound of Formula (I), the geometric or optical isomer, the pharmaceutically acceptable salt, the solvate or the polymorph thereof in any one of the aforesaid embodiments of the present application.

The present invention further relates to a method for treating Alzheimer's disease in a patient in need of such treatment, the method comprising administering to the patient an effective amount of the compound of Formula (I), the geometric or optical isomer, the pharmaceutically acceptable salt, the solvate or the polymorph thereof in any one of the aforesaid embodiments of the present application, in combination with an acetylcholinesterase inhibitor.

The present invention further relates to use of the compound of Formula (I), the geometric or optical isomer, the pharmaceutically acceptable salt, the solvate or the polymorph thereof in any one of the aforesaid embodiments of the present application, in the manufacture of a medicament for the treatment of a mammalian subject suffering from a hypoglutamatergic condition, or impairment of memory or other cognitive functions caused by a deficiency in the number or strength of excitatory synapses, or a deficiency in the number of AMPA receptors.

The present invention further relates to use of the compound of Formula (I), the geometric or optical isomer, the pharmaceutically acceptable salt, the solvate or the polymorph thereof in any one of the aforesaid embodiments of the present application, in the manufacture of a medicament for the treatment of schizophrenia.

The present invention further relates to use of the compound of Formula (I), the geometric or optical isomer, the pharmaceutically acceptable salt, the solvate or the polymorph thereof in any one of the aforesaid embodiments of the present application, in the manufacture of a medicament for the treatment of Parkinson's disease.

The present invention further relates to use of the compound of Formula (I), the geometric or optical isomer, the pharmaceutically acceptable salt, the solvate or the polymorph thereof in any one of the aforesaid embodiments of the present application, in the manufacture of a medicament for the treatment of attention deficit hyperactivity disorder.

The present invention further relates to use of the compound of Formula (I), the geometric or optical isomer, the pharmaceutically acceptable salt, the solvate or the polymorph thereof in any one of the aforesaid embodiments of the present application, in the manufacture of a medicament for the treatment of Rett syndrome.

The present invention further relates to use of the compound of Formula (I), the geometric or optical isomer, the pharmaceutically acceptable salt, the solvate or the polymorph thereof in any one of the aforesaid embodiments of the present application, in the manufacture of a medicament for the treatment of a cognitive disorder.

The present invention further relates to use of the compound of Formula (I), the geometric or optical isomer, the pharmaceutically acceptable salt, the solvate or the polymorph thereof in any one of the aforesaid embodiments of the present application, in the manufacture of a medicament for the treatment of respiratory depression.

The present invention further relates to use of the compound of Formula (I), the geometric or optical isomer, the pharmaceutically acceptable salt, the solvate or the polymorph thereof in any one of the aforesaid embodiments of the present application, in combination with an opiate, in the manufacture of a medicament for the treatment of respiratory depression.

The present invention further relates to use of the compound of Formula (I), the geometric or optical isomer, the pharmaceutically acceptable salt, the solvate or the polymorph thereof in any one of the aforesaid embodiments of the present application, in the manufacture of a medicament for the treatment of breathing-related sleep disorders or sleep apnea.

The present invention further relates to use of the compound of Formula (I), the geometric or optical isomer, the pharmaceutically acceptable salt, the solvate or the polymorph thereof in any one of the aforesaid embodiments of the present application, in the manufacture of a medicament for the treatment of fragile-X syndrome.

The present invention further relates to use of the compound of Formula (I), the geometric or optical isomer, the pharmaceutically acceptable salt, the solvate or the polymorph thereof in any one of the aforesaid embodiments of the present application, in the manufacture of a medicament for the treatment of Alzheimer's disease.

The present invention further relates to the compound of Formula (I), the geometric or optical isomer, the pharmaceutically acceptable salt, the solvate or the polymorph thereof in any one of the aforesaid embodiments of the present application, for use in the treatment of a mammalian subject suffering from a hypoglutamatergic condition, or impairment of memory or other cognitive functions caused by a deficiency in the number or strength of excitatory synapses, or a deficiency in the number of AMPA receptors.

The present invention further relates to the compound of Formula (I), the geometric or optical isomer, the pharmaceutically acceptable salt, the solvate or the polymorph thereof in any one of the aforesaid embodiments of the present application, for use in the treatment of schizophrenia.

The present invention further relates to the compound of Formula (I), the geometric or optical isomer, the pharmaceutically acceptable salt, the solvate or the polymorph thereof in any one of the aforesaid embodiments of the present application, for use in the treatment of Parkinson's disease.

The present invention further relates to the compound of Formula (I), the geometric or optical isomer, the pharmaceutically acceptable salt, the solvate or the polymorph thereof in any one of the aforesaid embodiments of the present application, for use in the treatment of attention deficit hyperactivity disorder.

The present invention further relates to the compound of Formula (I), the geometric or optical isomer, the pharmaceutically acceptable salt, the solvate or the polymorph thereof in any one of the aforesaid embodiments of the present application, for use in the treatment of Rett syndrome.

The present invention further relates to the compound of Formula (I), the geometric or optical isomer, the pharmaceutically acceptable salt, the solvate or the polymorph thereof in any one of the aforesaid embodiments of the present application, for use in the treatment of a cognitive disorder.

The present invention further relates to the compound of Formula (I), the geometric or optical isomer, the pharmaceutically acceptable salt, the solvate or the polymorph thereof in any one of the aforesaid embodiments of the present application, for use in the treatment of respiratory depression.

The present invention further relates to the compound of Formula (I), the geometric or optical isomer, the pharmaceutically acceptable salt, the solvate or the polymorph thereof in any one of the aforesaid embodiments of the present application, for use in the treatment of breathing-related sleep disorders or sleep apnea.

The present invention further relates to the compound of Formula (I), the geometric or optical isomer, the pharmaceutically acceptable salt, the solvate or the polymorph thereof in any one of the aforesaid embodiments of the present application, for use in the treatment of fragile-X syndrome.

The present invention further relates to the compound of Formula (I), the geometric or optical isomer, the pharmaceutically acceptable salt, the solvate or the polymorph thereof in any one of the aforesaid embodiments of the present application, for use in the treatment of Alzheimer's disease.

The present invention further relates to a method for the preparation of the compound of Formula (I), the geometric or optical isomer, the pharmaceutically acceptable salt, the solvate or the polymorph thereof in any one of the aforesaid embodiments.

In an embodiment of the present invention, the preparation method comprises the following steps of:

a) reacting sodium thiosulfate with $R_2Br$ to give a compound of Formula (III);

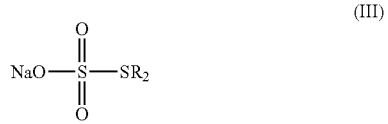

b) reacting 4-methyl-5-thiazoleethanol with $R_1I$ to give a compound of Formula (IV);

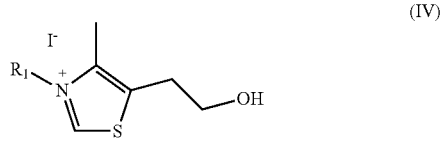

c) reacting a compound of the Formula (III) with a compound of the Formula (IV) to give a compound of Formula (V);

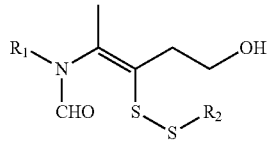

d) reacting a compound of Formula (V) with an acid anhydride represented by

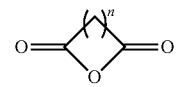

to give a compound of Formula (VI);

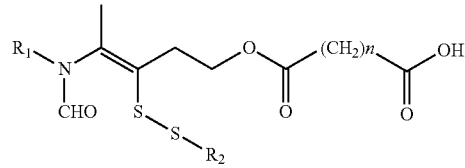

e) reacting a compound of Formula (VI) with N-(anti-4-hydroxycyclohexyl)-N-methylbenzo[c][1,2,5]oxadiazol-5-yl-carboxamide to obtain a compound of Formula (I), wherein: $R_1$ represents $C_1$—C linear or branched alkyl, and $R_2$ and n are as defined in the Formula (I).

In another embodiment of the present invention, the preparation method comprises the following steps of:

a) reacting sodium thiosulfate with $R_2Br$ to give a compound of Formula (III) for further use;

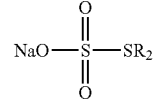

b) reacting 4-methyl-5-thiazoleethanol with a tert-butyl bromoacetate to give N-tert-butoxycarbonylmethyl-4-dimethyl-5-(2-(hydroxyl)ethyl)-thiazole bromide of Formula (VII);

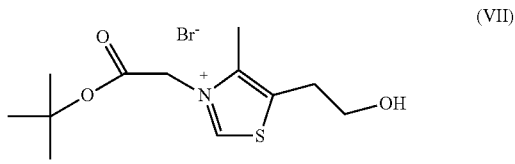

c) reacting a compound of Formula (III) with the compound of Formula (VII) to give a compound of Formula (VIII);

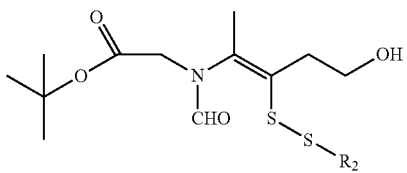

(VIII)

d) reacting a compound of Formula (VIII) with an acid anhydride represented by

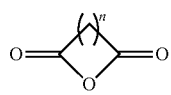

to give a compound of Formula (IX);

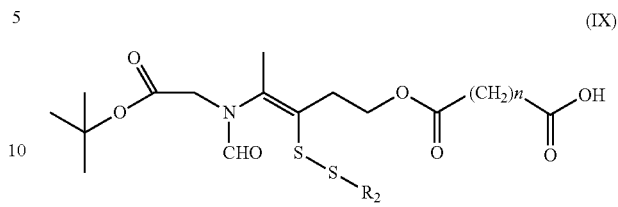

(IX)

e) reacting a compound of Formula (IX) with N-(anti-4-hydroxycyclohexyl)-N-methylbenzo[c][1,2,5]oxadiazol-5-yl-carboxamide to give a compound of Formula (X);

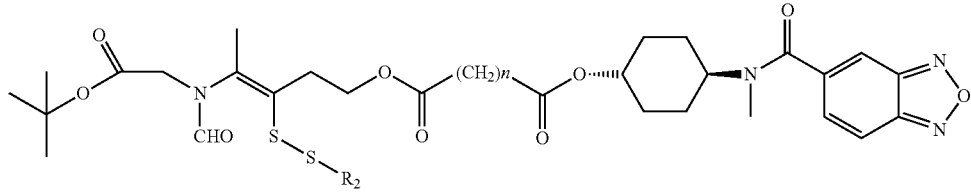

(X)

f) removing the tert-butoxyl from a compound of Formula (X) to give a compound of formula (XI);

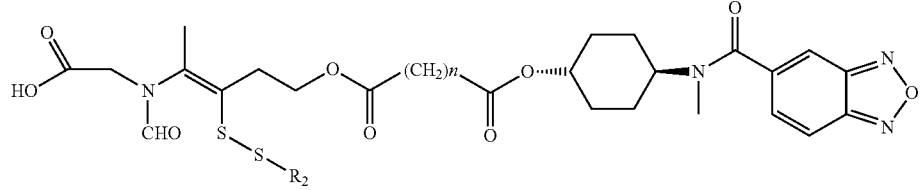

(XI)

g) reacting a compound of formula (XI) with an acetyl-protected glucose/L-ascorbic acid to give a compound of formula (XII);

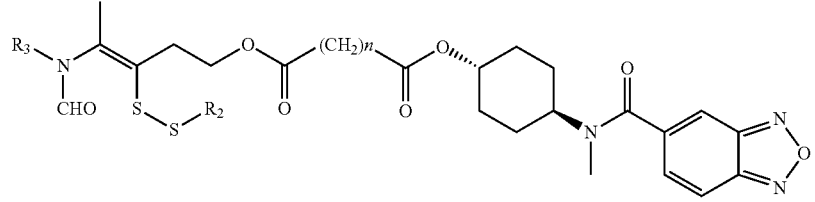

(XII)

h) removing the protecting group of acetyl from a compound of formula (XII) to give a compound of general Formula (I), wherein: $R_1$ represents

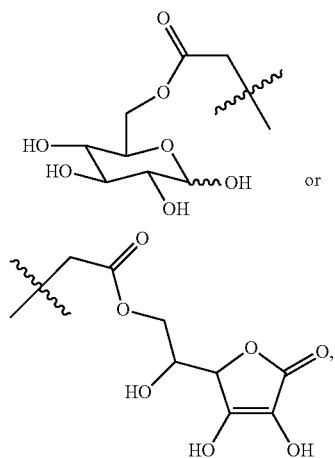 or $R_3$ represents

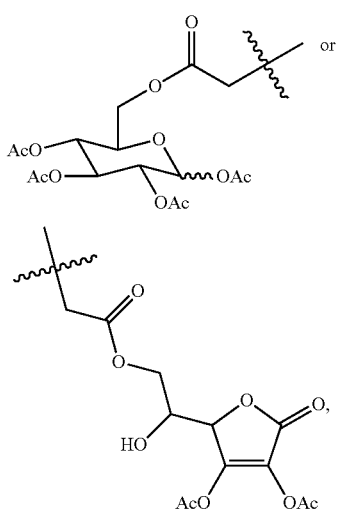 or $R_2$ and n are as defined in Formula (I).

In a preferred embodiment of the present invention, the preparation method comprises the following step:

a) sodium thiosulfate is mixed with $R_2Br$ in a mixed solvent, heated in an oil bath, and refluxed for 10 hours; and a compound of Formula (III) is obtained when the reaction is complete;

(III)

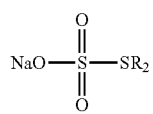

b) 4-methyl-5-thiazoleethanol is mixed with $R_1$, and heated to reflux; after 2 hours, the reaction is complete thereby obtaining a compound of Formula (IV);

(IV)

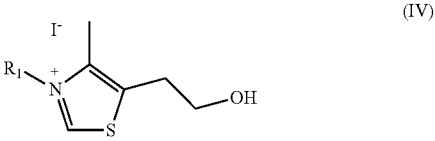

c) NaOH, a compound of Formula (III) and a compound of Formula (IV) are dissolved in water, and extracted with ethyl acetate; the organic solutions are combined, dried, filtered, and dried by rotary evaporation under reduced pressure to give a crude product; and the crude product is purified to give a compound of Formula (V) for further use;

(V)

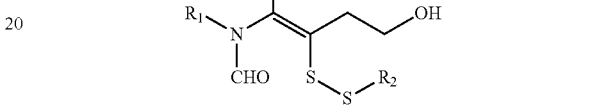

d) a compound of the Formula (V) and the acid anhydride of formula

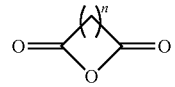

and N,N-dimethylaminopyridine are dissolved in anhydrous dichloromethane, and heated to reflux with stirring for 6 hours; the reaction liquid is washed with water; the organic phase is dried, filtered and dried by evaporation to give a compound of the Formula (VI) for further use;

(VI)

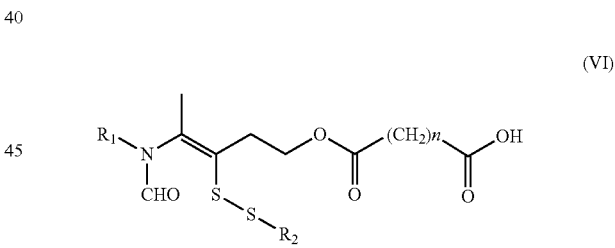

e) a compound of Formula (VI) and N-(anti-4-hydroxy-cyclohexyl)-N-methylbenzo[c][1,2,5]oxadiazol-5-yl-carboxamide, 4-dimethylamino-pyridine, 1-hydroxy-benzotriazole, triethylamine and 1-ethyl-3-(3-dimethylaminopropyl) carbodiimide hydrochloride are dissolved in dichloromethane, and heated under stirring to reflux for 5 hours; and the reaction solution is subjected to rotary drying, and chromatographed on a silica gel column to obtain a compound of Formula (I), wherein: $R_1$ represents $C_1$—C linear or branched alkyl, and $R_2$ and n are as defined in Formula (I).

In a preferred embodiment of the present invention, the preparation method comprises the following step:

a) sodium thiosulfate is mixed with RBr in a mixed solvent, heated in an oil bath, and refluxed for 10 hours; and a compound of Formula (III) is obtained when the reaction is complete;

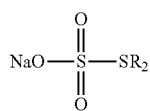
(III)

b) 4-methyl-5-thiazoleethanol and tert-butylbromoacetate are mixed and heated to reflux; after 1.5 hours, the reaction is completely completed to N-tert-butoxycarbonylethyl-4-methyl-5-[2-(hydroxyl)ethyl] thiazole bromide of formula (VII for use;

(VII)

c) NaOH, a compound of Formula (III) and a compound of Formula (VII) are dissolved in water, and extracted with ethyl acetate; the organic solutions are combined, dried, filtered, and subjected to rotary drying under reduced pressure to give a crude product; and the crude product is purified to give a compound of Formula (VIII) for use;

(VIII)
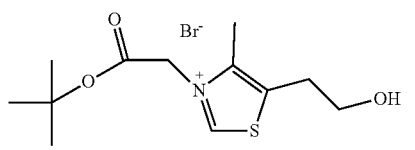

d) a compound of the Formula (VIII) and the acid anhydride of formula

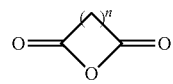

and N,N-dimethylaminopyridine are dissolved in anhydrous dichloromethane, and heated under stirring to reflux for 6 hours; the reaction liquid is washed with water; the organic phase is dried, filtered and evaporated to dry to give a compound of the Formula (IX) for use (IX)

e) a compound of Formula (IX) and N-(anti-4-hydroxy-cyclohexyl)-N-methylbenzo[c][1,2,5]oxadiazol-5-yl-carboxamide, 4-dimethylamino-pyridine, 1-hydroxy-benzotriazole, triethylamine, 1-ethyl-3-(3-dimethylaminopropyl) carbodiimide hydrochloride are dissolved in dichloromethane, and heated under stirring to reflux for 5 hours; and the reaction solution is subjected to rotary drying, and chromatographed on a silica gel column to obtain a compound of Formula (X);

(X)

f) a compound of Formula (X) is dissolved in dichloromethane, then 70% perchloric acid is added dropwise to the solution, stirred at room temperature for 6 h, and sodium hydrogencarbonate solid is added to the solution to adjust the pH to neutral; after filtration, the filtrate is mixed with silica gels, and on a silica gel column to obtain a compound of formula (XI);

(XI)
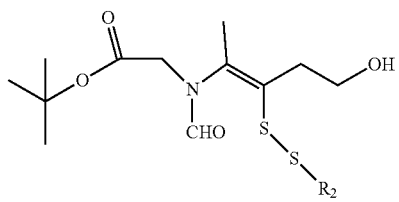

g) a compound of formula (XI), an acetyl-protected glucose/L-ascorbic acid, 4-dimethylamino-pyridine and 1-hydroxy-benzotriazole are dissolved in a mixed solvent of anhydrous N,N-dimethylformamide/anhydrous dichloromethane mixed solvent, stirred at room temperature, and after 30 minutes, N,N-dicyclohexyl carbodiimine; the mixture is stirred at room temperature overnight and filtered; and the filtrate is subjected to rotary drying, and chromatographed on a silica gel column to obtain a compound of formula (XII)

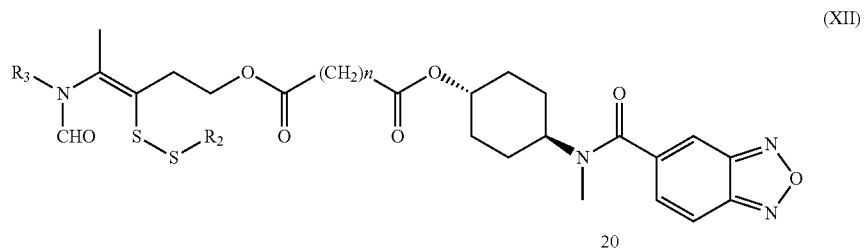

(XII)

h) a compound of formula (XII) is dissolved in methanol, solid sodium carbonate is added to the solution at 0° C., and reaction is carried out in an ice bath for 2 hours; the reaction solution is filtered; the filtrate is subjected to rotary drying, and chromatographed on a silica gel column to obtain a compound of Formula (I), wherein: $R_1$ represents $R_3$ represents

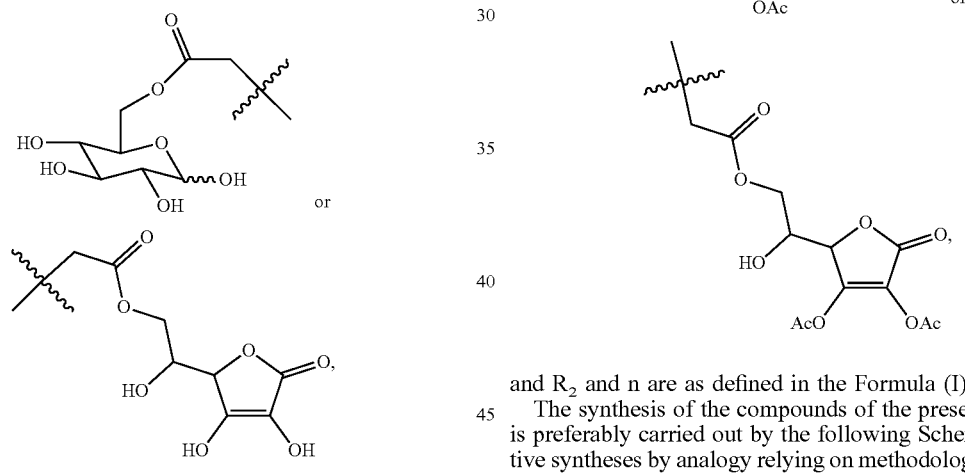

and $R_2$ and n are as defined in the Formula (I).

The synthesis of the compounds of the present invention is preferably carried out by the following Scheme. Alternative syntheses by analogy relying on methodology that exists in the art also may be used.

Synthetic Route 1:

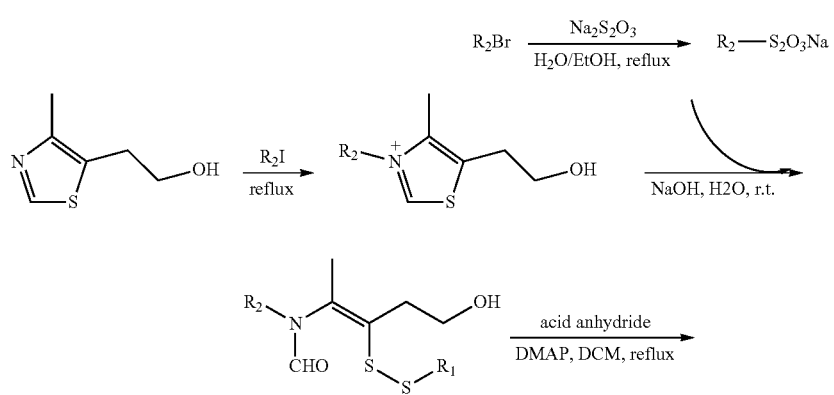

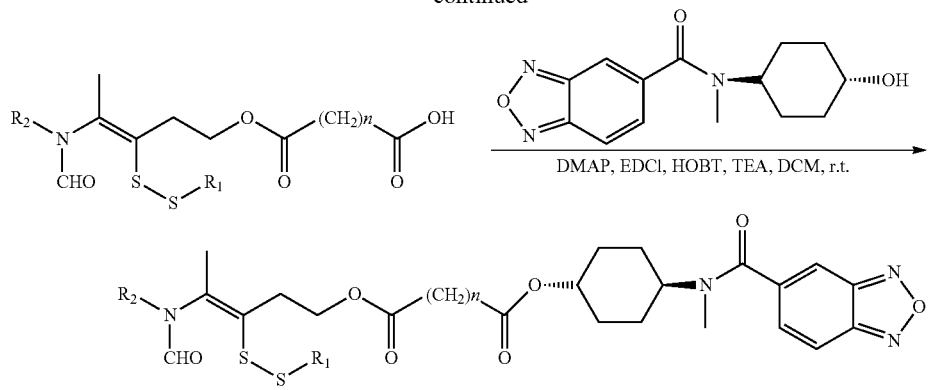
R$_1$ represents C$_1$-C$_5$ branched or non-branched alkyl;
R$_2$ represents C$_1$-C$_{10}$ branched or non-branched alkyl;
n represents 1-5.
Synthetic 2:
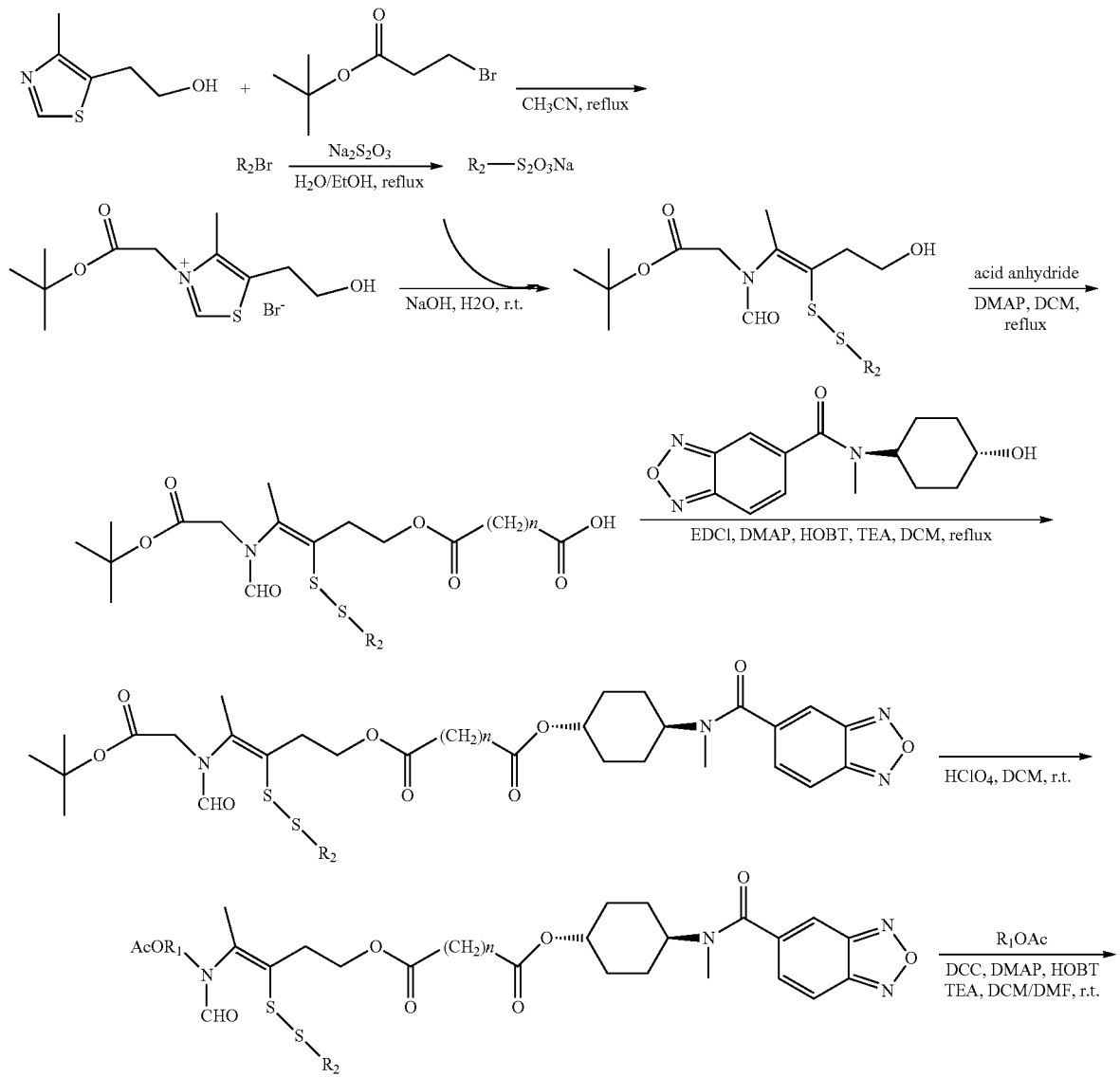

-continued

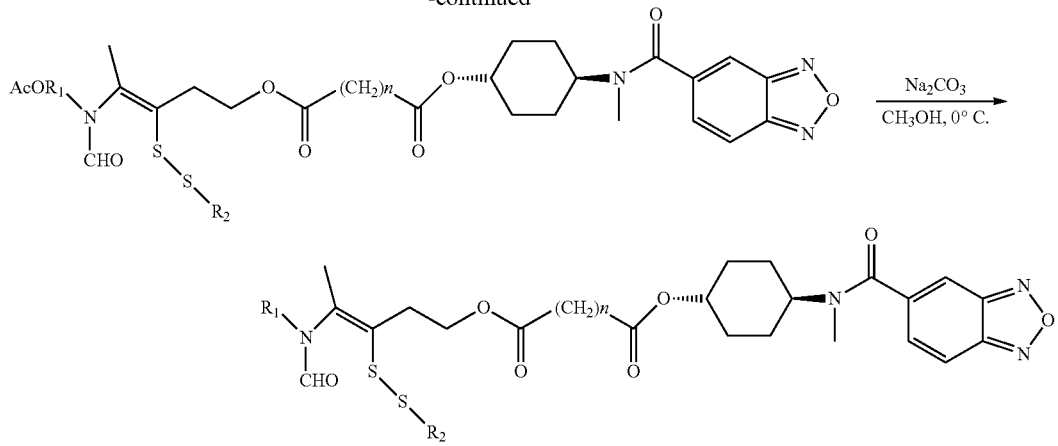

wherein, $R_1$ represents

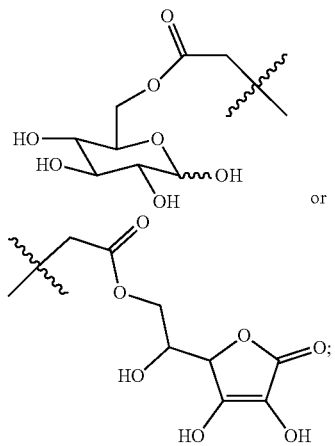

$R_2$ represents $C_1$-$C_{10}$ branched or non-branched alkyl;
n represents 1-5.

In the synthetic route 1, 4-methyl-5-thiazoleethanol is firstly alkylated with an iodoalkane, then subjected to a ring-opening reaction with sodium hydroxide and sodium alkylthiosulfate, the hydroxyl group is reacted with an acid anhydride to form an acid, and the acid is reacted with the AMPA receptor synergist, N-(anti-4-hydroxycyclohexyl)-N-methylbenzo[c][1,2,5]oxadiazol-5-yl-carboxamide (code: Compound a) under the action of a condensing agent (e.g., 1-ethyl-3-(3-dimethylaminopropyl) carbodiimide hydrochloride) to obtain a target compound.

In the synthetic route 2, 4-methyl-5-thiazoleethanol is firstly reacted with tert-butyl-3-bromopropionic acid to form a salt, then subjected to a ring-opening reaction in the presence of sodium hydroxide and sodium alkylthiosulfate, and the intermediate obtained after the ring-opening reaction is reacted with an acid anhydride to form an acid in the presence of a catalyst (4-dimethylaminopyridine); the acid is condensed with the AMPA receptor synergist under the action of a condensing agent (e.g., 1-ethyl-3-(3-dimethylaminopropyl) carbodiimide hydrochloride); the tert-butyl is removed from the condensation product in the presence of perchloric acid to expose the acid group; the acid is condensed with an acetyl-protected glucose/L-ascorbic acid in the presence of a condensing agent (e.g., N,N-dicyclohexyl carbodiimine); and the acetyl group is removed from the condensation product by sodium carbonate to obtain a target product.

A compound of Formula (I) as described above can be converted into a pharmaceutically acceptable solvate thereof.

Some compounds of formula I can exist in stereoisomeric forms. It will be understood that the present invention also encompasses all geometric and optical isomers and mixtures thereof including racemates. Tautomers and mixtures thereof also constitute an aspect of the present invention.

Definitions

The term "$C_1$-$C_{10}$ linear or branched alkyl" used herein refers to a linear or branched alkyl having 1-10 carbon atoms, for example, $C_1$-$C_8$ linear or branched alkyl, $C_1$-$C_6$ linear or branched alkyl, $C_1$-$C_4$ linear or branched alkyl, $C_1$-$C_3$ linear or branched alkyl. Particular examples include, but are not limited to: methyl, ethyl, propyl, iso-propyl, n-butyl, sec-butyl, tert-butyl, iso-butyl, n-pentyl, 3-methyl-butyl, 2-methyl-butyl, 1-methyl-butyl, 2,2-dimethyl-propyl, 1,1-dimethyl-propyl, 1,2-dimethyl-propyl, 1-ethyl-propyl, n-hexyl, 1-methyl-n-pentyl, 2-methyl-pentyl, 3-methyl-pentyl, 4-methyl-pentyl, 1,1-dimethyl-butyl, 2,2-dimethyl-butyl, 3,3-dimethyl-butyl, 1,2-dimethyl-butyl, 1,3-dimethyl-butyl, 2,3-dimethyl-butyl, 1-ethyl-butyl, 2-ethyl-butyl, 1,2,2-trimethyl-propyl, 1,1,2-trimethyl-propyl, and the like.

The term "$C_1$-$C_5$ linear or branched alkyl" used herein refers to a linear or branched alkyl having 1-5 carbon atoms, for example, $C_1$-$C_4$ linear or branched alkyl, $C_1$-$C_3$ linear or branched alkyl. Particular examples include, but are not limited to: methyl, ethyl, propyl, iso-propyl, n-butyl, sec-butyl, tert-butyl, iso-butyl, n-pentyl, 3-methyl-butyl, 2-methyl-butyl, 1-methyl-butyl, 2,2-dimethyl-propyl, 1,1-dimethyl-propyl, 1,2-dimethyl-propyl, 1-ethyl-propyl, and the like.

The term "phenyl-$C_1$-$C_4$ alkyl" used herein refers to $C_1$-$C_4$ alkyl as defined above which is substituted by phenyl, for example, phenyl-$C_1$-$C_3$ alkyl. Particular examples include, but are not limited to: benzyl, phenylethyl, phenylpropyl, phenylbutyl, and the like.

The term "compound" used herein refers to any specific compound disclosed herein. For the use as mentioned in the context, the term generally refers to a single compound, but in certain instances may also refer to stereoisomers and/or optical isomers (including enantiopure compounds, enantiomerically enriched compounds and racemic mixtures) of the disclosed compounds.

The term "effective amount" refers to the amount of a selected compound of formula I, for an intended use as mentioned in the context, the amount is sufficient to achieve the intended result, for example, to enhance glutamatergic synaptic response by increasing AMPA receptor activity. The precise amount used will vary depending upon the particular compound selected and its intended use, the age and weight of the subject, route of administration, and so forth, including the duration of its efficacy, but may be easily determined by routine experimentation. In the case of the treatment of a disorder or disease state, an effective amount is the amount that is effectively treat the the disorder or disease state.

The term "pharmaceutically acceptable carrier" refers to a carrier or excipient without unacceptably toxicity to the subject being administered. Pharmaceutically acceptable excipients are described at length by E. W. Martin, in "Remington's Pharmaceutical Sciences."

A "pharmaceutically acceptable salt" of an amine compound, such as an intended amine compound in the present invention, is an ammonium salt having an inorganic anion or an organic anion as counter ion, wherein an exemplary inorganic anion is chloride, bromide, iodide, sulfate, sulfite, nitrate, nitrite, phosphate, and the like, and an exemplary organic anion is acetate, malonate, pyruvate, propionate, fumarate, cinnamate, tosylate, and the like.

The term "patient" or "subject" used throughout the specification is to define an animal, generally a mammalian animal, including a human, which is treated or administered with the compound or composition according to the present invention. For the treatment of or use in a particular disorder or disease state for a particular animal (especially, for example, a human subject or patient), the term patient or subject refers to the particular animal.

The term "sensorimotor problem" is used to describe a problem which arises in a patient or a subject for the inability to make appropriate physical response involving movement and action according to the integration of external information derived from the five known senses.

The term "cognitive task" or "cognitive function" is used to describe an endeavor or process by a patient or a subject that involves thought or knowing. The diverse functions of the association cortices of the parietal, temporal and frontal lobes, which account for approximately 75% of all human brain tissue, are responsible for lots of the information processing that goes on between sensory input and motor output. The diverse functions of the association cortices are often referred to as cognition, which literally means the process we come to know the world. Selectively attending to a particular stimulus, recognizing and identifying these relevant stimulus features and planning and experiencing the response are some of the processes or abilities related to cognition mediated by the human brain.

The term "brain network" is used to describe different anatomical regions of the brain, which communicates with one another via the synaptic activity of neuronal cells.

The term "AMPA receptor" refers to an aggregate of proteins found in some membranes, the receptor allows positive ions to cross the membrane in response to the binding of glutamate or AMPA (DL-α-amino-3-hydroxy-5-methyl-4-isoxazolepropionic acid), but not NMDA.

The term "excitatory synapse" is used to describe a cell-cell junction, at which the release of a chemical messenger by one cell causes depolarization of the external membrane of the other cell. An excitatory synapse describes a postsynaptic neuron having a reversal potential which is more positive than the threshold potential.

Consequently, in such a synapse, a neurotransmitter increases the probability to generate an excitatory postsynaptic potential (to trigger a neuron generate an action potential). The reversal potential and threshold potential determine postsynaptic excitation and inhibition. If the threshold of the reversal potential for a post synaptic potential ("PSP") is more positive than that of the action potential, the transmitter is excitatory and generate an excitatory postsynaptic potential ("EPSP") and the neuron triggers an action potential. If the threshold of the reversal potential for a post synaptic potential is more negative than that of the action potential, the transmitter is inhibitory and may generate inhibitory postsynaptic potentials (IPSP), thus reducing the likelihood of the trigger of an action potential. The general rule for postsynaptic action is: if the reversal potential is more positive than the threshold potential, an excitation result generates; an inhibition result occurs if the reversal potential is more negative than the threshold potential. Please refer to, for example, Chapter 7, NEUROSCIENCE, edited by Dale Purves, Sinauer Associates, Inc., Sunderland, Mass. 1997.

The term "motor task" is used to describe an endeavor of a patient or subject that involves movement or action.

The term "perceptual task" is used to describe an act of a patient or subject who devotes attention to sensory inputs.

The term "synaptic response" is used to describe a biophysical reaction in one cell as a consequence of the release of a chemical messenger by another cell with which the cell is in close contact.

The term "hypoglutamatergic condition" is used to describe a state or disease in which transmission mediated by glutamate (or related excitatory amino acids) is reduced to below normal levels. The transmission comprises the release of glutamate, binding to postsynaptic receptors, and the opening of channels integral to those receptors. The end point of the hypoglutamatergic condition is the decrease of the excitatory postsynaptic current, which can arise from any of the three above noted phases of transmission. Disorder or disease which is considered as a hypoglutamatergic condition and can be treated by using the compound, composition and method according to the present invention include, for example, loss of memory, dementia, depression, attention disorder, sexual dysfunction, movement disorder, including Parkinson's disease, schizophrenia or schizophreniform behavior, memory and learning disorder, including disorders resulted from aging, trauma, stroke and neurodegenerative disorder, such as those associated with drug-induced disorder, neurotoxic agent, Alzheimer's disease and aging, respiratory depression and sleep apnea. The disease may be readily recognized and diagnosed by those of ordinary skill in the art.

The term "cortico-striatal imbalance" is used to describe a disorder in which the balance of neuronal activities in the interconnected cortex and underlying striatal complex deviates from that normally found. 'Activity' can be assessed by electrical recording or molecular biological techniques. Imbalance can be established by applying these measures to the two structures or by functional (behavioral or physiological) criteria.

The term "affective disorder" or "mood disorder" describes the disorder when sadness or elation is overly intense and continues beyond the expected impact of a stressful life event, or arises endogenously. As used herein, the term "effective disorder" embraces all types of mood disorders as described in, for example, Diagnostic and Statistical Manual of Mental Disorders, Fourth Edition (DSM IV), pages 317-391.

The term "schizophrenia" is used to describe a condition which is a common type of psychosis, characterized by a disorder in the thinking processes, such as delusions and hallucinations, and serious withdrawal of an individual's interest from other people and the outside world, and only focus on his or her own. Schizophrenia is now considered a group of mental disorders rather than a single entity, and distinction is made between reactive and process schizophrenias. As used herein, the term schizophrenia or "schizophreniform" embraces all types of schizophrenia, including ambulatory schizophrenia, catatonic schizophrenia, hebephrenic schizophrenia, latent schizophrenia, process schizophrenia, pseudoneurotic schizophrenia, reactive schizophrenia, simple schizophrenia, and related psychotic disorder which is similar to schizophrenia, but not necessarily diagnosed as schizophrenia per se. Schizophrenia and other psychotic disorders may be diagnosed using guidelines established in, for example, Diagnostic and Statistical Manual of Mental Disorders, Fourth Edition (DSM IV) Sections 293.81, 293.82, 295.10, 295.20, 295.30, 295.40, 295.60, 295.70, 295.90, 297.1, 297.3, 298.8.

The term "brain function" is used to describe the combined task of perceiving, integrating, filtering and responding to external stimuli and internal motivational processes.

The term "impaired" is used to describe a function working below normal level. An impaired function can be significantly impacted so that it is barely carried out, is virtually non-existent or is working significantly below normal. An impaired function may also be sub-optimal. The impaired function will vary depending on the severity of the patient and the disease to be treated.

The term "respiratory depression" as used herein refers to a variety of diseases characterized by reduced respiratory frequency and inspiratory drive to cranial and spinal motor neurons. Specifically, respiratory depression refers to the medullary neural network associated with respiratory rhythm generating activity does not respond to accumulating levels of $PCO_2$ (or decreasing levels of $PO_2$) in the blood and subsequently under stimulates motorneurons controlling lung musculature.

The term "sleep apnea" as used herein refers to a breathing-related sleep disorder. There are two types: central and obstructive sleep apnea. Central Sleep Apnea is defined as a neurological condition causing cessation of all respiratory effort during sleep, usually with decreases in blood oxygen saturation, if the brainstem center controlling breathing shuts down there's no respiratory effort and no breathing. The person is aroused from sleep by an automatic breathing reflex, so may end up getting very little sleep at all. Obstructive sleep apnea is characterized by repetitive pauses in breathing during sleep due to the obstruction and/or collapse of the upper airway and followed by an awakening to breathe. Respiratory effort continues during the episodes of apnea.

The term "co-administration" or "combination therapy" is used to describe a therapy in which at least two active compounds in effective amounts are used to treat a disease state or disorder as otherwise described herein at the same time. Although the term co-administration preferably includes the administration of two active compounds to the patient at the same time, it is not necessary that the compounds are administered to the patient at the same time, so long as the effective amounts of the individual compounds will be present in the patient at the same time.

Administration, Dosages, and Formulations

As noted above, the compound and method of the present invention increase glutamatergic synaptic response mediated by an AMPA receptor, and are useful for the treatment of hypoglutamatergic condition. They are also useful for the treatment of a condition such as impairment of memory or other cognitive function, brought on by a deficiency in the number or strength of excitatory synapses, or in the number of AMPA receptors. They may also be used in the treatment of schizophrenia or schizophreniform behavior resulting from a cortical/striatal imbalance, and in facilitation of learning behaviors dependent upon AMPA receptors.

In subjects treated with the present compound, pharmaceutical composition and method, memory or other cognitive function may be impaired or cortical/striatal imbalance may occur, leading to loss of memory, dementia, depression, attention disorder, sexual dysfunction, movement disorder, schizophrenia or schizophreniform behavior. Memory disorder and learning disorder, which are treatable in the present invention, include those disorders that result from aging, trauma, stroke and neurodegenerative disorder. Examples of neurodegenerative disorder include, but are not limited to, those associated with drug-induced state, neurotoxic agent, Alzheimer's disease, and aging. These disorders are readily recognized and diagnosed by those of ordinary skill in the art and treated by administering to the patient an effective amount of one or more compounds according to the present invention.

Generally, dosages and routes of administration of the compound will be determined according to the size and condition of the subject, according to standard pharmaceutical practices. Dose levels employed can vary widely, and can readily be determined by those of skill in the art. Typically, amounts in the milligram up to gram quantities are employed. The composition may be administered to a subject by various routes, e.g. orally, transdermally, perineurally or parenterally, that is, by intravenous, subcutaneous, intraperitoneal, or intramuscular injection, among others, including buccal, rectal and transdermal administration. Subjects contemplated for treatment according to the method of the present invention are animals, especially mammals, including humans, companion animals, domesticated animals, laboratory animals, and the like.

Formulations containing the compounds according to the present invention may take the form of solid, semi-solid, lyophilized powder, or liquid dosage forms, such as, for example, tablets, capsules, powders, sustained-release formulations, solutions, suspensions, emulsions, suppositories, creams, ointments, lotions, aerosols, patches or the like, preferably in unit dosage forms suitable for simple administration of precise dosages.

Pharmaceutical compositions according to the present invention comprise an effective amount of one or more compounds according to the present invention and typically include a conventional pharmaceutical carrier or excipient and may additionally include other medicinal agents, carriers, adjuvants, additives and the like. Preferably, the composition will be about 0.5 to 75% by weight or more of a compound or compounds of the present invention, with the remainder consisting essentially of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

Liquid compositions can be prepared by dissolving or dispersing the compounds (about 0.5% to about 20% by weight or more), and optional pharmaceutical adjuvants, in a carrier, such as, for example, aqueous saline, aqueous dextrose, glycerol, or ethanol, to form a solution or suspension. For use in oral liquid preparation, the composition may be prepared as a solution, suspension, emulsion, or syrup, being supplied either in liquid form or a dried form suitable for hydration in water or normal saline.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

An injectable composition for parenteral administration may typically comprise the compound in a solution suitable for intravenous administration (i.v.), wherein the solution, for example, is a sterile physiological salt solution. The composition may also be formulated as a suspension in a lipid or phospholipid, in a liposomal suspension, or in an aqueous emulsion.

Methods for preparing such dosage forms are known or will be apparent to those skilled in the art; for example, please refer to Remington's Pharmaceutical Sciences (17th Ed., Mack Pub. Co., 1985). The composition for administration may comprise a pharmaceutically effective amount of a selected compound to increase the concentration of the AMPA receptor synergist in a subject's brain.

Beneficial Effects of the Present Invention

The compound of Formula (I) provided by the present invention can increase the distribution of the AMPA receptor synergist N-(anti-4-hydroxycyclohexyl)-N-methylbenzo[c][1,2,5]oxadiazol-5-yl-carboxamide in the brain, improve the efficacy of the drug, and in the meantime reduce the distribution of the drug in peripheral organs so as to reduce the toxicity and side effects of the drug. In the experiment against respiratory depression induced by opiates, the compounds of Formula (I) significantly increase the survival rate of mice. The compound is significantly and surprisingly more potent than the prototype compound (i.e., Compound a), and achieve the same anti-lethal effect as the prototype compound (i.e., Compound a) at a significantly lower molar dose.

SPECIFIC MODELS FOR CARRYING OUT THE PRESENT INVENTION

Figure 1:
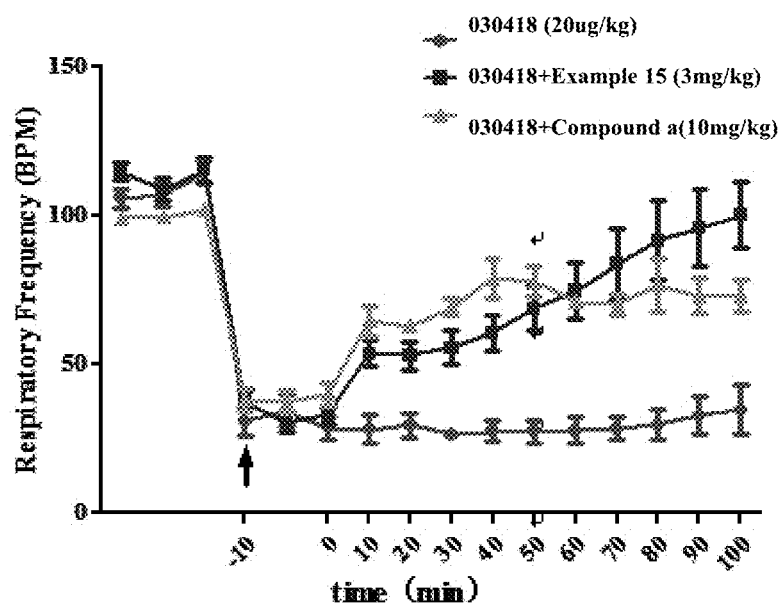
FIG. 1 shows the effect of Compound 15 on respiratory rate in rats with respiratory depression.

The embodiments of the present invention will be described in detail in combination with the following examples. Those skilled in the art will understand that the following examples are merely aimed to illustrate the present invention and should not be construed as any limitation of the scope of the present invention. If the specific techniques or conditions are not indicated in the examples, the techniques or conditions are conducted according to those described in the literatures of the field or product instruction. The reagents or instruments, the manufacturer of which is not indicated, are commercially available.

Example 1

Succinic acid anti-4-[(benzo[c][1,2,5]oxadiazole-5-carbonyl)-methyl-amino]-cyclohexyl ester 3-ethyldisulfanyl-4-(formyl-methyl-amino)-pent-3-enyl ester (Compound 1)

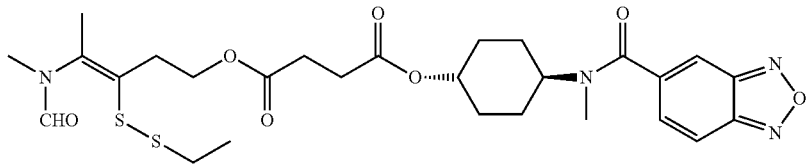

a) Preparation of sodium ethyl thiosulfate ($R_2$=$CH_2CH_3$)

Bromoethane (10.9 g, 100 mmol) was dissolved in 30 ml of absolute ethanol, sodium thiosulfate (24.8 g, 100 mmol) was dissolved in 60 ml of water, the above two solutions were mixed, heated to reflux in an oil bath and reacted for 10 h. After the reaction was complete, the resulting reactant was concentrated under reduced pressure, dried to give white crystal of sodium ethyl thiosulfate (15.2 g), which has an unpleasant smell.

b) Preparation of 3,4-dimethyl-5-(2-hydroxy-ethyl)-thiazolium iodide ($R_1$=$CH_3$)

A mixture of 4-methyl-5-thiazoleethanol (100 g, 698.2 mmol) and methyl iodide (100 ml, 1500.0 mmol) was heated to reflux in an oil bath. After 2 h, the reaction was complete. Excess methyl iodide was evaporated under reduced pressure to afford 3,4-dimethyl-5-(2-hydroxy-ethyl)-thiazolium iodide (191.4 g) as a yellow crystalline solid. mp: 82-84° C.

c) Preparation of N-methyl-N-(4-hydroxyl-1-methyl-2-ethyldisulfanyl-but-1-enyl)-formamide ($R_1$=$CH_3$, $R_2$=$CH_2CH_3$)

Under $N_2$ protection, NaOH (4 g) and 3,4-dimethyl-5-(2-hydroxy-ethyl)-thiazolium iodide (14.3 g, 50 mmol) were dissolved in water (30 ml), then added with sodium ethyl thiosulfate (19.7 g, 120 mmol). The resulting mixture was reacted at room temperature for half an hour, then extracted with ethyl acetate (150 ml×3), the organic layers were combined and dried by evaporation under reduced pressure to obtain a crude product, which was purified with silica gel column chromatography (dichloromethane/methanol (100:1)) to obtain N-methyl-N-(4-hydroxyl-1-methyl-2-ethyldisulfanyl-but-1-enyl)-formamide (4.8 g) as a yellow oil.

MS(ESI): 236 ([M+H]$^+$)

$^1$HNMR(CDCl$_3$) δ7.96, 7.84 (1H, 2s); 3.55-3.43 (2H, m); 2.98, 2.83 (3H, 2s); 2.70 (2H, t); 2.64 (2H, q); 1.96, 1.86 (2s, 3H); 1.19 (3H, t).

d) Preparation of Succinic acid mono-[3-ethyldisulfanyl-4-(formyl-methyl-amino)-pent-3-enyl] ester (R$_1$=CH$_3$, R$_2$=CH$_2$CH$_3$, n=2)

N-methyl-N-(4-hydroxyl-1-methyl-2-ethyldisulfanyl-but-1-enyl)-formamide (2.35 g, 10 mmol), succinic anhydride (3.4 g, 30 mmol) and N,N-dimethylaminopyridine (0.1 g, 1.0 mmol) were dissolved in anhydrous dichloromethane (50 ml), heated to reflux with stirring in an oil bath, and reacted for 6 h. TLC detection showed the completion of the reaction. The reaction mixture was dried and purified by silica gel column chromatography (dichloromethane/methanol (100:1)) to give succinic acid mono-[3-ethyldisulfanyl-4-(formyl-methyl-amino)-pent-3-enyl] ester as a yellow oil (3.1 g).

e) Succinic acid anti-4-[(benzo[c][1,2,5]oxadiazole-5-carbonyl)-methyl-amino]-cyclohexyl ester 3-ethyldisulfanyl-4-(formyl-methyl-amino)-pent-3-enyl ester In a dry eggplant-shaped bottle (250 ml), N-(anti-4-hydroxycyclohexyl)-N-methylbenzo[c][1,2,5]oxadiazol-5-yl-carboxamide (1.0 g, 3.6 mmol), succinic acid mono-[3-ethyldisulfanyl-4-(formyl-methyl-amino)-pent-3-enyl] ester (1.6 g, 4.7 mmol), 4-dimethylaminopyridine (44 mg, 0.36 mol), triethylamine (0.5 ml, 3.6 mmol) and 1-hydroxylbenzotriazole (0.49 g, 3.6 mmol) were added, dissolved with dichloromethane (50 ml), and heated to reflux for 15 min, then added with N-(3-dimethylaminopropyl)-N'-ethylcarbodiimide hydrochloride (1.1 g, 5.4 mol) and refluxed for 5 h, TLC detection showed the completion of the reaction. The reaction solution was concentrated by rotary evaporation, purified by silica gel column chromatography (ethyl acetate/petroleum ether(1:1)) to obtain the desired product Succinic acid anti-4-[(benzo[c][1,2,5]oxadiazole-5-carbonyl)-methyl-amino]-cyclohexyl ester 3-ethyldisulfanyl-4-(formyl-methyl-amino)-pent-3-enyl ester (1.21 g).

MS(ESI) 593 (M+H)+

$^1$HNMR(CDCl$_3$) δ7.93-7.83 (3H, m); 7.41 (1H, d); 4.71-4.56, 3.49 (2H, m); 4.26 (2H, m); 3.04-2.87 (8H, m); 2.62-2.55 (6H, m); 2.11-1.60 (11H, m); 1.27 (3H, t).

Example 2

Succinic acid anti-4-[(benzo[c][1,2,5]oxadiazole-5-carbonyl)-methyl-amino]-cyclohexyl ester 3-propyldisulfanyl-4-(formyl-methyl-amino)-pent-3-enyl ester (Compound 2)

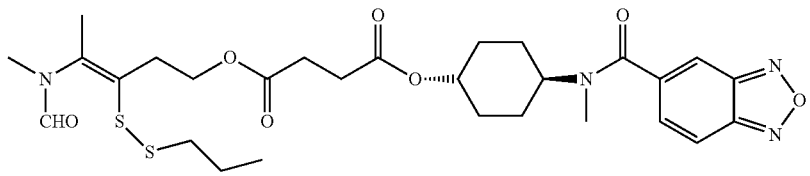

The title compound was prepared according to the method described in Example 1, wherein, in step a), 1-bromopropane was used instead of bromoethane, and the other procedures were similar. The obtained product was succinic acid anti-4-[(benzo[c][1,2,5]oxadiazole-5-carbonyl)-methyl-amino]-cyclohexyl ester 3-propyldisulfanyl-4-(formyl-methyl-amino)-pent-3-enyl ester.

MS(ESI) 607 (M+H)$^+$ $^1$HNMR(CDCl$_3$) δ7.93-7.83 (3H, m); 7.41 (1H, d); 4.71-5.56, 3.51 (2H, m); 4.27 (2H, m); 3.03-2.87 (8H, m); 2.62 (6H, m); 2.14-1.32 (17H, m); 0.89 (3H, t).

Example 3

Succinic acid anti-4-[(benzo[c][1,2,5]oxadiazole-5-carbonyl)-methyl-amino]-cyclohexyl ester 3-isopropyldisulfanyl-4-(formyl-methyl-amino)-pent-3-enyl ester (Compound 3)

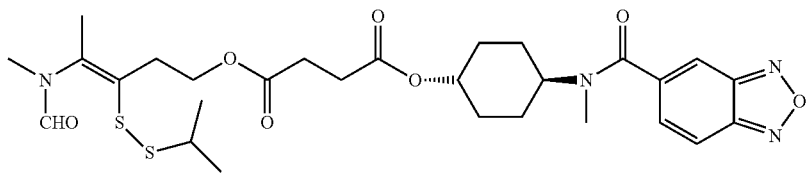

The title compound was prepared according to the method described in Example 1, wherein, in step a), 2-bromopropane was used instead of bromoethane, and the other processes were similar. The obtained product was succinic acid anti-4-[(benzo[c][1,2,5]oxadiazole-5-carbonyl)-methyl-amino]-cyclohexyl ester 3-isopropyldisulfanyl-4-(formyl-methyl-amino)-pent-3-enyl ester.

MS(ESI) 607 (M+H)$^+$ $^1$HNMR(CDCl$_3$) δ7.92-7.82 (3H, m); 7.40 (1H, d); 4.71-4.56, 3.50 (2H, m); 4.25 (2H, m); 3.04-2.86 (8H, m); 2.60-2.53 (4H, m); 2.13 (1H, m); 2.03, 1.96 (3H, 2s); 1.91-1.59 (8H, m); 1.24 (6H, d).

Example 4

Succinic acid anti-4-[(benzo[c][1,2,5]oxadiazole-5-carbonyl)-methyl-amino]-cyclohexyl ester 3-butyldisulfanyl-4-(formyl-methyl-amino)-pent-3-enyl ester (Compound 4)

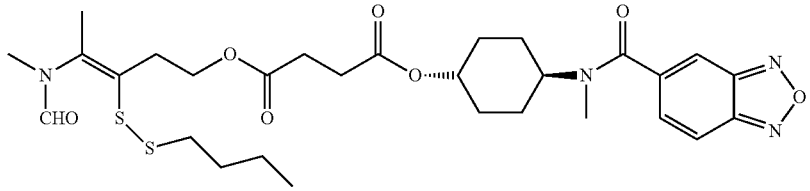

The title compound was prepared according to the method described in Example 1, wherein, in step a), 1-bromobutane was used instead of bromoethane, and the other processes were similar. The obtained product was succinic acid anti-4-[(benzo[c][1,2,5]oxadiazole-5-carbonyl)-methyl-amino]-cyclohexyl ester 3-butyldisulfanyl-4-(formyl-methyl-amino)-pent-3-enyl ester.

MS(ESI) 621 (M+H)$^+$ $^1$HNMR (CDCl$_3$) δ7.93-7.82 (3H, m); 7.41 (1H, d); 4.71-4.56, 3.49 (2H, m); 4.26 (2H, m); 3.03-2.87 (8H, m); 2.61 (6H, m); 2.00, 1.98 (2s, 3H); 1.98-1.25 (12H, m); 0.91 (3H, t).

Example 5

Succinic acid anti-4-[(benzo[c][1,2,5]oxadiazole-5-carbonyl)-methyl-amino]-cyclohexyl ester 3-isobutyldisulfanyl-4-(formyl-methyl-amino)-pent-3-enyl ester (Compound 5)

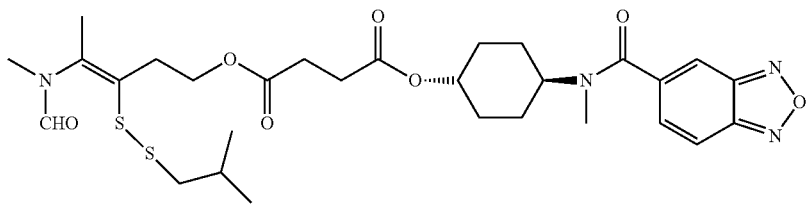

The title compound was prepared according to the method described in Example 1, wherein, in step a), 1-bromo-2-methylpropane was used instead of bromoethane, and the other processes were similar. The obtained product was succinic acid anti-4-[(benzo[c][1,2,5]oxadiazole-5-carbonyl)-methyl-amino]-cyclohexyl ester 3-isobutyldisulfanyl-4-(formyl-methyl-amino)-pent-3-enyl ester.

MS(ESI) 621 (M+H)$^+$ $^1$HNMR(CDCl$_3$) δ7.93-7.82 (3H, m); 7.41 (1H, d); 4.72-4.56, 3.50 (2H, m); 4.27 (2H, m); 3.01-2.87 (8H, m); 2.61-2.49 (6H, m); 2.00, 1.98 (3H, 2s); 1.92-1.25 (9H, m); 0.97 (6H, d).

Example 6

Succinic acid anti-4-[(benzo[c][1,2,5]oxadiazole-5-carbonyl)-methyl-amino]-cyclohexyl ester 3-pentyldisulfanyl-4-(formyl-methyl-amino)-pent-3-enyl ester (Compound 6)

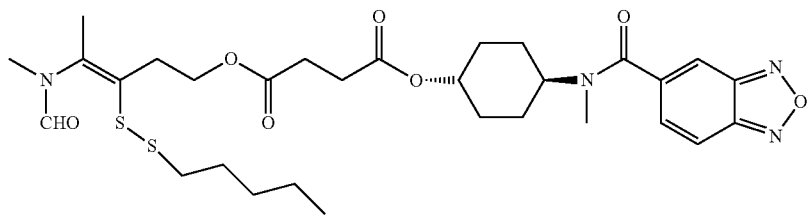

The title compound was prepared according to the method described in Example 1, wherein, in step a), 1-bromopentane was used instead of bromoethane, and the other processes were similar. The obtained product was succinic acid anti-4-[(benzo[c][1,2,5]oxadiazole-5-carbonyl)-methyl-amino]-cyclohexyl ester 3-pentyldisulfanyl-4-(formyl-methyl-amino)-pent-3-enyl ester.

MS(ESI) 635 (M+H)$^+$ $^1$HNMR(CDCl$_3$) δ7.93-7.83 (3H, m); 7.41 (1H, d); 4.71-4.59, 3.49 (2H, m), 4.26 (2H, m); 3.01-2.87 (8H, m); 2.61 (6H, m); 2.14-1.32 (17H, m); 0.89 (3H, t).

Example 7

Succinic acid anti-4-[(benzo[c][1,2,5]oxadiazole-5-carbonyl)-methyl-amino]-cyclohexyl ester 3-isopentyldisulfanyl-4-(formyl-methyl-amino)-pent-3-enyl ester (Compound 7)

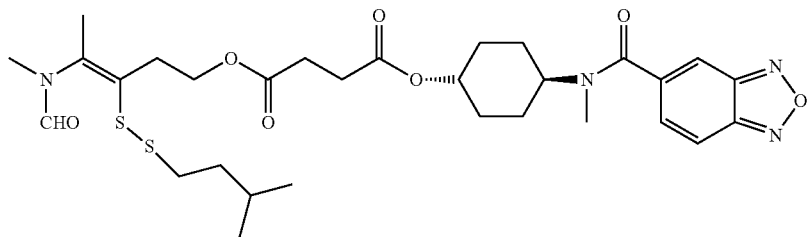

The title compound was prepared according to the method described in Example 1, wherein, in step a), 4-bromo-2-methylbutane was used instead of bromoethane, and the other processes were similar. The obtained product was succinic acid anti-4-[(benzo[c][1,2,5]oxadiazole-5-carbonyl)-methyl-amino]-cyclohexyl ester 3-isopentyldisulfanyl-4-(formyl-methyl-amino)-pent-3-enyl ester.

MS(ESI) 635 (M+H)$^+$ $^1$HNMR(CDCl$_3$) δ7.93-7.82 (3H, m); 7.41 (1H, d); 4.71-4.59, 3.50 (2H, m), 4.26 (2H, m); 3.00-2.87 (8H, m); 2.61 (6H, m); 2.05, 2.01 (3H, 2s); 1.93-1.25 (11H, m); 0.89 (6H, d).

Example 8

Succinic acid anti-4-[(benzo[c][1,2,5]oxadiazole-5-carbonyl)-methyl-amino]-cyclohexyl ester 3-benzyldisulfanyl-4-(formyl-methyl-amino)-pent-3-enyl ester (Compound 8)

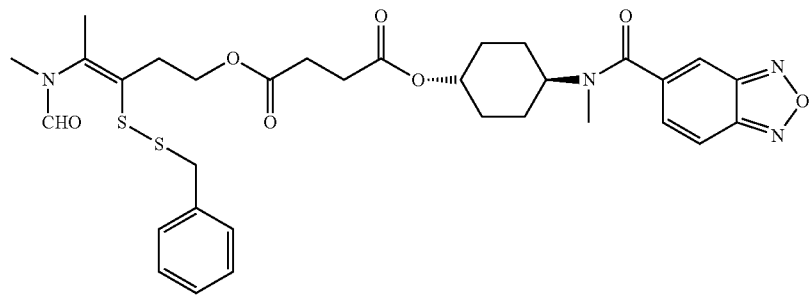

The title compound was prepared according to the method described in Example 1, wherein, in step a), benzyl bromide was used instead of bromoethane, and the other processes were similar. The obtained product was succinic acid anti-4-[(benzo[c][1,2,5]oxadiazole-5-carbonyl)-methyl-amino]-cyclohexyl ester 3-benzyldisulfanyl-4-(formyl-methyl-amino)-pent-3-enyl ester.

MS(ESI) 655 (M+H)$^+$ $^1$HNMR(CDCl$_3$) δ7.93, 7.91 (1H, 2s); 7.82 (2H, m); 7.41 (1H, d); 7.33-7.28 (5H, m); 4.70-4.58, 3.49 (2H, m); 4.18 (2H, m); 3.86 (2H, s); 3.00-2.77 (8H, m); 2.60-2.53 (4H, m); 2.13, 2.03 (3H, 2s); 1.92-1.21 (8H, m).

Example 9

Pentanedioic acid anti-4-[(benzo[c][1,2,5]oxadiazole-5-carbonyl)-methyl-amino]-cyclohexyl ester 3-ethyldisulfanyl-4-(formyl-methyl-amino)-pent-3-enyl ester (Compound 9)

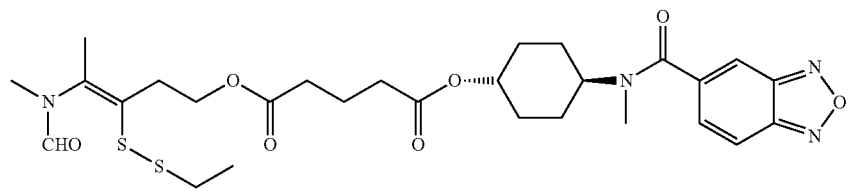

The title compound was prepared according to the method described in Example 1, wherein, in step d), glutaric anhydride was used instead of succinic anhydride, and the other processes were similar. The obtained product was pentanedioic acid anti-4-[(benzo[c][1,2,5]oxadiazole-5-carbonyl)-methyl-amino]-cyclohexyl ester 3-ethyldisulfanyl-4-(formyl-methyl-amino)-pent-3-enyl ester.

MS(ESI) 655 (M+H)$^+$ $^1$HNMR(CDCl$_3$) δ7.98-7.83 (3H, m); 7.41 (1H, d); 4.70-4.59, 3.51 (2H, m); 4.24 (2H, m); 3.04-2.87 (8H, m); 2.71-2.59 (2H, m); 2.42-2.35 (4H, m); 2.11-1.62 (11H, m); 1.27 (3H, t).

Example 10

Pentanedioic acid anti-4-[(benzo[c][1,2,5]oxadiazole-5-carbonyl)-methyl-amino]-cyclohexyl ester 3-propyldisulfanyl-4-(formyl-methyl-amino)-pent-3-enyl ester (Compound 10)

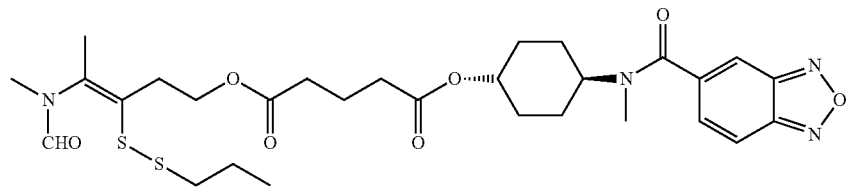

The title compound was prepared according to the method described in Example 1, wherein, 1-bromopropante was used instead of bromoethane in step a), glutaric anhydride was used instead of succinic anhydride in step d), and the other processes were similar. The obtained product was pentanedioic acid anti-4-[(benzo[c][1,2,5]oxadiazole-5-carbonyl)-methyl-amino]-cyclohexyl ester 3-propyldisulfanyl-4-(formyl-methyl-amino)-pent-3-enyl ester.

MS(ESI) 621 (M+H)$^+$ $^1$HNMR(CDCl$_3$) δ7.98-7.83 (3H, m); 7.42 (1H, d); 4.70-4.56, 3.50 (2H, m); 4.25 (2H, m); 3.04-2.88 (8H, m); 2.58 (2H, t); 2.37-2.31 (4H, m); 2.13-2.11 (2H, m); 2.00, 1.97 (3H, 2s); 1.94-1.23 (10H, m); 0.96 (3H, t).

Example 11

Pentanedioic acid anti-4-[(benzo[c][1,2,5]oxadiazole-5-carbonyl)-methyl-amino]-cyclohexyl ester 3-isopropyldisulfanyl-4-(formyl-methyl-amino)-pent-3-enyl ester (Compound 11)

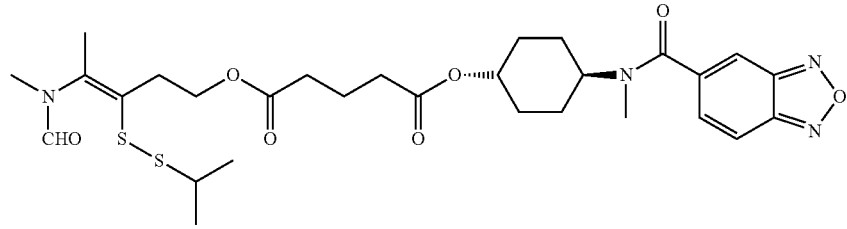

The title compound was prepared according to the method described in Example 1, wherein, 2-bromopropante was used instead of bromoethane in step a), glutaric anhydride was used instead of succinic anhydride in step d), and the other processes were similar. The obtained product was pentanedioic acid anti-4-[(benzo[c][1,2,5]oxadiazole-5-carbonyl)-methyl-amino]-cyclohexyl ester 3-isopropyldisulfanyl-4-(formyl-methyl-amino)-pent-3-enyl ester.

MS(ESI) 621 (M+H)$^+$ $^1$HNMR(CDCl$_3$) δ7.94-7.83 (3H, m); 7.42 (1H, d); 4.70-4.58, 3.50 (2H, m); 4.23 (2H, m); 3.05-2.87 (8H, m); 2.48-2.37 (5H, m); 2.13-1.99 (5H, m); 1.96-1.23 (8H, m); 1.26 (6H, d).

Example 12

Pentanedioic acid anti-4-[(benzo[c][1,2,5]oxadiazole-5-carbonyl)-methyl-amino]-cyclohexyl ester 3-butyldisulfanyl-4-(formyl-methyl-amino)-pent-3-enyl ester (Compound 12)

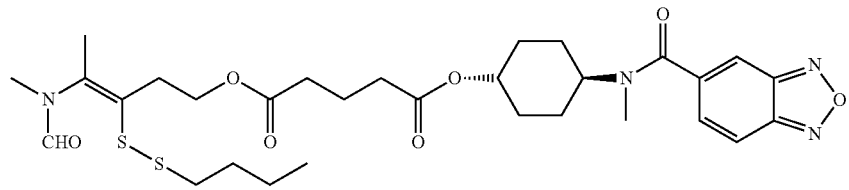

The title compound was prepared according to the method described in Example 1, wherein, 1-bromobutane was used instead of bromoethane in step a), glutaric anhydride was used instead of succinic anhydride in step d), and the other processes were similar. The obtained product was pentanedioic acid anti-4-[(benzo[c][1,2,5]oxadiazole-5-carbonyl)-methyl-amino]-cyclohexyl ester 3-butyldisulfanyl-4-(formyl-methyl-amino)-pent-3-enyl ester.

MS(ESI) 635 (M+H)$^+$ $^1$HNMR(CDCl$_3$) δ7.93-7.83 (3H, m); 7.42 (1H, d); 4.70-4.55, 3.49 (2H, m); 4.24 (2H, m); 3.03-2.87 (8H, m); 2.61 (2H, t); 2.37 (4H, m); 2.13 (2H, m); 2.03, 2.01 (3H, 2s); 1.96-1.25 (12H, m); 0.90 (3H, t).

Example 13

Pentanedioic acid anti-4-[(benzo[c][1,2,5]oxadiazole-5-carbonyl)-methyl-amino]-cyclohexyl ester 3-isobutyldisulfanyl-4-(formyl-methyl-amino)-pent-3-enyl ester (Compound 13)

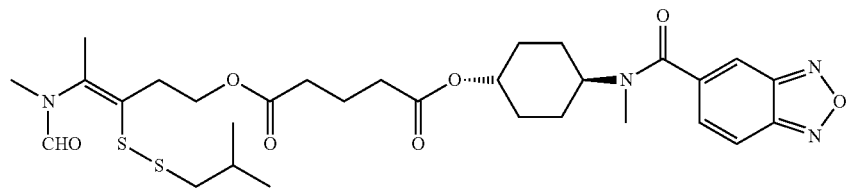

The title compound was prepared according to the method described in Example 1, wherein, 1-bromo-2-methylpropante was used instead of bromoethane in step a), glutaric anhydride was used instead of succinic anhydride in step d), and the other processes were similar. The obtained product was pentanedioic acid anti-4-[(benzo[c][1,2,5]oxadiazole-5-carbonyl)-methyl-amino]-cyclohexyl ester 3-isobutyldisulfanyl-4-(formyl-methyl-amino)-pent-3-enyl ester.

MS(ESI) 635 (M+H)$^+$ $^1$HNMR(CDCl$_3$) δ7.93-7.82 (3H, m); 7.41 (1H, d); 4.72-4.56, 3.50 (2H, m); 4.27 (2H, m); 3.01-2.87 (8H, m); 2.61-2.49 (6H, m); 2.00, 1.98 (3H, 2s); 1.92-1.25 (9H, m); 0.97 (6H, d).

Example 14

Pentanedioic acid anti-4-[(benzo[c][1,2,5]oxadiazole-5-carbonyl)-methyl-amino]-cyclohexyl ester 3-pentyldisulfanyl-4-(formyl-methyl-amino)-pent-3-enyl ester (Compound 14)

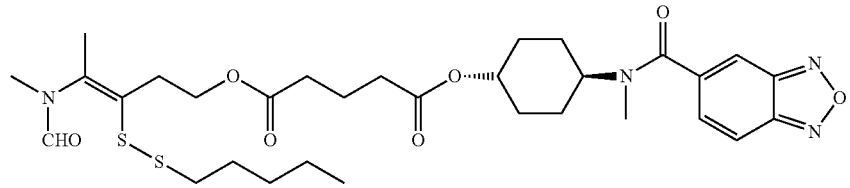

The title compound was prepared according to the method described in Example 1, wherein, 1-bromopentane was used instead of bromoethane in step a), glutaric anhydride was used instead of succinic anhydride in step d), and the other processes were similar. The obtained product was pentanedioic acid anti-4-[(benzo[c][1,2,5]oxadiazole-5-carbonyl)-methyl-amino]-cyclohexyl ester 3-pentyldisulfanyl-4-(formyl-methyl-amino)-pent-3-enyl ester.

MS(ESI) 649 (M+H)$^+$ $^1$HNMR(CDCl$_3$) δ7.93-7.83 (3H, m); 7.42 (1H, d); 4.71-4.59, 3.50 (2H, m), 4.24 (2H, m); 3.04-2.88 (8H, m); 2.60 (2H, t); 2.37-2.31 (4H, m); 2.13-2.00 (2H, m); 2.00, 1.97 (3H, 2s); 1.94-1.28 (14H, m); 0.89 (3H, t).

Example 15

Pentanedioic acid anti-4-[(benzo[c][1,2,5]oxadiazole-5-carbonyl)-methyl-amino]-cyclohexyl ester 3-isopentyldisulfanyl-4-(formyl-methyl-amino)-pent-3-enyl ester (Compound 15)

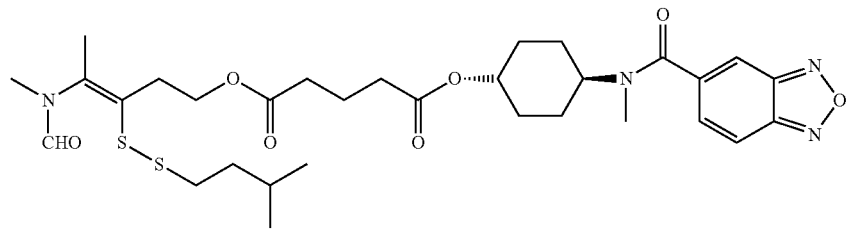

The title compound was prepared according to the method described in Example 1, wherein, 4-bromo-2-methylbutane was used instead of bromoethane in step a), glutaric anhydride was used instead of succinic anhydride in step d), and the other processes were similar. The obtained product was pentanedioic acid anti-4-[(benzo[c][1,2,5]oxadiazole-5-carbonyl)-methyl-amino]-cyclohexyl ester 3-isopentyldisulfanyl-4-(formyl-methyl-amino)-pent-3-enyl ester.

MS(ESI) 649 (M+H)$^+$ $^1$HNMR(CDCl$_3$) δ7.97-7.83 (3H, m); 7.41 (1H, d); 4.71-4.57, 3.51 (2H, m), 4.24 (2H, m); 3.03-2.87 (8H, m); 2.62 (2H, t); 2.37 (4H, m); 2.13 (2H, m); 2.00, 1.97 (3H, 2s); 1.96-1.21 (11H, m); 0.89 (6H, d).

Example 16

Pentanedioic acid anti-4-[(benzo[c][1,2,5]oxadiazole-5-carbonyl)-methyl-amino]-cyclohexyl ester 3-benzyldisulfanyl-4-(formyl-methyl-amino)-pent-3-enyl ester (Compound 16)

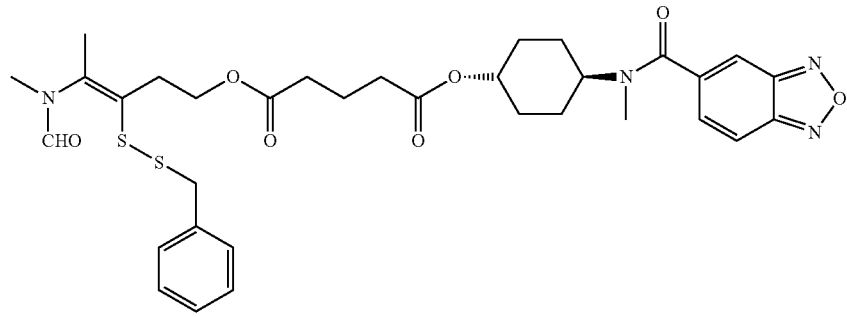

The title compound was prepared according to the method described in Example 1, wherein, benzyl bromide was used instead of bromoethane in step a), glutaric anhydride was used instead of succinic anhydride in step d), and the other processes were similar. The obtained product was pentanedioic acid anti-4-[(benzo[c][1,2,5]oxadiazole-5-carbonyl)-methyl-amino]-cyclohexyl ester 3-benzyldisulfanyl-4-(formyl-methyl-amino)-pent-3-enyl ester.

MS(ESI) 669 (M+H)$^+$ $^1$HNMR(CDCl$_3$) δ7.93, 7.91 (1H, 2s); 7.82 (2H, m); 7.41 (1H, d); 7.38-7.28 (5H, m); 4.69-4.59, 3.50 (2H, m); 4.15 (2H, m); 3.85 (2H, s); 3.00-2.75 (8H, m); 2.35 (4H, m); 2.10 (2H, m); 2.03-1.25 (11H, m).

Example 17

Pentanedioic acid anti-4-[(benzo[c][1,2,5]oxadiazole-5-carbonyl)-methyl-amino]-cyclohexyl ester 3-ethyldisulfanyl-4-(formyl-ethyl-amino)-pent-3-enyl ester (Compound 17)

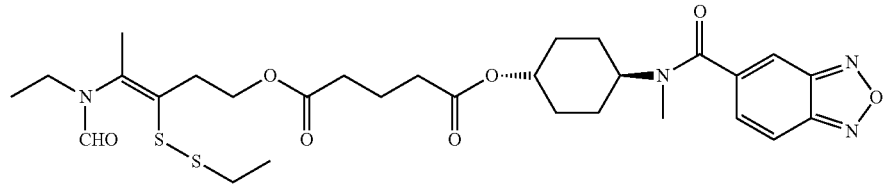

The title compound was prepared according to the method described in Example 1, wherein, 1-iodoethane was used instead of iodomethane in step b), glutaric anhydride was used instead of succinic anhydride in step d), and the other processes were similar. The obtained product was pentanedioic acid anti-4-[(benzo[c][1,2,5]oxadiazole-5-carbonyl)-methyl-amino]-cyclohexyl ester 3-ethyldisulfanyl-4-(formyl-ethyl-amino)-pent-3-enyl ester.

MS(ESI) 620 (M+H)$^+$ $^1$HNMR(CDCl$_3$) δ7.93-7.83 (3H, m); 7.41 (1H, d); 4.71-4.56, 3.49 (2H, m); 4.26 (2H, m); 3.04-2.87 (7H, m); 2.62-2.55 (6H, m); 2.11-1.60 (11H, m); 1.27 (3H, t); 1.24 (3H, t).

Example 18

Pentanedioic acid anti-4-[(benzo[c][1,2,5]oxadiazole-5-carbonyl)-methyl-amino]-cyclohexyl ester 3-ethyldisulfanyl-4-(formyl-propyl-amino)-pent-3-enyl ester (Compound 18)

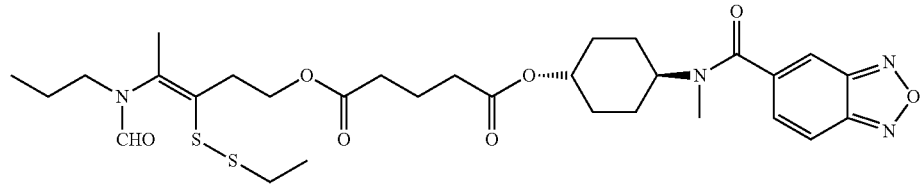

The title compound was prepared according to the method described in Example 1, wherein, 1-iodopropane was used instead of iodomethane in step b), glutaric anhydride was used instead of succinic anhydride in step d), and the other processes were similar. The obtained product was pentanedioic acid anti-4-[(benzo[c][1,2,5]oxadiazole-5-carbonyl)-methyl-amino]-cyclohexyl ester 3-ethyldisulfanyl-4-(formyl-propyl-amino)-pent-3-enyl ester.

MS(ESI) 634 (M+H)$^+$ $^1$HNMR(CDCl$_3$) δ7.93-7.83 (3H, m); 7.41 (1H, d); 4.71-4.56, 3.49 (2H, m); 4.26 (2H, m); 3.04-2.87 (7H, m); 2.62-2.55 (6H, m); 2.11-1.60 (13H, m); 1.27 (3H, t); 1.20 (3H, t).

Example 19

Pentanedioic acid anti-4-[(benzo[c][1,2,5]oxadiazole-5-carbonyl)-methyl-amino]-cyclohexyl ester 3-isopentyldisulfanyl-4-[formyl-(D-glucos-6-yl-carbonylmethyl)-amino]-pent-3-enyl ester (Compound 19)

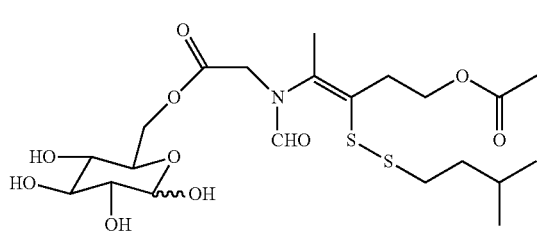

a) Preparation of sodium isopentyl thiosulfate (R$_2$=CH$_2$CH$_2$CH(CH$_3$)$_2$)

4-Bromo-2-methylbutane (15.0 g, 100 mmol) was dissolved in 30 ml of absolute ethanol, sodium thiosulfate (24.8 g, 100 mmol) was dissolved in 60 ml of water, and the two solutions were mixed and heated to reflux in an oil bath and reacted for 10 h. After the reaction was complete, the resulting reactant was concentrated under reduced pressure and dried to give white crystalline sodium isopentyl thiosulfate (18.3 g), which has an unpleasant smell.

b) Preparation of tert-butoxycarbonylethylated 3,4-dimethyl-5-(2-hydroxy-ethyl)thiazolium (R$_2$=CH$_2$CH$_2$CH(CH$_3$)$_2$)

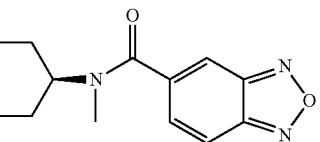

4-methyl-5-thiazoleethanol (50 g, 275.5 mmol) and tert-butyl bromoacetate (36.5 g, 275.5 mmol) were azeotroped in acetonitrile (350 ml) for 1.5 h. After the completion of the reaction, the mixture was cooled to room temperature and added with 50 ml of ethyl acetate to precipitate the product, which was subjected to suction filtration and vacuum dried to obtain white solid (83.9 g).

MS(ESI) 258 (M$^+$)

$^1$HNMR (DMSO-d$_6$) δ10.05 (1H, s); 5.52 (2H, s); 5.26 (1H, t); 3.65 ((2H, q); 3.05 (2H, t); 2.36 (3H, s); 1.46 (9H, s).

c) Preparation of N-tert-butoxycarbonylethyl-N-(4-hydroxyl-1-methyl-2-isopentyldisulfanyl-but-1-enyl)-formamide (R$_2$=CH$_2$CH$_2$CH(CH$_3$)$_2$)

Under N$_2$ protection, NaOH (2.16 g, 54 mmol) and tert-butyloxycarbonylethylated 3,4-dimethyl-5-(2-hydroxyethyl)thiazolium (9.1 g, 27 mmol) were dissolved in water (40 ml), then added with sodium isopentyl thiosulfate (16.7 g, 81 mmol). The resulting mixture was reacted at room temperature for half an hour, then extracted with ethyl acetate (150 ml×3), and the organic layers were combined, and dried by rotary evaporation to obtain a crude product, which was purified by silica gel column chromatography (dichloromethane/methanol (100:1)) to give N-tert-butyloxycarbonylethyl-N-(4-hydroxyl-1-methyl-2-isopentyldisulfanyl-but-1-enyl)-formamide (5.1 g).

MS(ESI) 378 (M+H)$^+$ $^1$HNMR(CDCl$_3$) δ8.05, 8.01 (1H, 2s); 3.80 (2H, t); 2.88 (2H, t); 2.64 (2H, t); 2.07, 2.02 (3H, 2s); 1.51-1.47 (12H, m); 0.90 (6H, d).

d) Preparation of pentanedioic acid mono-[3-isopentyldisulfanyl-4-(tert-butoxycarbonylmethyl-formyl-amino)-pent-3-enyl]ester (R$_2$=CH$_2$CH$_2$CH(CH$_3$)$_2$, n=2)

N-tert-butoxycarbonylethyl-N-(4-hydroxyl-1-methyl-2-isopentyldisulfanyl-but-1-enyl)-formamide (3.77 g, 10 mmol), glutaric anhydride (3.4 g, 30 mmol) and N,N-dimethylaminopyridine (0.1 g, 1.0 mmol) were dissolved in anhydrous dichloromethane (50 ml), and heated in an oil bath to reflux, then reacted for 6 h, until TLC detection showed the completion of the reaction. The reaction mixture was dried by rotary evaporation and purified by silica gel column chromatography (dichloromethane/methanol (100:1)) to obtain yellow oily product pentanedioic acid mono-[3-isopentyldisulfanyl-4-(tert-butoxycarbonylmethyl-formyl-amino)-pent-3-enyl]ester (2.46 g).

MS(ESI) 492 (M+H)$^+$ $^1$HNMR(CDCl$_3$) δ8.02, 8.01 (1H, 2s); 4.24 (2H, t); 4.01 (2H, s); 2.95 (2H, t); 2.64 (2H, t); 2.45-2.38 (4H, m); 2.07, 2.05 (3H, 2s); 1.95 (2H, t); 1.67-1.62 (1H, m); 1.52-1.48 (2H, m); 1.47 (9H, s); 0.90 (6H, d).

e) Pentanedioic acid anti-4-[(benzo[c][1,2,5]oxadiazole-5-carbonyl)-methyl-amino]-cyclohexyl ester 3-isopentyldisulfanyl-4-(tert-butoxycarbonylmethyl-formyl-amino)-pent-3-enyl ester
($R_2$=—CH$_2$CH$_2$CH(CH$_3$)$_2$, n=3)

In a dry eggplant-shaped bottle (250 ml), N-(anti-4-hydroxycyclohexyl)-N-methylbenzo[c][c][1,2,5]oxadiazol-5-carboxamide (1.0 g, 3.6 mmol), pentanedioic acid mono-[3-isopentyldisulfanyl-4-(tert-butoxycarbonylmethyl-formyl-amino)-pent-3-enyl]ester (1.47 g, 3.0 mmol), 4-dimethylaminopyridine (44 mg, 0.36 mol), triethylamine (0.5 ml, 3.6 mmol) and 1-hydroxyl-benzotriazole (0.4 g, 3.0 mmol) were added, dissolved with dichloromethane (50 ml), and heated to reflux, for 15 min, then added with N-(3-dimethylaminopropyl)-N'-ethylcarbodiimide hydrochloride (1.1 g, 5.4 mol) and refluxed for 5 h, until TLC detection showed the completion of the reaction. The reaction solution was concentrated by rotary evaporation, purified by silica gel column chromatography (ethyl acetate/petroleum ether (1:1)), to give the desired product pentanedioic acid anti-4-[(benzo[c][1,2,5]oxadiazole-5-carbonyl)-methyl-amino]-cyclohexyl ester 3-isopentyldisulfanyl-4-(tert-butoxycarbonylmethyl-formyl-amino)-pent-3-enyl ester (0.75 g).

MS(ESI) 749 (M+H)$^+$ $^1$HNMR(CDCl$_3$) δ8.01-7.83 (3H, m); 7.42 (1H, d); 4.23 (2H, m); 4.00 (2H, s); 4.72-4.62, 3.50 (2H, m); 3.01-2.88 (5H, m); 2.64 (2H, t); 2.37 (4H, m); 2.11-2.05 (5H, m); 1.95-1.25 (10H, m); 1.47 (9H, s); 0.90 (6H, d).

f) Pentanedioic acid anti-4-[(benzo[c][1,2,5]oxadiazole-5-carbonyl)-methyl-amino]-cyclohexyl ester 3-isopentyldisulfanyl-4-(carboxymethyl-formyl-amino)-pent-3-enyl ester
($R_2$=—CH$_2$CH$_2$CH(CH$_3$)$_2$, n=3)

Pentanedioic acid anti-4-[(benzo[c][1,2,5]oxadiazole-5-carbonyl)-methyl-amino]-cyclohexyl ester 3-isopentyldisulfanyl-4-(tert-butoxycarbonylmethyl-formyl-amino)-pent-3-enyl ester (1.50 g, 2.0 mmol) was dissolved in dichloromethane (50 ml). Under stirring at room temperature, 70% perchloric acid (0.11 ml, 2.0 mmol) was slowly added dropwise to the solution. After stirring at room temperature for 6 h, sodium hydrogencarbonate solid (1.0 g, 11.9 mmol) was added to the solution to adjust the pH to neutral. After filtration, the filtrate was loaded to silica gel and purified by silica gel column chromatography (dichloromethane/methanol=30:1) to obtain the desired product Pentanedioic acid anti-4-[(benzo[c][1,2,5]oxadiazole-5-carbonyl)-methyl-amino]-cyclohexyl ester 3-isopentyldisulfanyl-4-(carboxymethyl-formyl-amino)-pent-3-enyl ester (0.61 g).

MS(ESI) 691 (M−H)$^−$ $^1$HNMR(CDCl$_3$) δ8.00-7.83 (3H, m); 7.44 (1H, d); 4.32-4.13 (4H, m); 4.72-4.59, 3.52 (2H, m); 3.00-2.89 (5H, m); 2.65 (2H, t); 2.37 (4H, m); 2.06 (5H, m); 1.93-1.25 (11H, m); 0.88 (6H, d).

g) Pentanedioic acid anti-4-[(benzo[c][1,2,5]oxadiazole-5-carbonyl)-methyl-amino]-cyclohexyl ester 3-isopentyldisulfanyl-4-[formyl-(D-glucos-6-yl-carbonylmethyl)-amino]-pent-3-enyl ester
($R_2$=—CH$_2$CH$_2$CH(CH$_3$)$_2$, n=3)

In a dry eggplant-shaped bottle (100 ml), pentanedioic acid anti-4-[(benzo[c][1,2,5]oxadiazole-5-carbonyl)-methyl-amino]-cyclohexyl ester 3-isopentyldisulfanyl-4-(carboxymethyl-formyl-amino)-pent-3-enyl ester (0.56 g, 0.81 mmol, Example 18e), 1,2,3,4-tetra-O-acetyl-β-D-glucose (230 mg, 0.67 mmol), 4-dimethylaminopyridine (40 mg, 0.36 mol) and 1-hydroxyl-benzotriazole (120 mg, 0.88 mmol) were added and dissolved in a mixed solvent of anhydrous N,N-dimethylformamide (5 ml)/anhydrous dichloromethane (25 ml), the mixture was stirred at room temperature for 30 min, followed by an addition of N,N-dicyclohexylimine (280 mg, 1.34 mmol) and the stirring was conducted at room temperature overnight until TLC showed the completion of the reaction. The reactant was filtered, the filtrate was rotary evaporated and purified by silica gel column chromatography (ethyl acetate/petroleum ether (1:2)) to give the desired product pentanedioic acid anti-4-[(benzo[c][1,2,5]oxadiazole-5-carbonyl)-methyl-amino]-cyclohexyl ester 3-isopentyldisulfanyl-4-[formyl-(D-glucos-6-yl-carbonylmethyl)-amino]-pent-3-enyl ester (0.27 g).

MS(ESI) 1023 (M+H)

$^1$HNMR(CDCl$_3$) δ8.02-7.83 (3H, m); 7.42 (1H, D); 5.70 (1H, D); 5.25 (1H, t); 5.14-5.05 (2H, m); 4.37-3.85 (6H, m); 4.70-4.60, 3.50 (2H, m); 3.01-2.88 (5H, m); 2.65 (2H, t); 2.37 (4H, m); 2.12-2.02 (18H, m); 2.02-1.25 (10H, m); 0.91 (6H, D).

h) Pentanedioic acid anti-4-[(benzo[c][1,2,5]oxadiazole-5-carbonyl)-methyl-amino]-cyclohexyl ester 3-isopentyldisulfanyl-4-[formyl-(D-glucos-6-yl-carbonylmethyl)-amino]-pent-3-enyl ester ($R_1$=

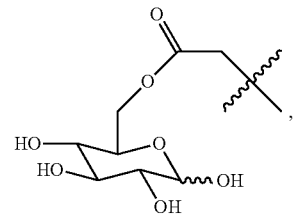 [SMILES: *CC(=O)OCC1OC(O)C(O)C(O)C1O]

$R_2$=—CH$_2$CH$_2$CH(CH$_3$)$_2$, n=3)

Pentanedioic acid anti-4-[(benzo[c][1,2,5]oxadiazole-5-carbonyl)-methyl-amino]-cyclohexyl ester 3-isopentyldisulfanyl-4-[formyl-(D-glucos-6-yl-carbonylmethyl)-amino]-pent-3-enyl ester (0.37 g, 0.36 mmol) was dissolved in methanol (20 ml). Sodium carbonate (19 mg, 0.18 mmol) was added to the solution at 0° C. The resulting mixture was reacted under ice-bath for 2 h, then subjected to filtration, the filtrate was dried by rotary evaporation and purified by silica gel column chromatography (dichloromethane/methanol=30:1) to obtain product Pentanedioic acid anti-4-[(benzo[c][1,2,5]oxadiazole-5-carbonyl)-methyl-amino]-cyclohexyl ester 3-isopentyldisulfanyl-4-[formyl-(D-glucos-6-yl-carbonylmethyl)-amino]-pent-3-enyl ester (46 mg).

MS(ESI) 855 (M+H)$^+$

¹HNMR (Methanol-D4) δ8.06-7.97 (3H, m); 7.54-7.49 (1H, m); 5.07 (1H, D); 4.48-4.39 (2H, m); 4.30-4.15 (4H, m); 3.99-3.96 (1H, m); 3.66 (1H, t); 3.51 (1H, m); 4.73-4.62, 3.26 (2H, m); 3.13 (1H, t); 3.01-2.91 (5H, m); 2.71-2.65 (2H, m); 2.41-2.23 (4H, m); 2.11-2.06 (5H, m); 1.90-1.28 (11H, m); 0.92 (6H, D).

Example 20

Pentanedioic acid anti-4-[(benzo[c][1,2,5]oxadiazole-5-carbonyl)-methyl-amino]-cyclohexyl ester 3-ethyldisulfanyl-4-[formyl-(D-glucos-6-yl-carbonylmethyl)-amino]-pent-3-enyl ester (Compound 20)

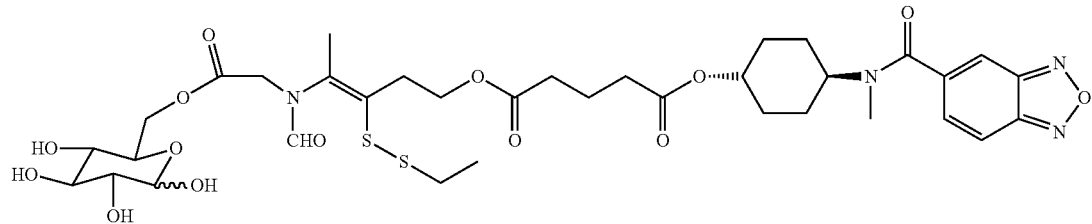

The title compound was prepared according to the method described in Example 19, wherein, bromoethane was used instead of 4-bromo-2-methylbutane in step a), and the other processes were similar. The obtained product was pentanedioic acid anti-4-[(benzo[c][1,2,5]oxadiazole-5-carbonyl)-methyl-amino]-cyclohexyl ester 3-ethyldisulfanyl-4-[formyl-(D-glucos-6-yl-carbonylmethyl)-amino]-pent-3-enyl ester.

MS(ESI) 827 (M+H)⁺

¹HNMR (Methanol-D4)(8.06-7.96 (3H, m); 7.55-7.47 (1H, m); 5.08 (1H, D); 4.49-4.39 (2H, m); 4.31-4.15 (4H, m); 3.99-3.96 (1H, m); 3.66 (1H, t); 3.50 (1H, m); 4.73-4.62, 3.26 (2H, m); 3.12 (1H, t); 3.02-2.91 (5H, m); 2.64 (2H, q); 2.40-2.26 (4H, m); 2.10, 2.05 (3H, 2s); 2.00 (2H, m); 1.91-1.27 (10H, m); 0.99 (3H, t).

Example 21

Pentanedioic acid anti-4-[(benzo[c][1,2,5]oxadiazole-5-carbonyl)-methyl-amino]-cyclohexyl ester 3-hexyldisulfanyl-4-[formyl-(D-glucos-6-yl-carbonylmethyl)-amino]-pent-3-enyl ester (Compound 21)

The title compound was prepared according to the method described in Example 19, wherein, 1-bromohexane was used instead of 4-bromo-2-methylbutane in step a), and the other processes were similar. The obtained product was pentanedioic acid anti-4-[(benzo[c][1,2,5]oxadiazole-5-carbonyl)-methyl-amino]-cyclohexyl ester 3-hexyldisulfanyl-4-[formyl-(D-glucos-6-yl-carbonylmethyl)-amino]-pent-3-enyl ester.

MS(ESI) 869 (M+H)⁺

¹HNMR (Methanol-D4) δ8.06-7.97 (3H, m); 7.52-7.45 (1H, m); 5.08 (1H, D); 4.52-4.39 (2H, m); 4.30-4.15 (4H, m); 3.99-3.96 (1H, m); 3.66 (1H, t); 3.54-3.48 (1H, m); 4.75-4.62, 3.26 (2H, m); 3.13 (1H, t); 3.02-2.91 (5H, m); 2.68 (2H, q); 2.41-2.26 (4H, m); 2.11, 2.06 (3H, 2s); 2.04-1.99 (2H, m); 1.91-1.23 (14H, m); 0.91 (3H, t).

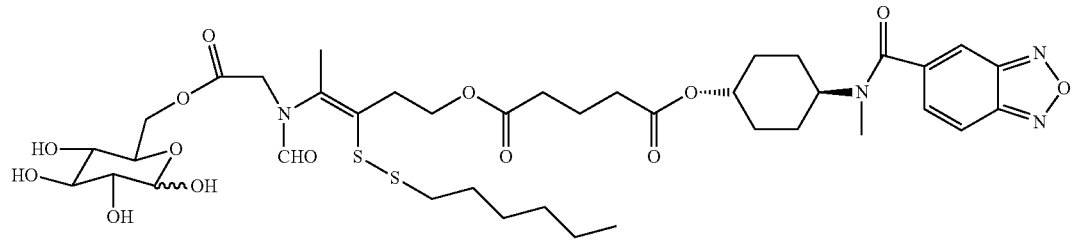

Example 22

Pentanedioic acid anti-4-[(benzo[c][1,2,5]oxadiazole-5-carbonyl)-methyl-amino]-cyclohexyl ester 3-ethyldisulfanyl-4-{[2-(3,4-dihydroxy-5-oxo-2,5-dihydro-furan-2-yl)-2-hydroxy-ethoxycarbonylmethyl]-formyl-amino}-pent-3-enyl ester (Compound 22)

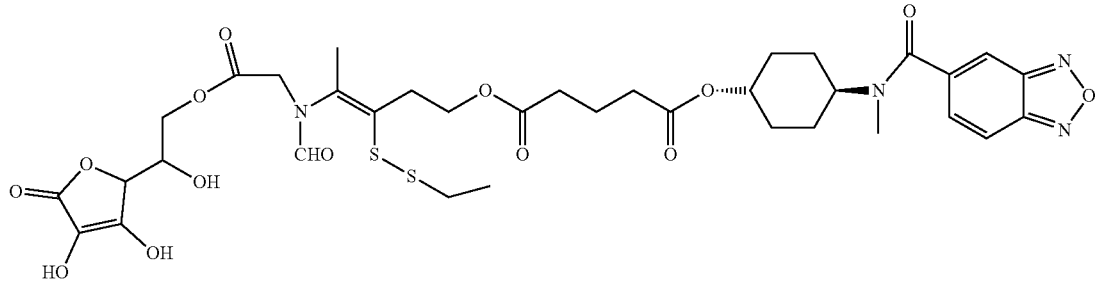

The title compound was prepared according to the method described in Example 19, wherein, bromoethane was used instead of 4-bromo-2-methylbutane in step a), 5-(1,2-dihydroxyethyl)-3,4-bis((2-methoxyethoxy)methoxy)furan-2(5H)-one was used instead of 1,2,3,4-tetra-O-acetyl-β-D-glucose in step g), and the other processes were similar. The obtained product was pentanedioic acid anti-4-[(benzo[c][1,2,5]oxadiazole-5-carbonyl)-methyl-amino]-cyclohexyl ester 3-ethyldisulfanyl-4-{[2-(3,4-dihydroxy-5-oxo-2, 5-dihydro-furan-2-yl)-2-hydroxy-ethoxycarbonylmethyl]-formyl-amino}-pent-3-enyl ester.

MS(ESI) 808 (M+H)$^+$ $^1$HNMR (Methanol-D4) δ8.06-7.97 (3H, m); 7.52-7.45 (1H, m); 5.5 (1H, d); 4.52-4.39 (5H, m); 4.75-4.62, 3.26 (2H, m); 4.24 (2H, m); 3.04-2.87 (8H, m); 2.71-2.59 (2H, m); 2.42-2.35 (4H, m); 2.11-1.62 (11H, m); 1.27 (3H, t).

Pharmacological Experiment and Analysis

I. Pharmacokinetic Experiments

In order to evaluate the distribution of the compound of the present invention (abbreviated as prodrug) in brain tissue and plasma, a prototype drug Compound a (prepared by the preparation method of Example 51 in CN101742911A) and prodrugs prepared in Example 1-22 were selected for the determination of drug concentration in brains and plasmas of mice.

The experimental animals were selected from Kunming mice (purchased from SPF (Beijing) Experimental Animal Science and Technology Co., Ltd.), 20-22 g in weight. The mice were randomly grouped (23 groups, 45 mice in each group), and administered via tail vein with 1 mg/kg of prototype drug Compound a or an equimolar dose of each prodrug as prepared by the Examples, the mice were sacrificed at 5 min, 15 min, 30 min, 45 min, 60 min, 90 min, 120 min, 240 min, 480 min, respectively, 5 mice from each group were sacrificed at each time point. 1 mL of blood was collected from the eyelid of each mouse, 50 μL of plasma was obtained by centrifugation. The plasma was diluted with 200 μL of methanol to obtain a plasma sample and stored at −20° C. Meanwhile, the brain tissue of each mouse was removed, weighed and homogenized, and diluted with methanol in a ratio of 1:5 (g/mL) to obtain a brain homogenate sample. The brain homogenate sample was stored at −20° C. 200 ng/mL internal standard (glipizide) was added to each tissue sample. After vortex for 3 min, the sample was centrifuged at 9500 rpm for 15 min, extracted to obtain 50 μL of the supernatant, 50 μL of water was added thereto and mixed. 10 μL of the sample was extracted, analyzed by LC-MS/MS to determine the concentration of the prototype drug Compound a, $AUC_{0-t}$ and $MRT_{0-t}$ of each sample were calculated by drug concentration-time curves of brain and plasma, and the brain-targeting effect of each prodrug was evaluated by the ratio of $AUC_{0-t}$ of each prodrug group to the $AUC_{0-t}$ of the prototype drug group.

The pharmacokinetic parameters of the prototype drug Compound a and each of the prodrugs in plasma are shown in Table 1, and the pharmacokinetic parameters in brain homogenate are shown in Table 2.

TABLE 1

Pharmacokinetic parameters of prototype drug (Compound a) and each of the prodrugs in plasma

| Compound | $AUC_{0-t}$ (h * ng/mL) | $MRT_{0-t}$ (h) | $(AUC_{0-t})_{prodrug\ group}/ (AUC_{0-t})_{prototype\ drug\ group}$ |
|---|---|---|---|
| Compound a | 951.66 | 1.08 | |
| Compound 1 | 456.32 | 0.86 | 0.48 |
| Compound 2 | 466.78 | 0.89 | 0.49 |
| Compound 3 | 589.34 | 0.92 | 0.62 |
| Compound 4 | 650.66 | 0.84 | 0.68 |
| Compound 5 | 632.98 | 0.88 | 0.67 |
| Compound 6 | 587.12 | 0.83 | 0.62 |
| Compound 7 | 500.34 | 0.90 | 0.53 |
| Compound 8 | 590.58 | 0.92 | 0.62 |
| Compound 9 | 488.54 | 0.87 | 0.51 |
| Compound 10 | 443.98 | 0.85 | 0.47 |
| Compound 11 | 688.97 | 0.89 | 0.72 |
| Compound 12 | 433.78 | 0.80 | 0.46 |
| Compound 13 | 568.15 | 0.87 | 0.60 |
| Compound 14 | 615.47 | 0.95 | 0.65 |
| Compound 15 | 384.16 | 0.83 | 0.41 |
| Compound 16 | 390.63 | 0.78 | 0.41 |
| Compound 17 | 580.98 | 1.02 | 0.61 |
| Compound 18 | 690.56 | 0.96 | 0.73 |
| Compound 19 | 699.45 | 1.03 | 0.73 |
| Compound 20 | 783.29 | 0.90 | 0.82 |
| Compound 21 | 757.07 | 1.05 | 0.80 |
| Compound 21 | 786.43 | 1.10 | 0.83 |

The data in Table 1 show that the $AUC_{0-t}$ ratios of the groups of prodrugs prepared by the Examples to the prototype drug group in plasma are between 0.41 and 0.82, indicating that each of the prodrugs can effectively reduce the distribution of Compound a in plasma, suggesting that it may reduce peripheral toxic side effects and can increase the distribution in brain tissue.

TABLE 2

Pharmacokinetic parameters of the prototype drug
(Compound a) and each prodrug in brain homogenate

| Compound | $AUC_{0-t}$ (h * ng/g) | $MRT_{0-t}$ (h) | $(AUC_{0-t})_{prodrug}/(AUC_{0-t})_{prototype\ drug}$ |
|---|---|---|---|
| Compound a | 504.32 | 0.70 | |
| Compound 1 | 780.89 | 1.56 | 1.55 |
| Compound 2 | 865.87 | 1.78 | 1.72 |
| Compound 3 | 890.56 | 1.89 | 1.77 |
| Compound 4 | 788.90 | 1.93 | 1.56 |
| Compound 5 | 856.76 | 1.71 | 1.70 |
| Compound 6 | 950.32 | 1.53 | 1.88 |
| Compound 7 | 750.65 | 1.24 | 1.49 |
| Compound 8 | 870.42 | 1.63 | 1.73 |
| Compound 9 | 878.65 | 1.56 | 1.74 |
| Compound 10 | 940.26 | 1.94 | 1.86 |
| Compound 11 | 970.78 | 2.02 | 1.92 |
| Compound 12 | 970.41 | 2.01 | 1.92 |
| Compound 13 | 988.54 | 2.05 | 1.96 |
| Compound 14 | 1000.87 | 2.15 | 1.98 |
| Compound 15 | 1125.49 | 2.30 | 2.23 |
| Compound 16 | 940.36 | 1.84 | 1.86 |
| Compound 17 | 780.56 | 1.76 | 1.55 |
| Compound 18 | 856.33 | 1.89 | 1.70 |
| Compound 19 | 710.77 | 1.41 | 1.41 |
| Compound 20 | 835.71 | 1.38 | 1.65 |
| Compound 21 | 848.72 | 1.91 | 1.68 |
| Compound 22 | 920.10 | 2.00 | 1.82 |

8,9-tetrahydrodemethylthebaine, Chinese Journal of Organic Chemistry, 2005, 25(2), 210-212), is the most potent opioid receptor agonist has been found so far, the affinity value to p opioid receptors is $K_i$=0.91 nM. Sixty KM mice (purchased from SPF (Beijing) Experimental Animal Science and Technology Co., Ltd.) were randomly grouped, 10 mice in each group. Compound 15 was administrated via tail vein in 4 doses, i.e., 30 mg/kg, 10 mg/kg, 3 mg/kg (repeated once), 1 mg/kg, respectively, and the administration time was recorded. After 10 minutes of administration, the mice were injected subcutaneously with 030418 at a dose of 15 mg/kg. Another 10 randomly grouped mice were injected subcutaneously with 030418 as a control group at a dose of 15 mg/kg. During the experiment and 24 hours after the experiment, time when the poisoning reactions occurred, main poisoning reactions and time of death were observed and recorded. The observation indicators in the experiment include general indicators (e.g., animal appearance, behavior, response to stimuli, secretions, excretions, etc.), and animal death situation (time of death, pre-death reaction, etc.) and the like. All death situations, symptoms, symptoms onset time, seriousness, duration and so on were recorded. Death rate was calculated (number of dead animals/number of samples).

The experimental results of Compound 15 against 030418-induced acute death in mice are shown in Table 3.

TABLE 3

Experimental results of Compound 15 against 030418-induced acute death in mice

| Experiment | Treatment | Compound | n | Administration | Dose (mg/kg) | Death rate |
|---|---|---|---|---|---|---|
| Anti-respiratory depression | 030418, 15 mg/kg, sc | Normal Saline | 10 | iv | | 80% |
| Anti-respiratory depression | 030418, 15 mg/kg, sc | Compound a | 10 | iv | 10 | 20% |
| Anti-respiratory depression | 030418, 15 mg/kg, sc | Compound 15 | 10 | iv | 30 | 0% |
| Anti-respiratory depression | 030418, 15 mg/kg, sc | Compound 15 | 10 | iv | 10 | 0% |
| Anti-respiratory depression | 030418, 15 mg/kg, sc | Compound 15 | 20 | iv | 3 | 20% |
| Anti-respiratory depression | 030418, 15 mg/kg, sc | Compound 15 | 10 | iv | 1 | 30% |
| Anti-respiratory depression | 030418, 15 mg/kg, sc | Compound 15 | 10 | iv | 0.5 | 50% |

Note:
sc-subcutaneous injection, iv-intravenous injection

The data in Table 2 show that the $AUC_{0-t}$ ratios of the groups of the prodrugs prepared by the Examples to the prototype drug group in the brain homogenate are between 1.41 and 2.23, indicating that each of the prodrugs does increase the distribution of Compound a in brain homogenate, suggesting that the prodrugs have obvious brain-targeting effect, and the released prototype drug is obviously enriched in the brain.

II. Pharmacodynamics Experiment

1) Experiments Against 030418-Induced Acute Death in Mice 030418 (N-methyl-7α-[(R)-1-hydroxy-1-methyl-3-(thien-3-yl)-propyl]-6,14-endo-ethano-6,7,8,14-tetrahydronorori pavine), the preparation method of which refers to Zhongbo Hua, Liu He, Wu Bo, Wang Yaping, Synthesis and crystal structure of N-cyclopropylmethyl-7α-[(R)-1-hydroxyl-1-methyl-3-(2-thienyl)propyl]-6,14-endoethano-6,7, The experimental data in Table 3 show that Compound 15 can increase the survival rate of mice in a dose-dependent manner, and the same anti-lethal effect can be achieved with only one-eighth of the molar dose of Compound a, indicating that Compound 15 can effectively reduce the dose, suggesting it may have good security and effectiveness.

In summary, the present invention synthesizes a series of prodrugs of AMPA receptor synergist as shown by Formula I. The pharmacokinetic experimental data indicate that the prodrugs have significant brain-targeting effects, suggesting that these prodrugs can increase the safety and effectiveness of AMPA receptor synergist in the treatment of respiratory depression.

2) Effects on Respiratory Function Parameters of 030418-Induced Respiratory Depression Rats Rats (purchased from SPF (Beijing) Experimental Animal Science and Technology Co., Ltd.) were randomly divided into 3 groups (5 in each group), and the basis respiratory function parameters of rats in each group were determined using a conscious animal lung function tester (EMKA, EMKA Technologies Inc.). The rats were administrated with 030418 (20 μg/kg) via tail vein, the administration time was recorded, and the respiratory function parameters of the rats with respiratory depression were measured. After 10 minutes of administration of 030418, different concentrations of Compound 15 or Compound a were administered via tail vein, and the changes of respiratory function parameters over time were measured within 2 h.

Figure 2:
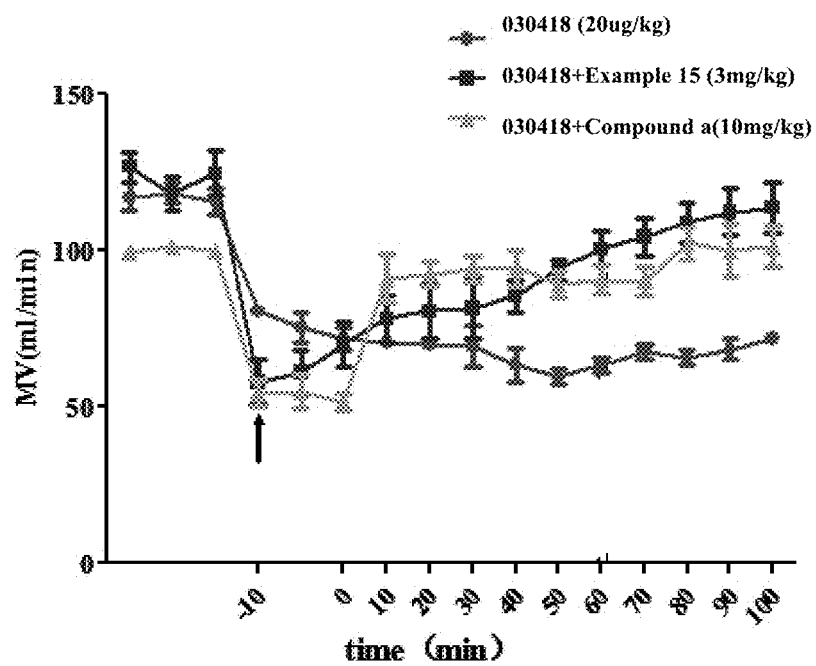
FIG. 2 shows the effect of Compound 15 on ventilation in rats with respiratory depression, wherein the ordinate is Minute Volume (MV).

As shown in FIG. 1 and FIG. 2, Compound 15 shows a dose-dependent antagonism toward the decreased respiratory rate and ventilation caused by opioid agonist 030418, indicating that Compound 15 has good activity against respiratory depression. In addition, 3 mg/kg of Compound 15 can achieve the same effect as Compound a (10 mg/kg), indicating that Compound 15 has good brain-targeting effect.

Although the embodiments of the present invention have been described in details, a person skilled in the art would understand that, various modifications and replacements may be performed to the details in accordance with the teachings of the disclosure. These changes are all fall within the scope of the present invention. The whole scope of the present invention is defined by the attached claims and any equivalents thereof.

What is claimed is:

1. A compound of Formula (I), a geometric or optical isomer, a pharmaceutically acceptable salt, a solvate or a polymorph thereof:

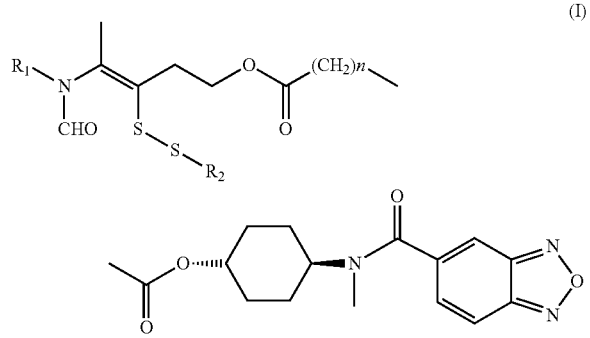

(I)

wherein, $R_1$ represents $C_1$-$C_5$ linear or branched alkyl,

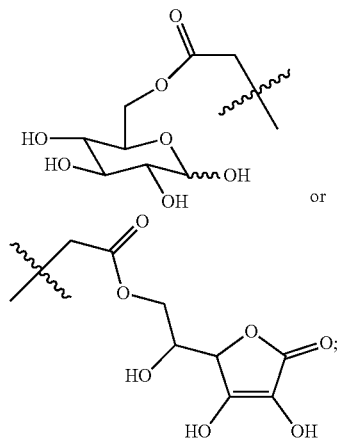

$R_2$ represents $C_1$-$C_{10}$ linear or branched alkyl, phenyl-$C_1$-$C_4$ alkyl;

n represents an integer selected from 1-5.

2. The compound, the geometric or optical isomer, the pharmaceutically acceptable salt, the solvate or the polymorph thereof according to claim 1, wherein, $R_1$ represents $C_1$-$C_5$ linear or branched alkyl,

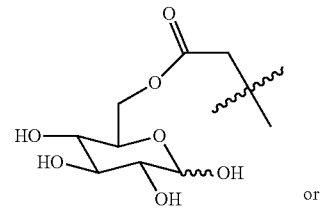

or

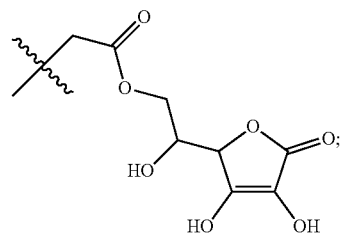

$R_2$ represents $C_1$-$C_{10}$ linear or branched alkyl, benzyl, phenylethyl, phenylpropyl;

n represents an integer selected from 1-5.

3. The compound, the geometric or optical isomer, the pharmaceutically acceptable salt, the solvate or the polymorph thereof according to claim 1, wherein, $R_1$ represents $C_1$-$C_5$ linear or branched alkyl,

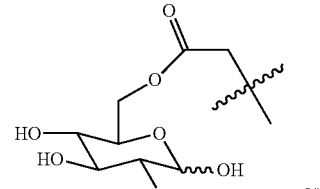

or

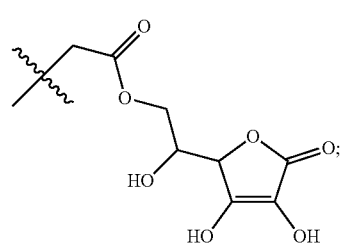

$R_2$ represents $C_1$-$C_{10}$ linear or branched alkyl;

n represents an integer selected from 1-5.

4. The compound, the geometric or optical isomer, the pharmaceutically acceptable salt, the polymorph thereof according to claim 1, wherein, $R_1$ represents $C_1$-$C_4$ linear or branched alkyl,

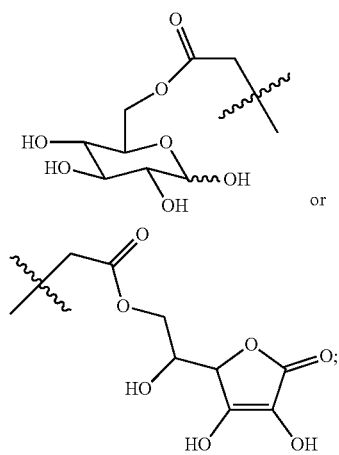

or $R_2$ represents $C_1$-$C_8$ linear or branched alkyl;
n represents an integer selected from 1-4.

5. The compound, the geometric or optical isomer, the pharmaceutically acceptable salt, the solvate or the polymorph thereof according to claim 1, wherein, $R_1$ represents $C_1$-$C_4$ linear or branched alkyl,

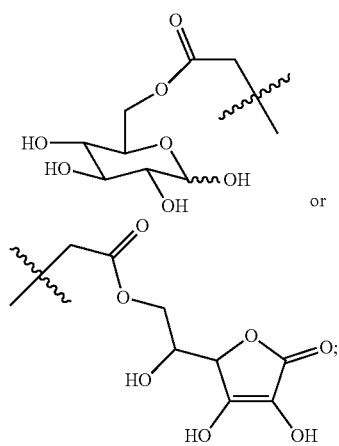

or $R_2$ represents $C_1$-$C_6$ linear or branched alkyl;
n represents an integer selected from 1-3.

6. The compound, the geometric or optical isomer, the pharmaceutically acceptable salt, the solvate or the polymorph thereof according to claim 1, wherein, $R_1$ represents $C_1$-$C_4$ linear or branched alkyl,

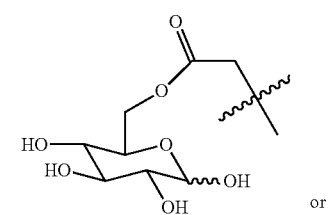

or

-continued

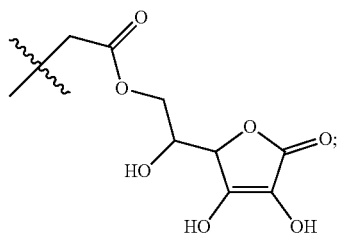

$R_2$ represents $C_1$-$C_6$ linear or branched alkyl;
n represents an integer selected from 2-4.

7. The compound, the geometric or optical isomer, the pharmaceutically acceptable salt, the solvate or the polymorph thereof according to claim 1, wherein, $R_1$ represents $CH_3$—, $CH_3CH_2$—, $CH_3CH_2CH_2$—,

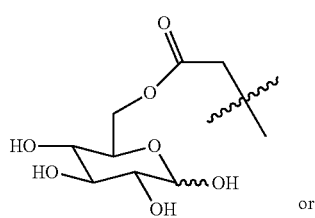

or

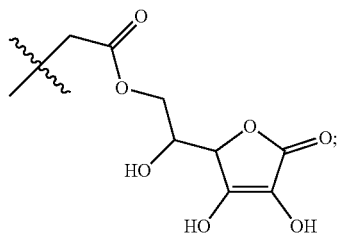

$R_2$ represents —$CH_2CH_3$, —$CH_2CH_2CH_3$, —$CH(CH_3)_2$, —$CH_2CH_2CH_2CH_3$, —$CH_2CH(CH_3)_2$, —$CH_2CH_2CH_2CH_2CH_3$, —$CH_2CH_2CH(CH_3)_2$, —$CH_2CH_2CH_2CH_2CH_2CH_3$ or

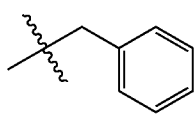 [SMILES: *Cc1ccccc1]

n represents 2 or 3.

8. The compound, the geometric or optical isomer, the pharmaceutically acceptable salt, the solvate or the polymorph thereof according to claim 1, wherein the compound has a structure as shown in Formula (II),

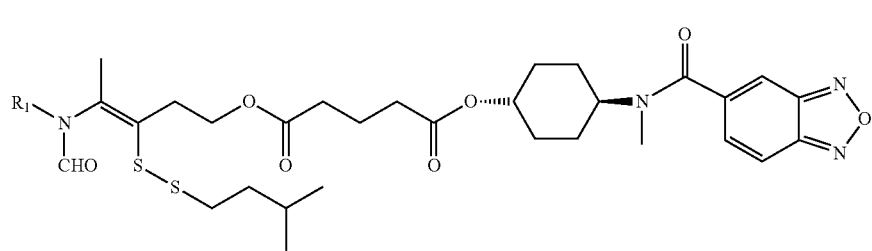

wherein, R₁ represents CH₃—, CH₃CH₂—, CH₃CH₂CH₂—, (CH₃)₂CH₂—,

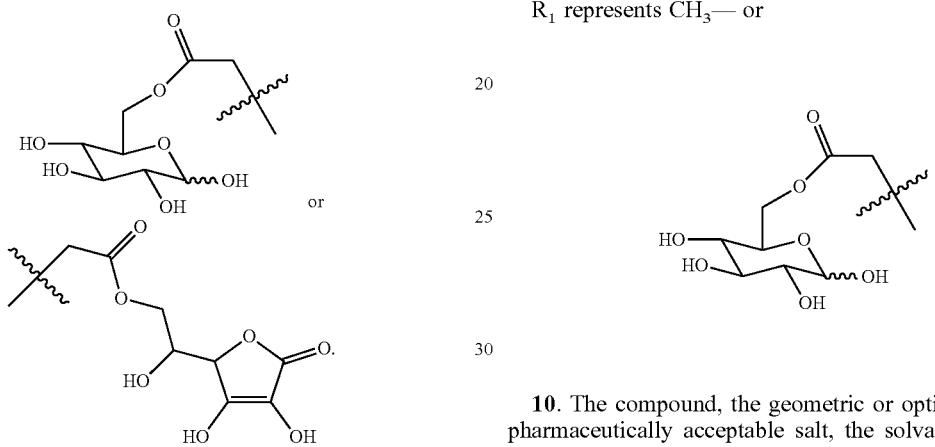

or

9. The compound, the geometric or optical isomer, the pharmaceutically acceptable salt, the solvate or the polymorph thereof according to claim 8, wherein:

R₁ represents CH₃— or

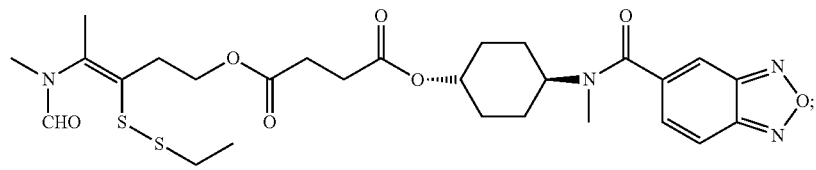

10. The compound, the geometric or optical isomer, the pharmaceutically acceptable salt, the solvate or the polymorph thereof according to claim 1, wherein the compound is selected from:

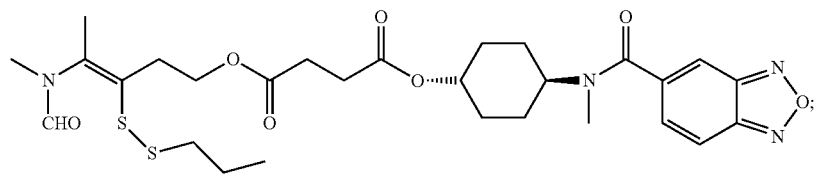

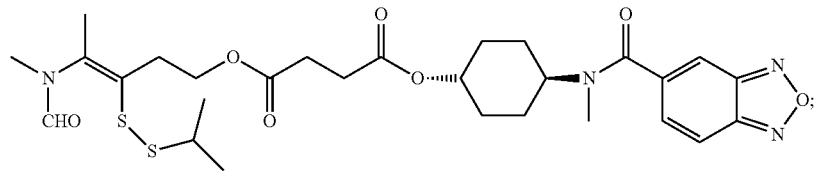

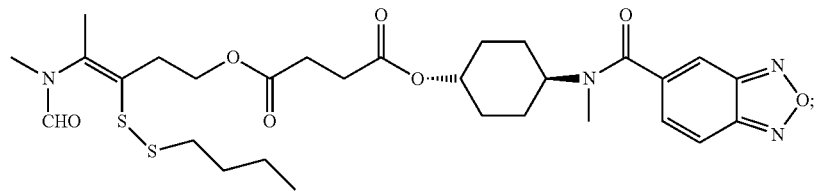

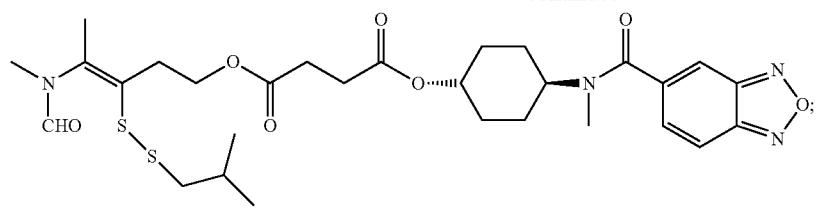
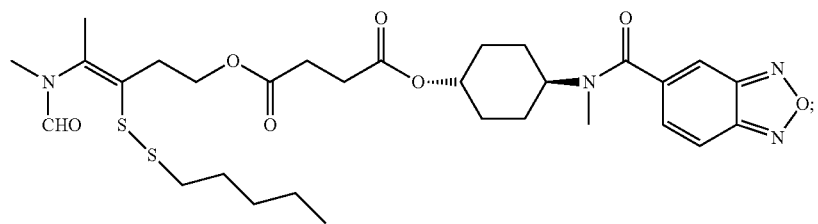
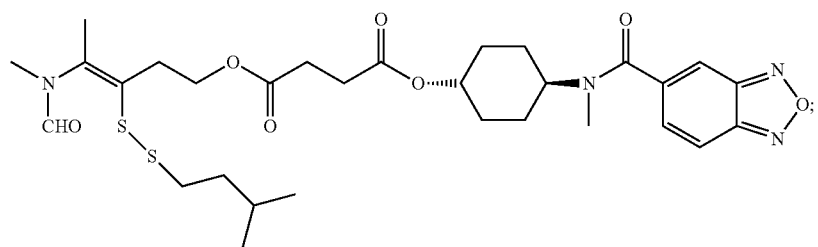
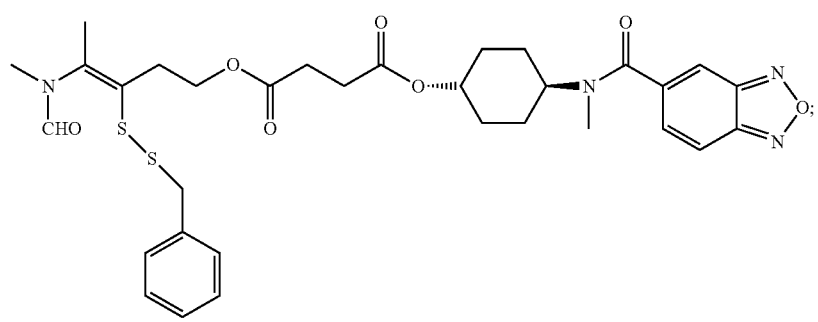
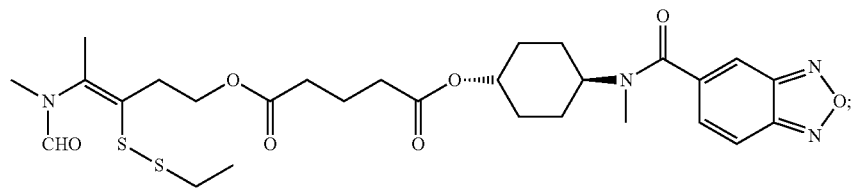
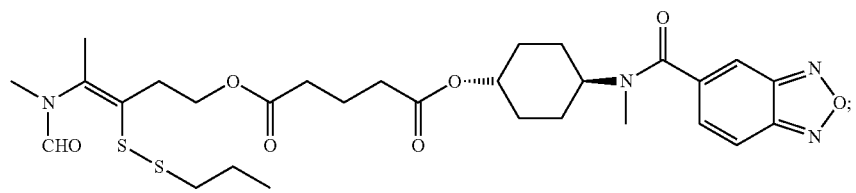
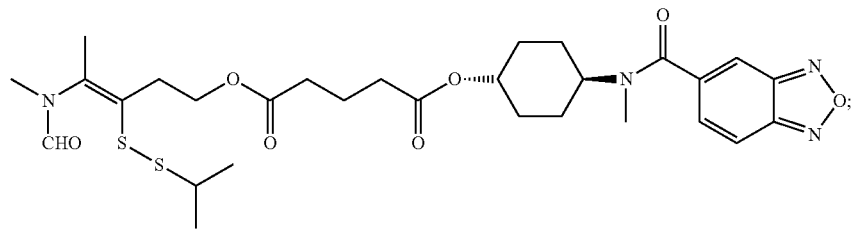

-continued
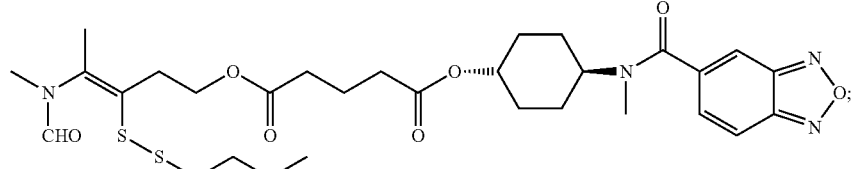
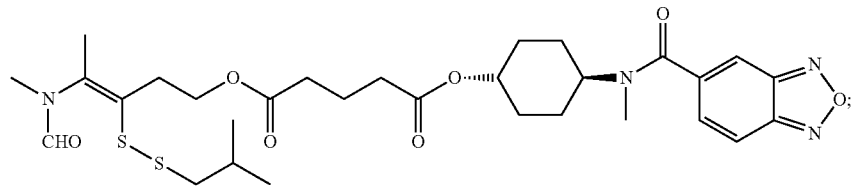
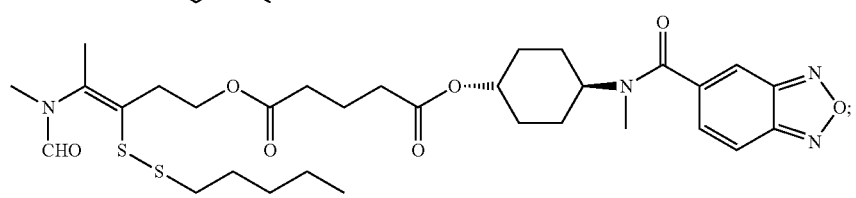
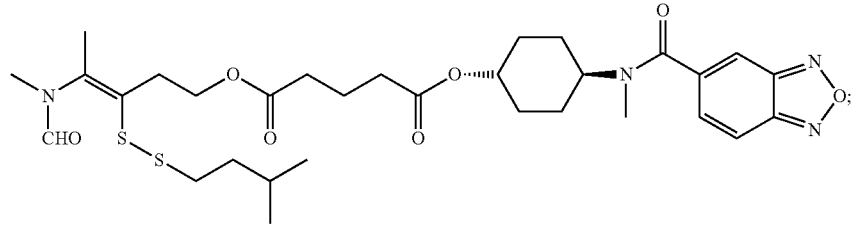
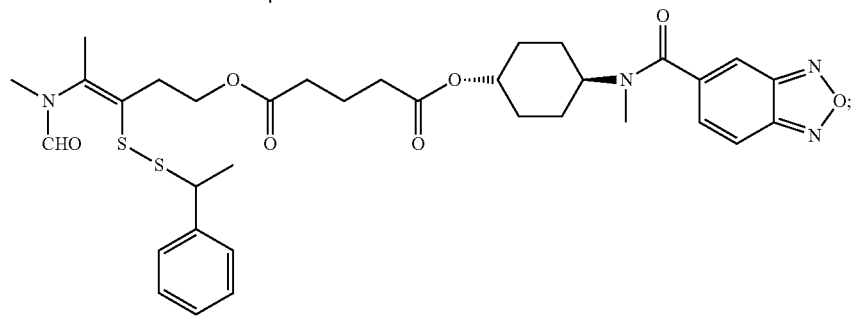
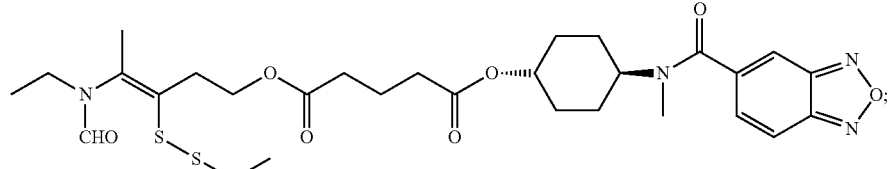
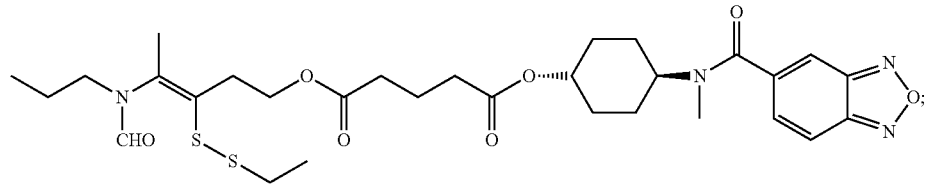
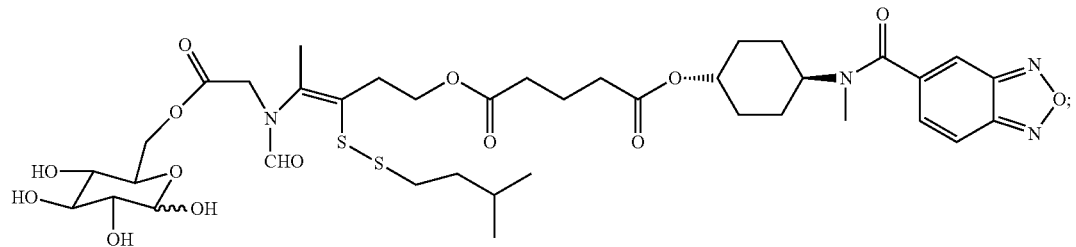

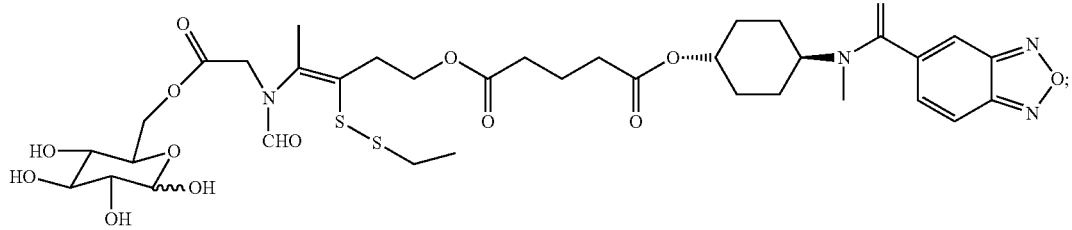

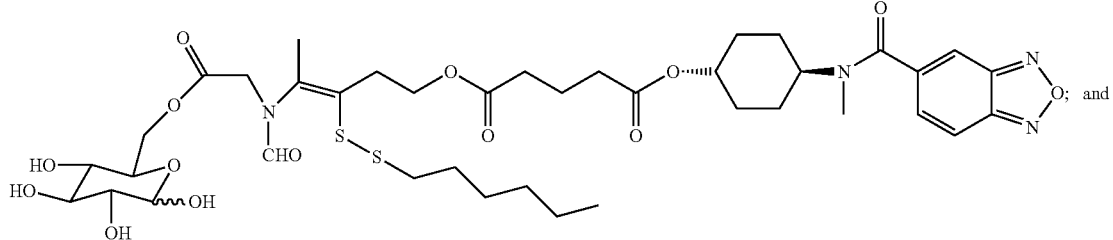

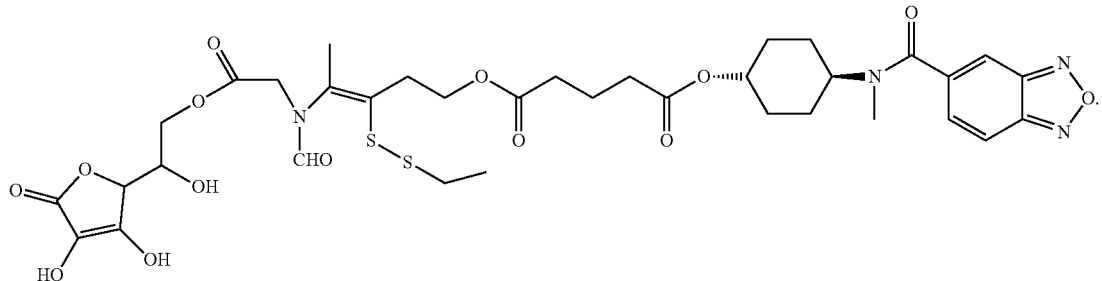

11. A pharmaceutical composition, comprising an effective amount of the compound, the geometric or optical isomer, the pharmaceutically acceptable salt, the solvate or the polymorph thereof according to claim 1, and one or more pharmaceutically acceptable carriers, additives or excipients.

12. A method for treating a disease or disorder or for alleviating the severity of the disease or disorder, wherein the method comprises administering to a patient in need of such treatment a therapeutically effective amount of at least one of the compound, the geometric or optical isomer, the pharmaceutically acceptable salt, the solvate or the polymorph thereof according to claim 1, wherein the disease or disorder is selected from the group consisting of a hypoglutamatergic condition, impaired memory or other cognitive functions caused by a deficiency in the number or strength of excitatory synapses, or a deficiency in the number of DL-α-amino-3-hydroxy-5-methyl-4-isoxazolyl propionic acid (AMPA) receptors, schizophrenia or schizophreniform behavior caused by a cortical/striatal imbalance due to a deficiency in the number or strength of excitatory synapses, or a deficiency in the number of DL-α-amino-3-hydroxy-5-methyl-4-isoxazolyl propionic acid (AMPA) receptors, attention deficit hyperactivity disorder, Rett syndrome, fragile-X syndrome, respiratory depression, breathing-related sleep disorder or sleep apnea, Alzheimer's disease, schizophrenia, Parkinson's disease and sleep deprivation.

13. A method for treating respiratory depression in a patient in need of such treatment,
comprising administering to the patient an effective amount of the compound, the geometric or optical isomer, the pharmaceutically acceptable salt, the solvate or the polymorph thereof according to claim 1, in combination with an opiate or an opioid analgesic, or
comprising administering to the patient an effective amount of the compound, the geometric or optical isomer, the pharmaceutically acceptable salt, the solvate or the polymorph thereof according to claim 1, in combination with an anesthetic.

14. A method for treating Alzheimer's disease in a patient in need of such treatment, comprising administering to the patient an effective amount of the compound, the geometric or optical isomer, the pharmaceutically acceptable salt, the solvate or the polymorph thereof according to claim 1, in combination with an acetylcholinesterase inhibitor.

15. A method for the preparation of the compound, the geometric or optical isomer, the pharmaceutically acceptable salt, the solvate or the polymorph thereof according to claim 1, comprising the following steps of:

a) reacting sodium thiosulfate with $R_2Br$ to give a compound of Formula (III);

$$NaO-\overset{O}{\underset{O}{\overset{\|}{S}}}-SR_2 \quad (III)$$

b) reacting 4-methyl-5-thiazoleethanol with $R_1I$ to give a compound of Formula (IV);

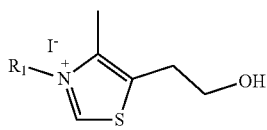
(IV)

c) reacting a compound of the Formula (III) with a compound of the Formula (IV) to give a compound of Formula (V);

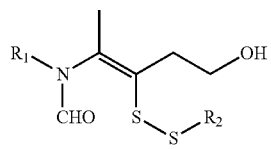
(V)

d) reacting a compound of Formula (V) with an acid anhydride represented by

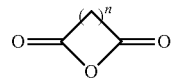

to give a compound of Formula (VI);

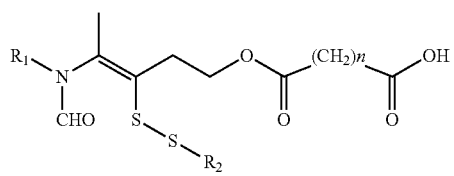
(VI)

e) reacting a compound of Formula (VI) with N-(anti-4-hydroxycyclohexyl)-N-methyl-benzo[c][1,2,5]oxadiazol-5-yl-carboxamide to obtain a compound of Formula (I),
wherein: $R_1$ represents $C_1$-$C_5$ linear or branched alkyl, $R_2$ and n are as defined in Formula (I).

16. A method for the preparation of the compound, the geometric or optical isomer, the pharmaceutically acceptable salt, the solvate or the polymorph thereof according to claim 1, comprising the following steps of:
 a) reacting sodium thiosulfate with $R_2Br$ to give a compound of Formula (III) for further use;

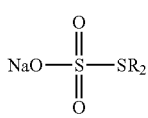
(III)

b) reacting 4-methyl-5-thiazoleethanol with a tert-butyl bromoacetate to give N-tert-butoxycarbonylmethyl-4-methyl-5-(2-hydroxyl-ethyl)-thiazole bromide of Formula (VII);

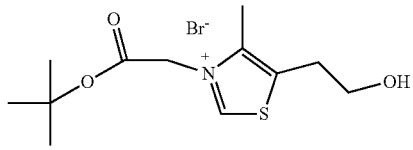
(VII)

c) reacting a compound of Formula (III) with a compound of Formula (VII) to give a compound of Formula (VIII);

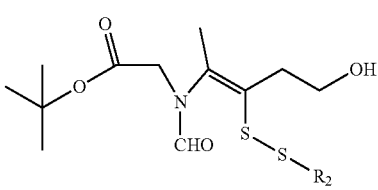
(VIII)

d) reacting a compound of Formula (VIII) with an acid anhydride represented by

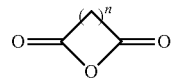

to give a compound of Formula (IX);

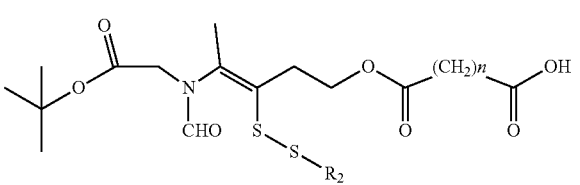
(IX)

e) reacting a compound of Formula (IX) with N-(anti-4-hydroxycyclohexyl)-N-methylbenzo[c][1,2,5]oxadiazol-5-yl-carboxamide to give a compound of Formula (X);

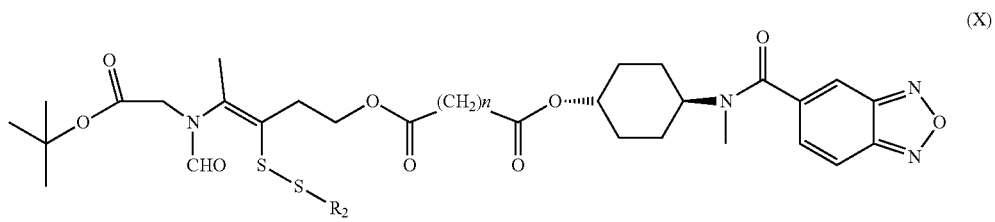

f) removing the tert-butoxyl from a compound of Formula (X) to give a compound of formula (XI);

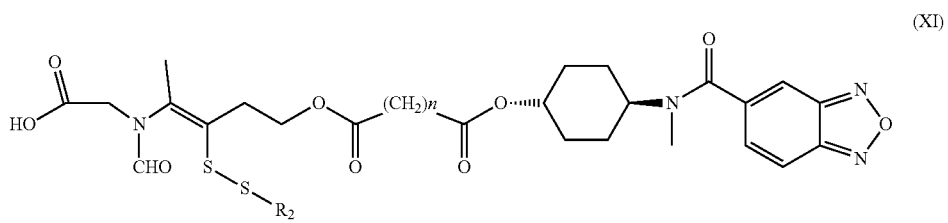

g) reacting a compound of the formula (XI) with an acetyl-protected glucose/L-ascorbic acid to give a compound of formula (XII);

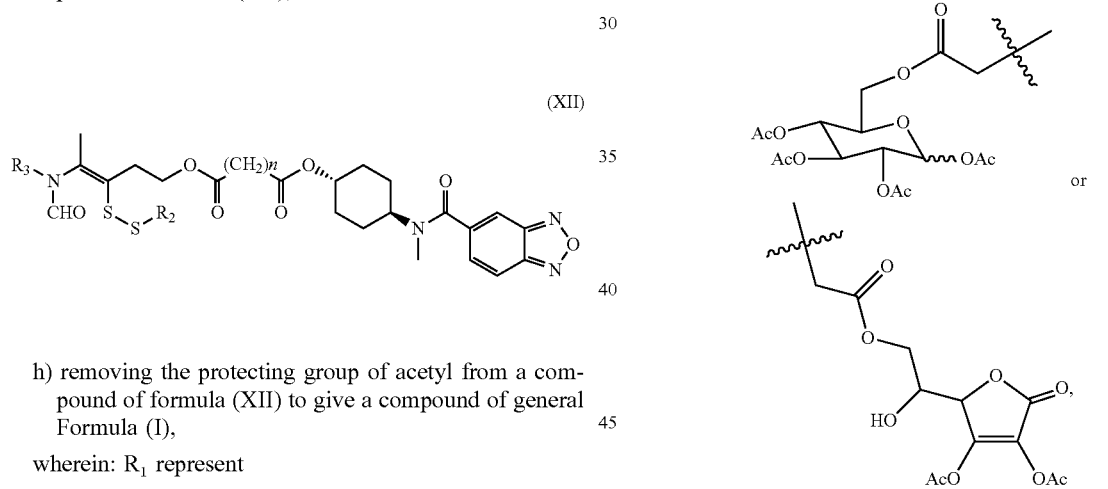

h) removing the protecting group of acetyl from a compound of formula (XII) to give a compound of general Formula (I), wherein: $R_1$ represent

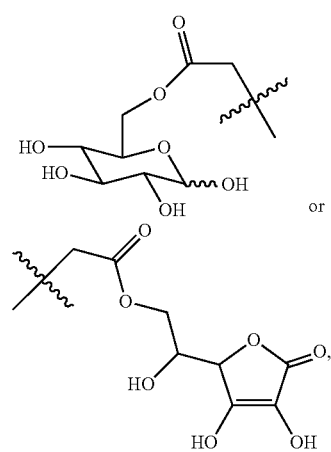

$R_3$ represents

[structures shown]

$R_2$ and n are as defined in Formula (I).

17. The compound, the geometric or optical isomer, the pharmaceutically acceptable salt, the solvate or the polymorph thereof according to claim 7, wherein $R_2$ represents —$CH_2CH_3$, —$CH_2CH_2CH_3$, —$CH(CH_3)_2$, —$CH_2CH_2CH_2CH_3$, —$CH_2CH(CH_3)_2$, —$CH_2CH_2CH_2CH_2CH_3$, —$CH_2CH_2CH(CH_3)_2$ or —$CH_2CH_2CH_2CH_2CH_2CH_3$.

18. The compound, the geometric or optical isomer, the pharmaceutically acceptable salt, the solvate or the polymorph thereof according to claim 9, wherein $R_1$ represents $CH_3$—.

19. The pharmaceutical composition according to claim 11, wherein the compound accounts for about 0.5-75 wt % of the composition, and the carriers, additives or excipients account for about 25-95.5 wt % of the composition.

20. The method according to claim 13, wherein the anesthetic is propofol or a barbiturate salt.

* * * * *